(12) United States Patent
Lin et al.

(10) Patent No.: US 9,123,903 B2
(45) Date of Patent: *Sep. 1, 2015

(54) DIBENZOTHIOPHENE-CONTAINING MATERIALS IN PHOSPHORESCENT LIGHT EMITTING DIODES

(71) Applicant: Universal Display Corporation, Ewing, NJ (US)

(72) Inventors: Chun Lin, Yardley, PA (US); Alexey Dyatkin, Ambler, PA (US); Zeinab Elshenawy, Holland, PA (US); Walter Yeager, Yardley, PA (US)

(73) Assignee: Universal Display Corporation, Ewing, NJ (US)

( * ) Notice: Subject to any disclaimer, the term of this patent is extended or adjusted under 35 U.S.C. 154(b) by 161 days.

This patent is subject to a terminal disclaimer.

(21) Appl. No.: 14/026,868

(22) Filed: Sep. 13, 2013

(65) Prior Publication Data

US 2014/0008643 A1 Jan. 9, 2014

Related U.S. Application Data

(62) Division of application No. 13/186,204, filed on Jul. 19, 2011, now Pat. No. 8,580,402, which is a division of application No. 12/208,907, filed on Sep. 11, 2008, now Pat. No. 8,007,927.

(60) Provisional application No. 61/017,480, filed on Dec. 28, 2007.

(51) Int. Cl.
*H01L 51/54* (2006.01)
*H01L 51/00* (2006.01)
(Continued)

(52) U.S. Cl.
CPC .......... *H01L 51/0085* (2013.01); *C07D 209/86* (2013.01); *C07D 235/18* (2013.01); *C07D 235/20* (2013.01); *C07D 333/76* (2013.01); *C07D 405/14* (2013.01); *C07D 409/10* (2013.01); *C07D 409/14* (2013.01); *C07D 413/10* (2013.01); *C07D 471/04* (2013.01);
(Continued)

(58) Field of Classification Search
None
See application file for complete search history.

(56) References Cited

U.S. PATENT DOCUMENTS

| 4,769,292 A | 9/1988 | Tang et al. |
| 5,061,569 A | 10/1991 | VanSlyke et al. |

(Continued)

FOREIGN PATENT DOCUMENTS

| EP | 0650955 | 5/1995 |
| EP | 1725079 | 11/2006 |

(Continued)

OTHER PUBLICATIONS

Xu, et al., "Facile syntehsis of novel monodisperse linear 3,9-linked oligocarbazoles," Tetrahedron Letters 46 (2005) p. 6883-6886.

(Continued)

*Primary Examiner* — Gregory Clark
(74) *Attorney, Agent, or Firm* — Duane Morris LLP

(57) ABSTRACT

An organic light emitting device that includes an anode, a cathode, an enhancement layer, and an emissive layer that includes homoleptic iridium complexes containing phenylimidazole ligands, which include at least one fused substituent. The enhancement layer also includes a new dibenzothiophene and dibenzofuran-containing compound that is useful as a material in an enhancement layer.

6 Claims, 14 Drawing Sheets

(51) Int. Cl.

| | |
|---|---|
| *C07D 209/86* | (2006.01) |
| *C07D 235/18* | (2006.01) |
| *C07D 235/20* | (2006.01) |
| *C07D 333/76* | (2006.01) |
| *C07D 405/14* | (2006.01) |
| *C07D 409/10* | (2006.01) |
| *C07D 409/14* | (2006.01) |
| *C07D 413/10* | (2006.01) |
| *C07D 471/04* | (2006.01) |
| *C07D 487/04* | (2006.01) |
| *C07F 5/02* | (2006.01) |
| *C07F 7/08* | (2006.01) |

(52) U.S. Cl.
CPC ............ *C07D 487/04* (2013.01); *C07F 5/027* (2013.01); *C07F 7/0814* (2013.01); *H01L 51/0071* (2013.01)

(56) References Cited

U.S. PATENT DOCUMENTS

| | | | |
|---|---|---|---|
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,687,266 B1 | 2/2004 | Ma et al. | |
| 6,835,469 B2 | 12/2004 | Kwong et al. | |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |
| 7,329,722 B2 | 2/2008 | Vaitkeviciene et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,504,769 B2 | 3/2009 | Rado et al. | |
| 7,534,505 B2 | 5/2009 | Lin et al. | |
| 7,651,791 B2 | 1/2010 | Nakano et al. | |
| 7,989,644 B2 | 8/2011 | Tanabe et al. | |
| 8,007,927 B2 | 8/2011 | Lin et al. | |
| 8,221,905 B2 | 7/2012 | Lin et al. | |
| 8,367,850 B2 | 2/2013 | Ma et al. | |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0151042 A1 | 8/2003 | Hueschen | |
| 2003/0152802 A1 | 8/2003 | Tsuboyama et al. | |
| 2003/0175553 A1 | 9/2003 | Thompson et al. | |
| 2003/0230980 A1 | 12/2003 | Forrest et al. | |
| 2004/0036077 A1 | 2/2004 | Ise | |
| 2004/0137267 A1 | 7/2004 | Igarashi et al. | |
| 2004/0137268 A1 | 7/2004 | Igarashi et al. | |
| 2004/0174116 A1 | 9/2004 | Lu et al. | |
| 2005/0025993 A1 | 2/2005 | Thompson et al. | |
| 2005/0112407 A1 | 5/2005 | Ogasawara et al. | |
| 2005/0238919 A1 | 10/2005 | Ogasawara | |
| 2005/0244673 A1 | 11/2005 | Satoh et al. | |
| 2005/0260441 A1 | 11/2005 | Thompson et al. | |
| 2005/0260449 A1 | 11/2005 | Walters et al. | |
| 2006/0008670 A1 | 1/2006 | Lin et al. | |
| 2006/0202194 A1 | 9/2006 | Jeong et al. | |
| 2006/0240279 A1 | 10/2006 | Adamovich et al. | |
| 2006/0251923 A1 | 11/2006 | Lin et al. | |
| 2006/0263635 A1 | 11/2006 | Ise | |
| 2006/0280965 A1 | 12/2006 | Kwong et al. | |
| 2007/0075631 A1 | 4/2007 | Tung et al. | |
| 2007/0190359 A1 | 8/2007 | Knowles et al. | |
| 2007/0224446 A1 | 9/2007 | Nakano et al. | |
| 2007/0278938 A1 | 12/2007 | Yabunouchi et al. | |
| 2008/0015355 A1 | 1/2008 | Schafer et al. | |
| 2008/0018221 A1 | 1/2008 | Egen et al. | |
| 2008/0106190 A1 | 5/2008 | Yabunouchi et al. | |
| 2008/0124572 A1 | 5/2008 | Mizuki et al. | |
| 2008/0220265 A1 | 9/2008 | Xia et al. | |
| 2008/0297033 A1 | 12/2008 | Knowles et al. | |
| 2009/0008605 A1 | 1/2009 | Kawamura et al. | |
| 2009/0009065 A1 | 1/2009 | Nishimura et al. | |
| 2009/0017330 A1 | 1/2009 | Iwakuma et al. | |
| 2009/0030202 A1 | 1/2009 | Iwakuma et al. | |
| 2009/0039776 A1 | 2/2009 | Yamada et al. | |
| 2009/0045730 A1 | 2/2009 | Nishimura et al. | |
| 2009/0045731 A1 | 2/2009 | Nishimura et al. | |
| 2009/0101870 A1 | 4/2009 | Prakash et al. | |
| 2009/0108737 A1 | 4/2009 | Kwong et al. | |
| 2009/0115316 A1 | 5/2009 | Zheng et al. | |
| 2009/0153034 A1 | 6/2009 | Lin et al. | |
| 2009/0165846 A1 | 7/2009 | Johannes et al. | |
| 2009/0167162 A1 | 7/2009 | Lin et al. | |
| 2009/0179554 A1 | 7/2009 | Kuma et al. | |
| 2011/0057559 A1 | 3/2011 | Xia et al. | |
| 2011/0084599 A1 | 4/2011 | Brooks et al. | |
| 2011/0278552 A1 | 11/2011 | Numata | |
| 2013/0020565 A1 | 1/2013 | Numata | |
| 2013/0175510 A1 | 7/2013 | Ma et al. | |

FOREIGN PATENT DOCUMENTS

| | | |
|---|---|---|
| EP | 2034538 | 3/2009 |
| JP | 62283341 | 12/1987 |
| JP | 07-053950 | 2/1995 |
| JP | 200511610 | 1/2005 |
| JP | 2007123392 | 5/2007 |
| JP | 2007126403 | 5/2007 |
| JP | 2007254297 | 10/2007 |
| JP | 2008074939 | 4/2008 |
| JP | 2008078362 | 4/2008 |
| WO | 2001039234 | 5/2001 |
| WO | 2002002714 | 1/2002 |
| WO | 200215645 | 2/2002 |
| WO | 2003040257 | 5/2003 |
| WO | 2003060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2007/029798 | 9/2006 |
| WO | 2006098120 | 9/2006 |
| WO | 2006100298 | 9/2006 |
| WO | 2006103874 | 10/2006 |
| WO | 2006114966 | 11/2006 |
| WO | 2006/12880 | 12/2006 |
| WO | 2006132173 | 12/2006 |
| WO | 2007002683 | 1/2007 |
| WO | 2007004380 | 1/2007 |
| WO | 2007/069569 | 6/2007 |
| WO | 2007063754 | 6/2007 |
| WO | 2007063796 | 6/2007 |
| WO | 2007/077810 | 7/2007 |
| WO | 2007/238500 | 9/2007 |
| WO | 2008056746 | 5/2008 |

(56) References Cited

FOREIGN PATENT DOCUMENTS

| WO | 2008101842 | 8/2008 |
|---|---|---|
| WO | 2008132085 | 11/2008 |
| WO | 2009000673 | 12/2008 |
| WO | 2009/008099 | 1/2009 |
| WO | 2009/008100 | 1/2009 |
| WO | 2009003898 | 1/2009 |
| WO | 2009008311 | 1/2009 |
| WO | 2009018009 | 2/2009 |
| WO | 2009/030981 | 3/2009 |
| WO | 2009050290 | 4/2009 |
| WO | 2009/060742 | 5/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |

OTHER PUBLICATIONS

Tsai, et al., "3-(9-Carbazolyl)carbazoles and 3,6-Di(9-carbazolyl)carbazoles as effective host materials for efficient blue organic electrophosphorescence" Adv. Mater. 2007, 19, 862-866.
Adachi, Chihaya et al., "Organic Electroluminescent Device Having a Hole Conductor as an Emitting Layer," Appl. Phys. Lett., 55(15): 1489-1491 (1989).
Adachi, Chihaya et al., Appl. Phys., "Neary 100% Internal Phosphoescence Efficiency in an Oganic Light Emitting Device," J. Appl. Phys., 90(10): 5048-5051 (2001).
Adachi, Chihaya et al., "High-Efficiency Red Electrophosphorescence Devices," Appl. Phys. Lett., 78(11)1622-1624.
Aonuma, Masaki et al., "Material Design of Hole Transport Materials Capable of Thick-Film Formation in Organic Light Emitting Diodes," Appl. Phys. Lett., 90:183503-1-183503-3.
Baldo et al, Highly Efficient Phosphorescent Emission from Organic Electroluminescent Devices, Nature, vol. 395, 151-154, (1998).
Baldo et al., Very high-efficiency green organic light-emitting devices based on electrophosphorescence, Appl. Phys. Lett., vol. 75, No. 3, 4-6 (1999).
Gao, Zhigiang et al., "Bright-Blue Electroluminescence From a Silyl-Substituted ter-(phenyiene-vinylene) derivative." Appl. Phys. Lett., 74(6): 865-867 (1999).
Guo, Tzung-Fang et al., "Highly Efficient Electrophosphorescent Polymer Light-Emitting Devices," Organic Electronics, 115-20 (2000).
Hamada, Yuji et al., "High Luminance in Organic Electroluminescent Devices with Bis(10-hydroxybenzo[h]quinolinato)" Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsona et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Kai, Masarnichi and Tokito, Shizuo, "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37 923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido J. Junji et al., 1,2,4-Triazole Derivatve as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4''-Tri(N-carbazolyl)triphenylamine (TCTA) and 4,4',4''-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett, 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18 (21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota, Yasuhiko, "5,5'-Bis(dimesitylboryl)-2,2'-bithiophene and 5,5''-Bis (dimesitylboryl)-2,2'5',2''-terthiophene as a Novel Family of Electron-Transporting Amorphous Molecular Materials,"J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al. "Realizing Green Phosphorescent Light-Emitting Materials from Rhenium(I) Pyrazolato Diimine Complexes," Inorg. Chem., 42(4):1248-1255 (2003).
Sakamoto Youichi , "Synthesis, Characterization, and Electron-Transport Property of Perfluorinated Phenylene Dendimers," J. Am. Chem. Soc., 122(8):1832-1833 (2000).
Salbeck, J. et al., "Low (1997) Molecular Organic Glasses for Blue Electroluminescence," Synthetic Metals, 91209-215 (1997).
Shirota, Yasuhiko et al., "Starburst Molecules Based on p-Electron Systems as Materials for Organic Electroluminescent Devices," Journal of Luminescence, 72-74:985-991 (1997).

(56) References Cited

OTHER PUBLICATIONS

Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-15350-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes of Poly(3-Hexylthiophene) Electro-Optical Characterisitics Related to Structure," Synthethic Metals, 87:171-177 (1997).

Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).

Tang, C.W, and VanSLYKE, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

Van Slyke, S. A. et al., "Organic Electroluminescent Devices with Improved Stability," Appl. Phys. Lett., 69 (15):2160-2162 (1996).

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

DIBENZOTHIOPHENE-CONTAINING MATERIALS IN PHOSPHORESCENT LIGHT EMITTING DIODES

CROSS-REFERENCE TO RELATED APPLICATIONS

This application is a divisional of U.S. application Ser. No. 13/186,204, filed Jul. 19, 2011, which is a divisional of U.S. application Ser. No. 12/208,907, filed Sep. 11, 2008, which issued as U.S. Pat. No. 8,007,927 on Aug. 30, 2011, which claims priority to U.S. Provisional Application Ser. No. 61/017,480, filed Dec. 28, 2007, the disclosures of which are herein expressly incorporated by reference in their entirety. This application is also related to International Application No. PCT/IB2007/004687, filed Dec. 28, 2007.

PARTIES TO A JOINT RESEARCH AGREEMENT

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention is directed to organic light emitting devices (OLEDs). More specifically, the present invention relates to phosphorescent light emitting materials and devices that may have improved device lifetime.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the structure of Formula I:

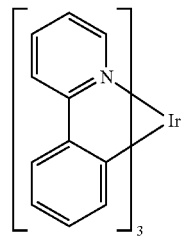

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

A new type of materials is provided. The new class of materials has a dibenzothiophene-containing compound selected from the group consisting of:

Compound 1G

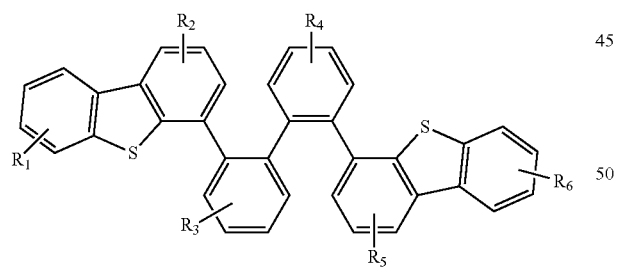

Compound 2G

Compound 3G

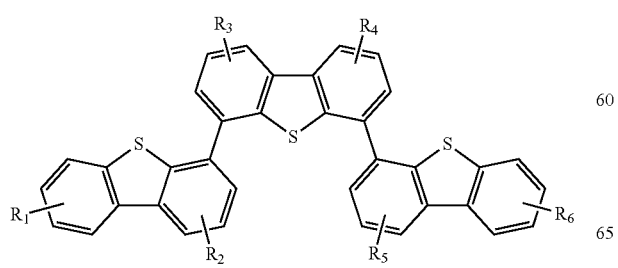

-continued

Compound 4G

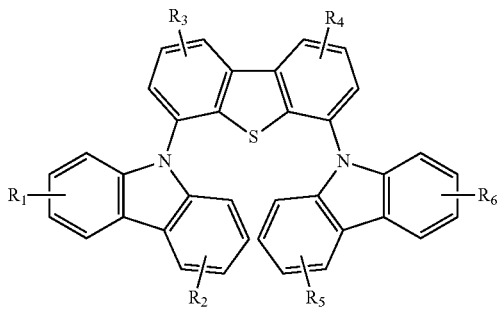

Compound 5G

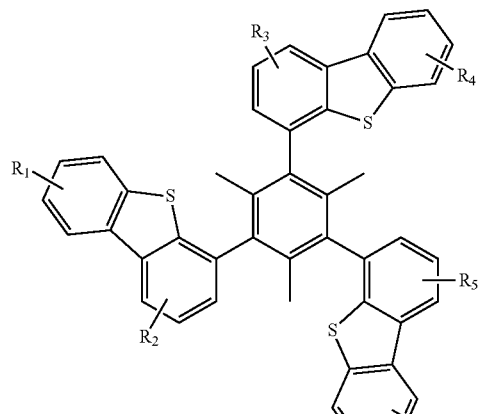

Compound 6G

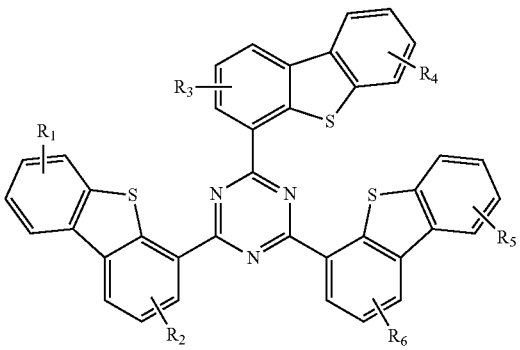

Compound 7G

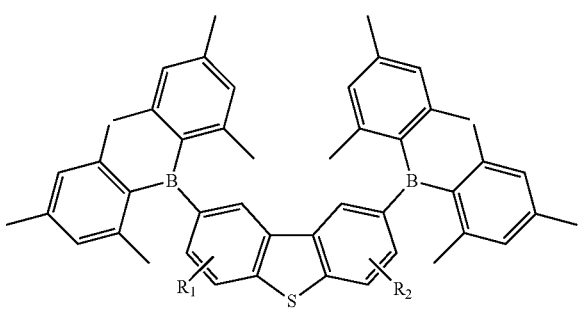

-continued

Compound 8G

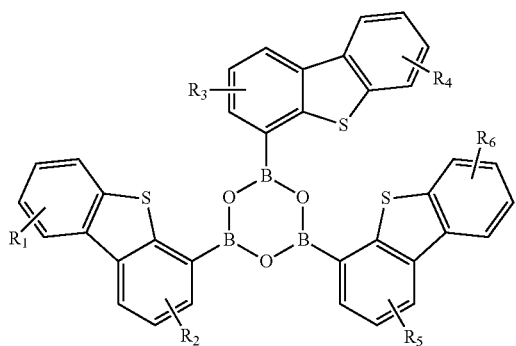

Compound 9G

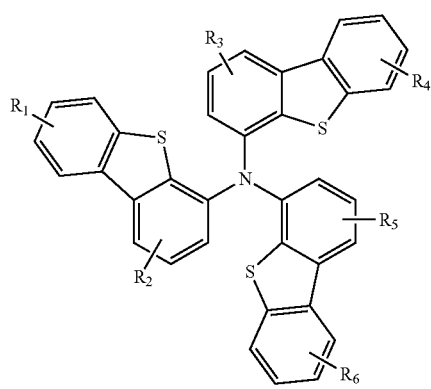

Compound 10G

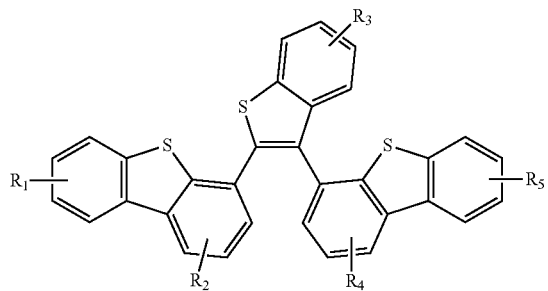

Compound 11G

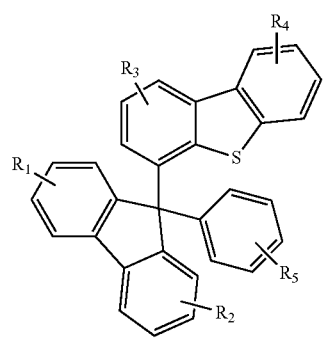

-continued

Compound 12G

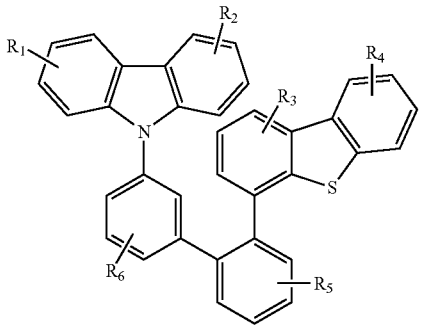

where each of $R_1$ through $R_6$ are independently selected from the group consisting of any aryl and alkyl substituents and H, and where each of $R_1$ through $R_6$ may represent multiple substitutions. In one aspect, all of $R_1$ through $R_6$ are H.

An organic light emitting device is also provided. The device has an anode, a cathode, an and an organic layer disposed between the anode and the cathode. The organic layer further comprises a material containing a compound from the group consisting of Compound 1G through 12G, as described above, with or without substituents. Preferably the organic layer is an emissive layer having a host and an emissive dopant, and the compound is the host. The compound may also preferably be used as a material in an enhancement layer.

New materials are provided. The materials have a dibenzothiophene-containing and/or dibenzofuran-containing compound selected from the group consisting of:

Compound 2G

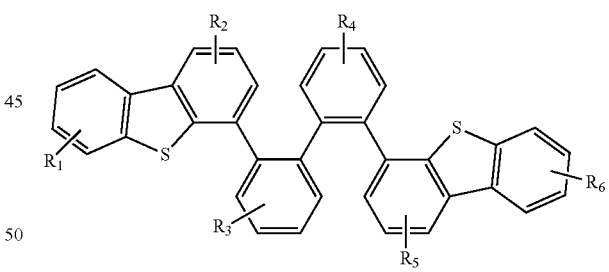

Compound 3G

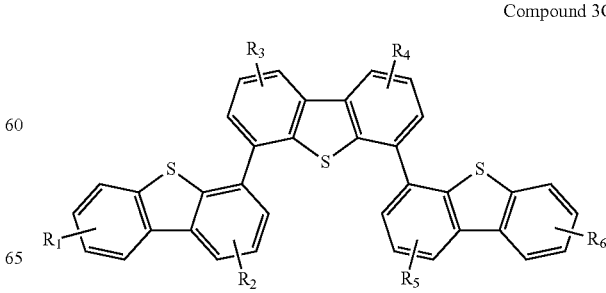

Compound 4G
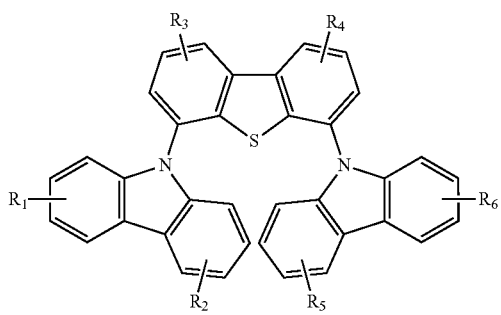
Compound 8G
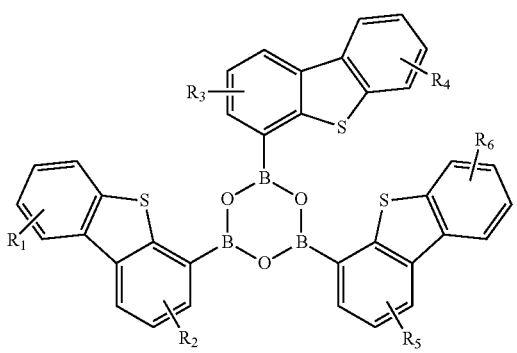
Compound 5G
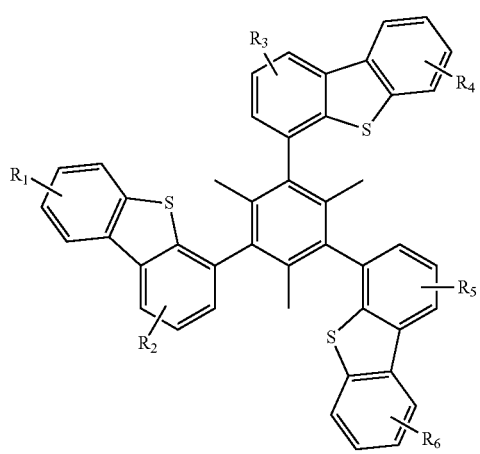
Compound 9G
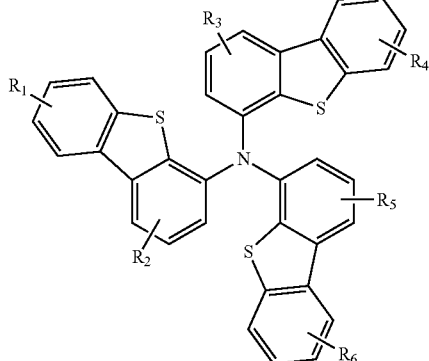
Compound 6G
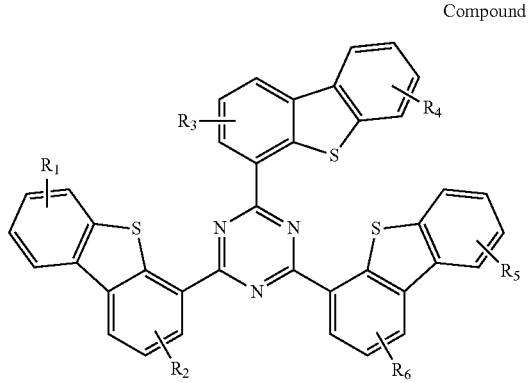
Compound 10G
Compound 7G
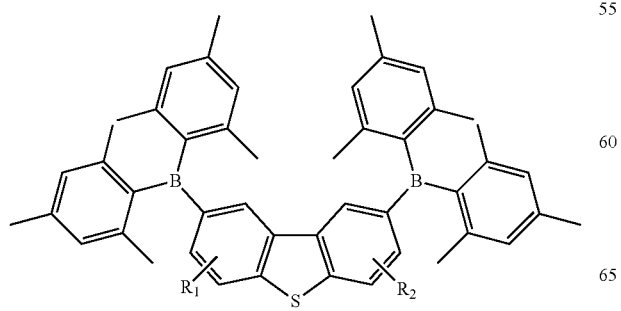
Compound 11G
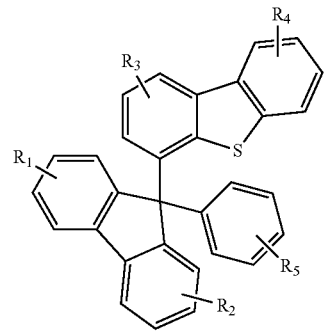

Compound 12G
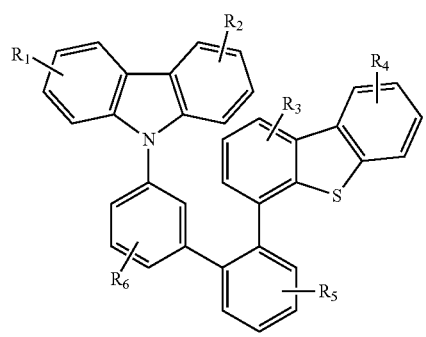
Compound 13G
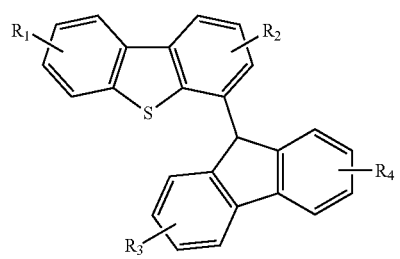
Compound 14G
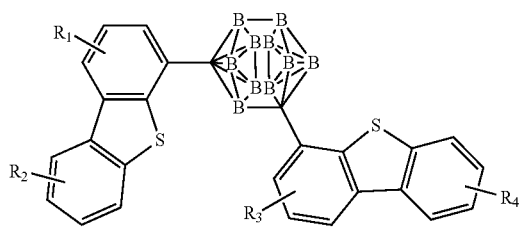
Compound 15G
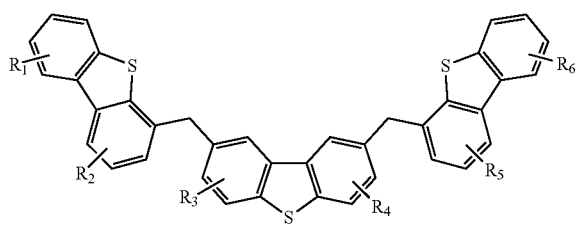
Compound 16G
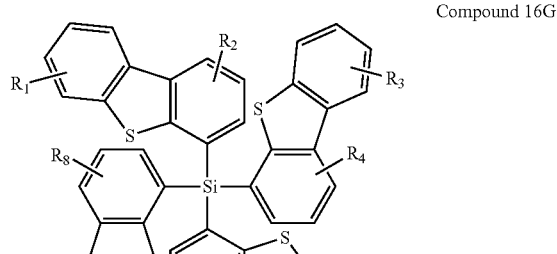
Compound 17G
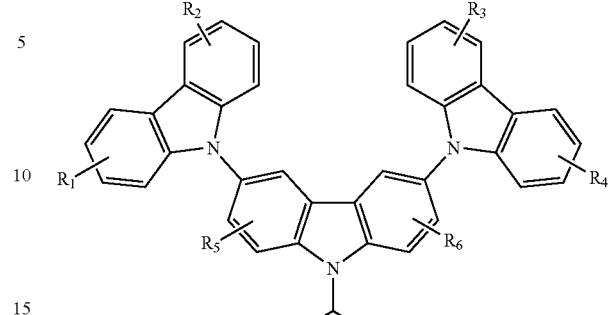
Compound 18G
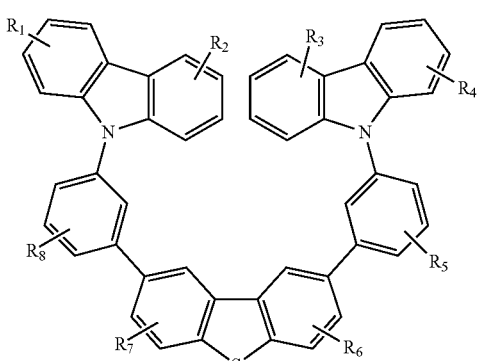
Compound 19G
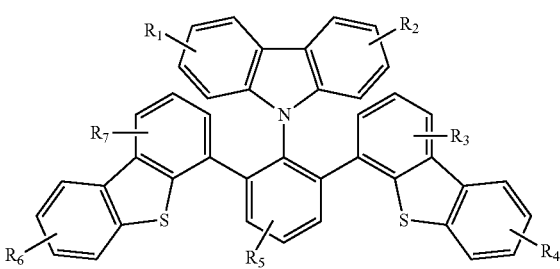
Compound 20G
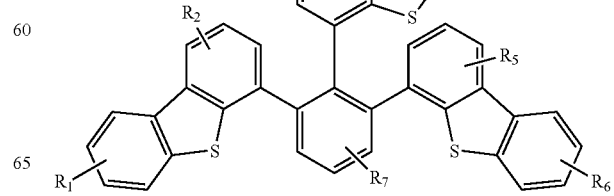

Compound 21G
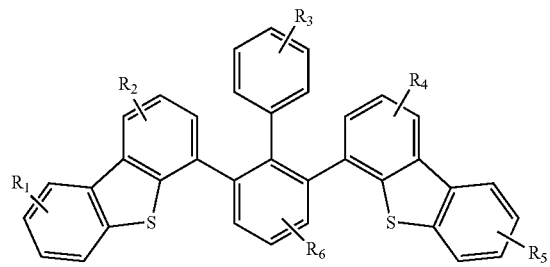
Compound 22G
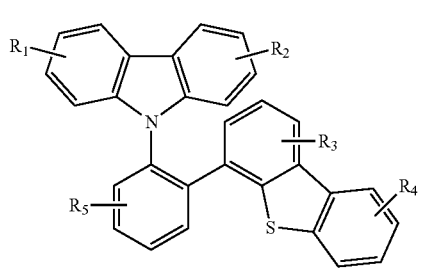
Compound 23G
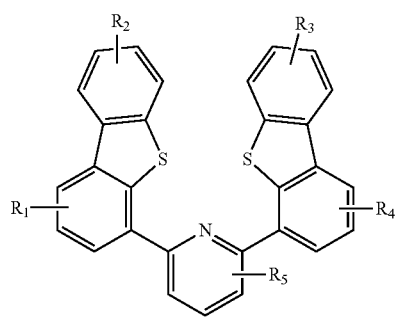
Compound 24G
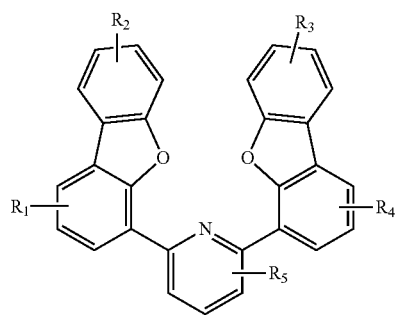
Compound 25G
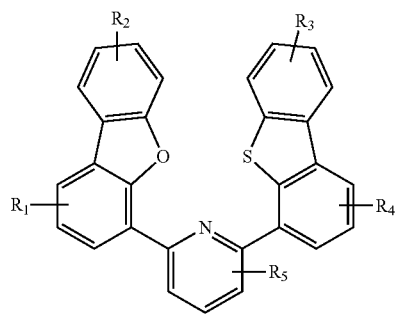
Compound 26G
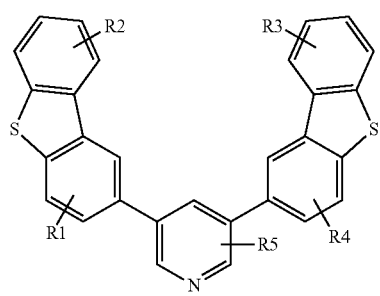
Compound 27G
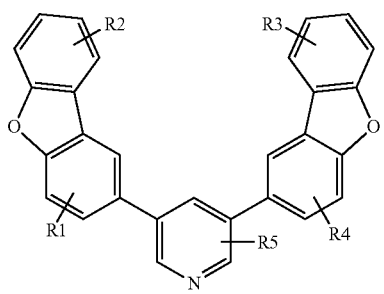
Compound 28G
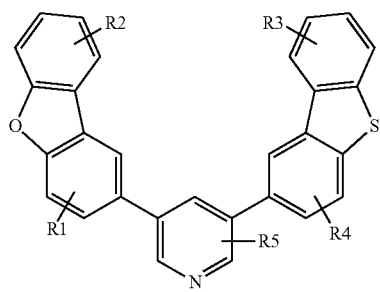
Compound 29G
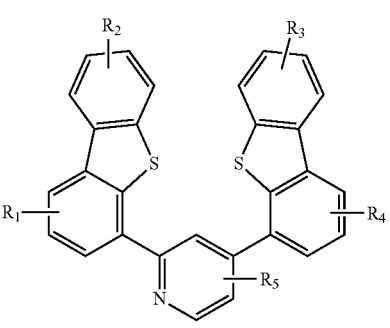
Compound 30G
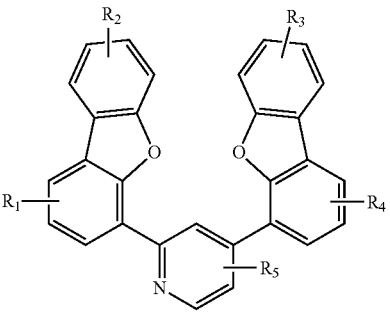

Compound 31G

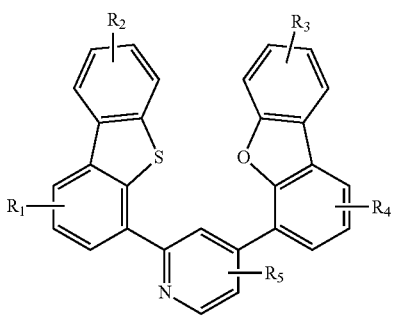

Compound 32G

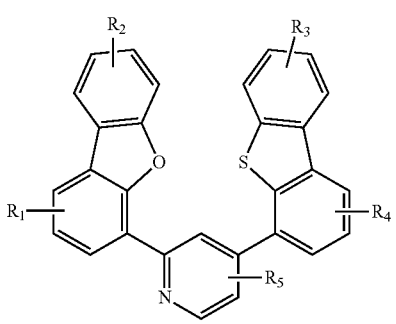

Compound 33G

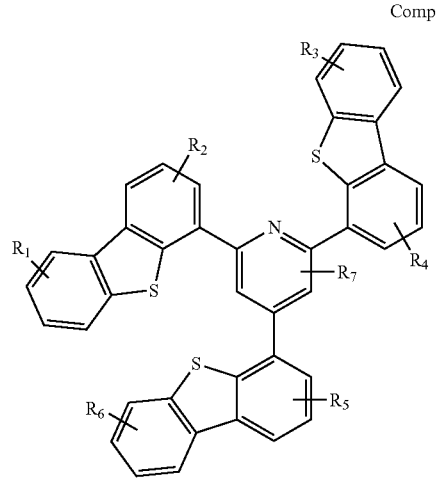

Compound 34G

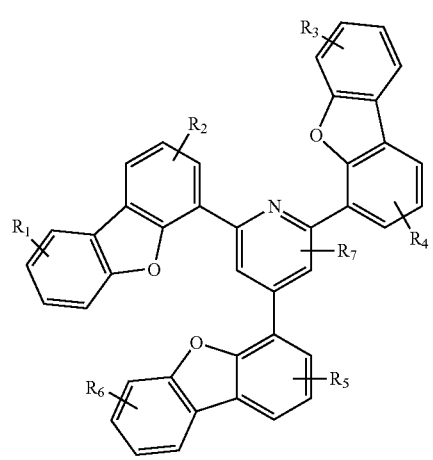

Compound 35G

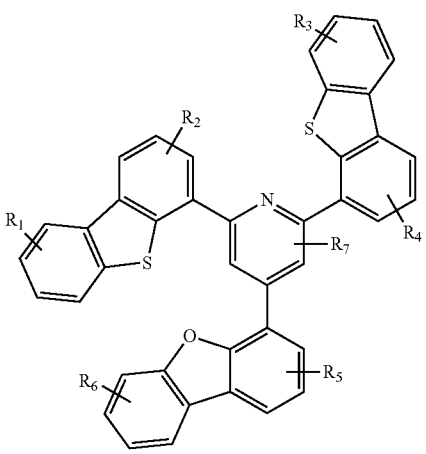

where each of $R_1$ through $R_8$ are independently selected from the group consisting of any aryl and alkyl substituents and H, and where each of $R_1$ through $R_8$ may represent multiple substitutions. In one aspect, all of $R_1$ through $R_8$ are H.

An organic light emitting device is also provided. The device has an anode, a cathode, and an organic layer disposed between the anode and the cathode. The organic layer further comprises a material containing a compound from the group consisting of Compound 2G through 35G, as described above, with or without substituents. Preferably the organic layer is an emissive layer having a host and an emissive dopant, and the compound is the host. The compound may also preferably be used as a material in an enhancement layer.

A consumer product is also provided. The product contains a device that has an anode, a cathode, and an organic layer disposed between the anode and the cathode, where the organic layer further comprises a material containing a compound from the group consisting of Compounds 2G through 35G, as described above, with or without substituents.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
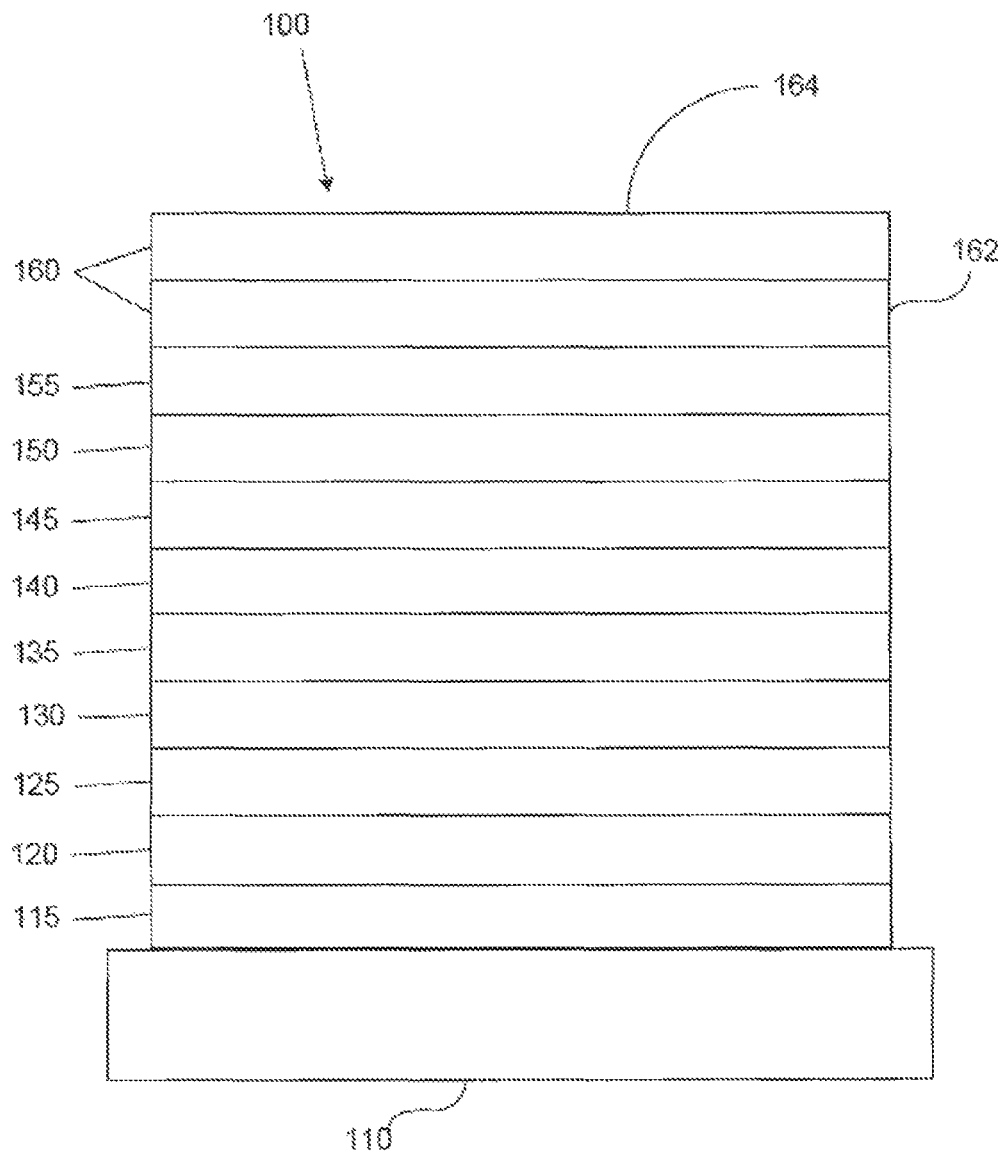
FIG. 1 shows an organic light emitting device.

FIG. 1 shows an organic light emitting device 100. The figures are not necessarily drawn to scale. Device 100 may include a substrate 110, an anode 115, a hole injection layer 120 (HIL), a hole transport layer 125 (HTL), an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety. An "enhancement layer" occupies the same position in a device as a blocking layer described above, and may have blocking functionality or other functionality that improves device performance.

Figure 2:
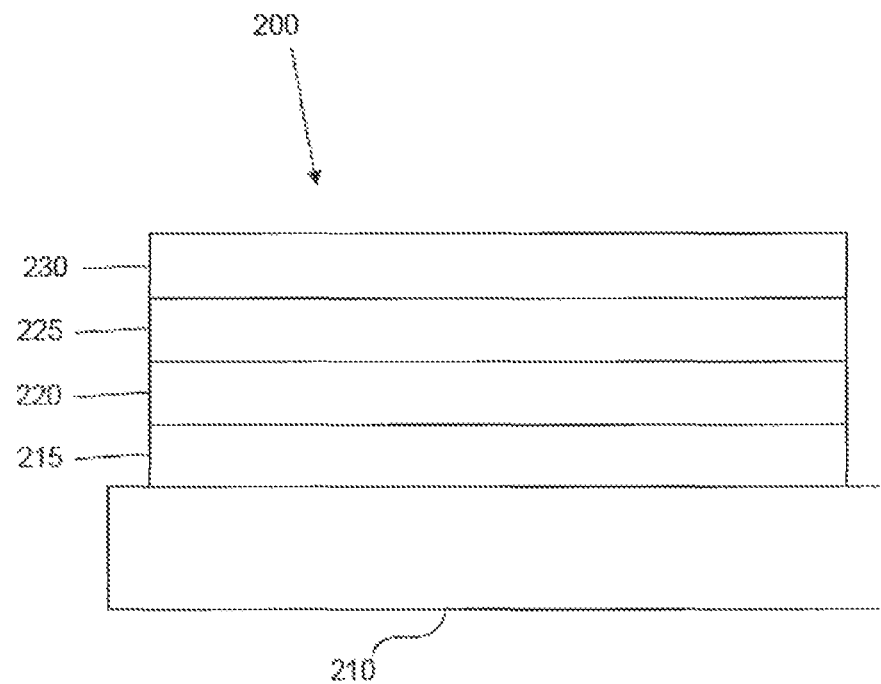
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Dibenzo[b,d]thiophene (also referred to herein as "dibenzothiophene")-containing materials are provided, which can be used in the PHOLED devices fabricated by both vapor deposition or solution processing, giving long lifetime stable devices with low voltage. The materials may be used as a stable host in PHOLED devices, or in other layers, such as an enhancement layer.

Compounds are provided comprising dibenzothiophene and/or dibenzofuran. Dibenzothiophenes and dibenzofurans may be used as hole and/or electron transporting organic conductors, they usually exhibit more reversible electrochemical reduction in solution than some common organic groups, such as biphenyl. The triplet energies of dibenzothiophenes and dibenzofurans are relatively high. Therefore, a compound containing dibenzothiophene and/or dibenzofuran may be advantageously used as a host or a material for an enhancement layer in PHOLED devices. For example, the triplet energy of dibenzothiophene is high enough for use in a blue or green PHOLED device. Dibenzothiophene and/or dibenzofuran-containing compounds may provide improved device stability while maintaining good device efficiency.

Dibenzothiophene-containing materials may have the following general structure:

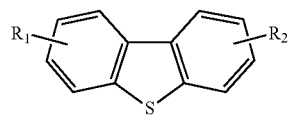

Each of $R_1$ and $R_2$ may be independently selected from the group consisting of any alkyl, alkoxy, amino, alkenyl, alkynyl, arylkyl, aryl, heteroaryl, and hydrogen, and where $R_1$ and $R_2$ may represent multiple substitutions.

Particular dibenzothiophene compounds are provided, which may be advantageously used in OLEDs, having the following structures:

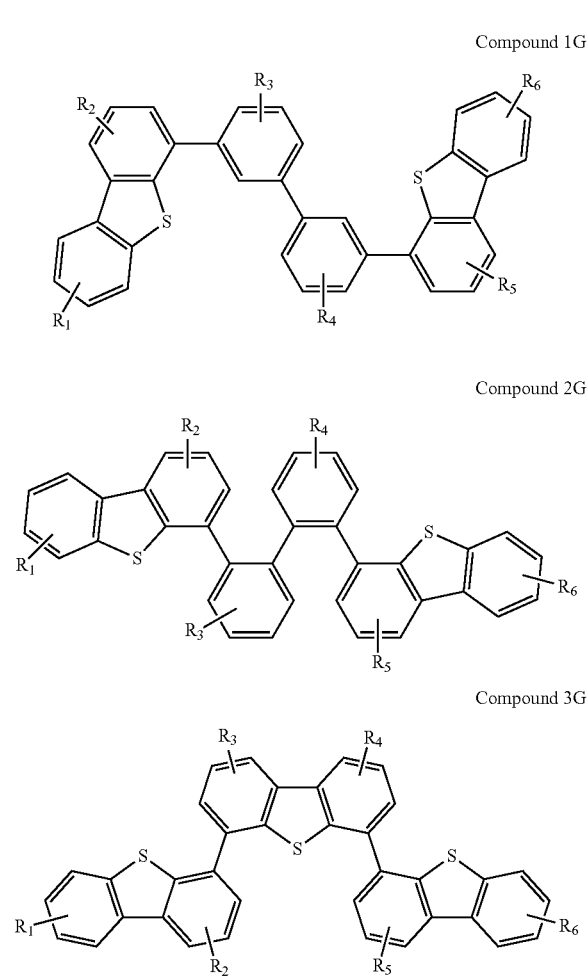

Compound 4G
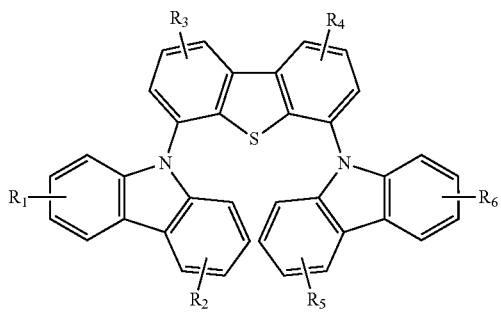
Compound 5G
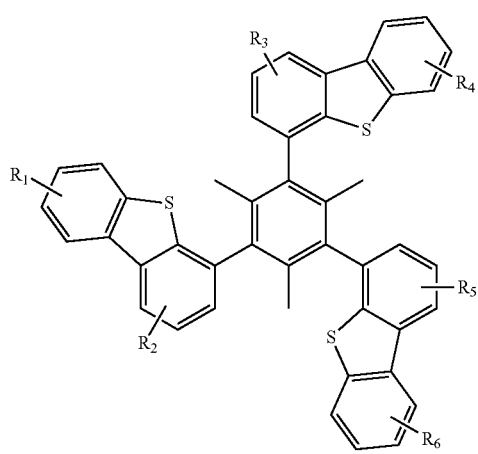
Compound 6G
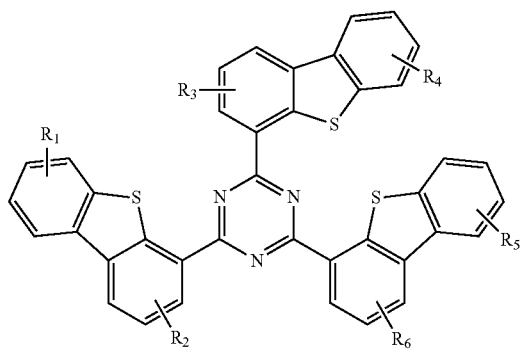
Compound 7G
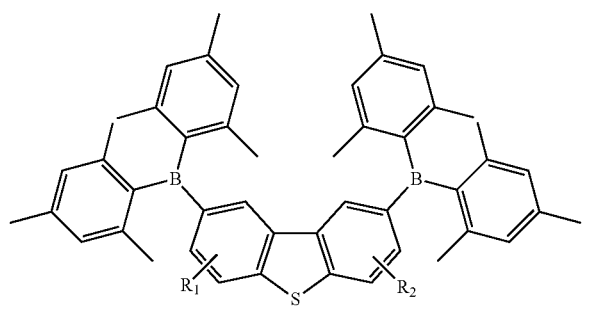
Compound 8G
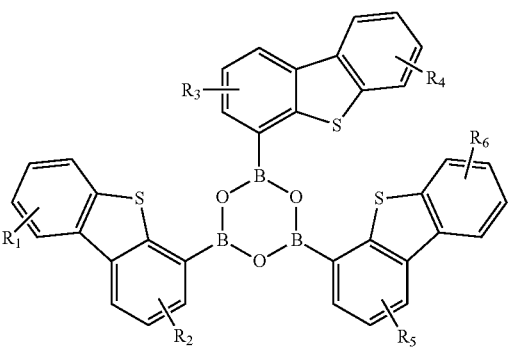
Compound 9G
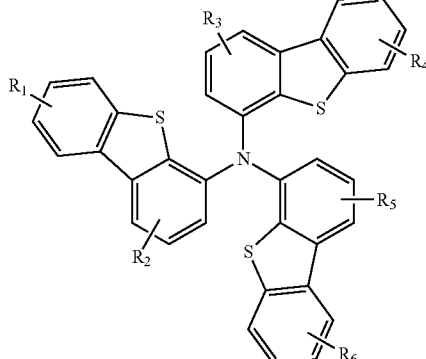
Compound 10G
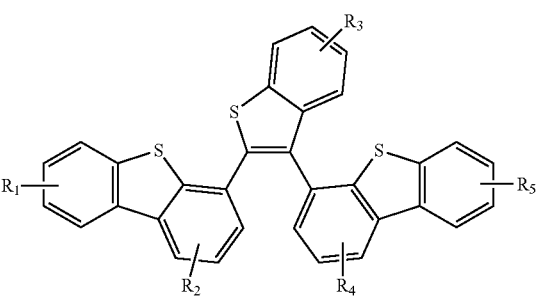
Compound 11G
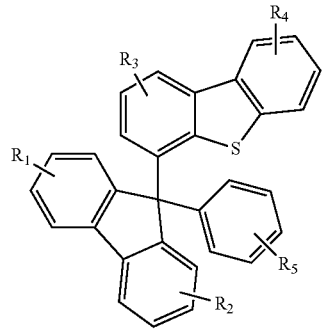

-continued

Compound 12G

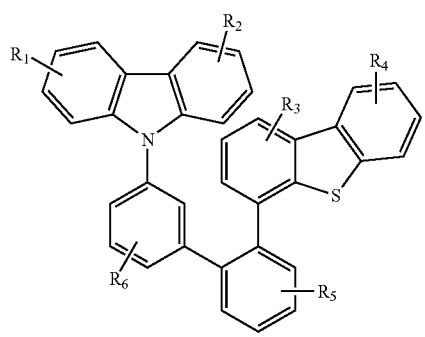

Each of $R_1$ through $R_6$ are independently selected from the group consisting of any alkyl, alkoxy, amino, alkenyl, alkynyl, arylkyl, aryl, heteroaryl, and hydrogen, and where each of $R_1$ through $R_6$ may represent multiple substitutions.

Additionally, particular dibenzothiophene-containing compounds, which may be advantageously used in OLEDs, are provided:

Compound 1

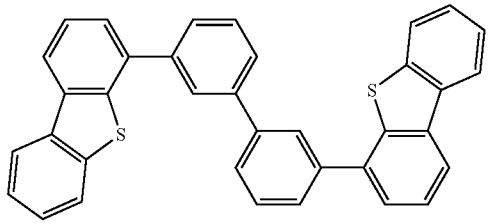

Compound 2

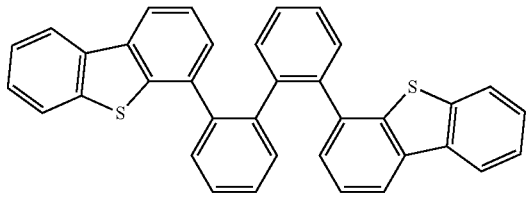

Compound 3

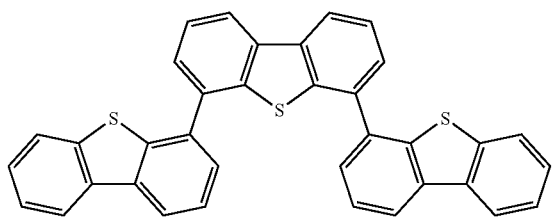

Compound 4

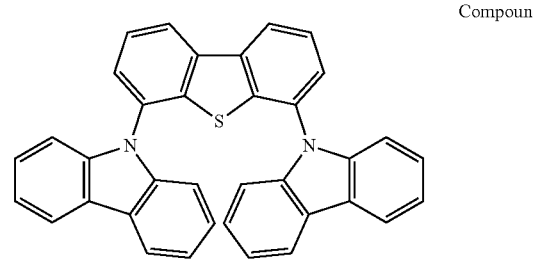

-continued

Compound 5

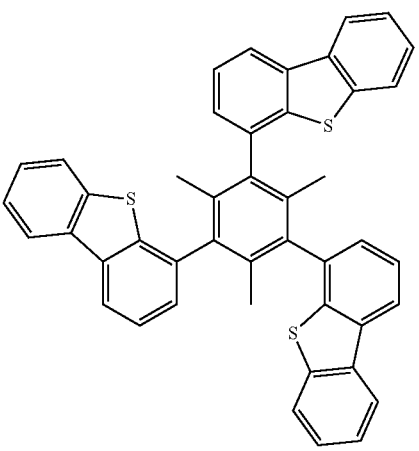

Compound 6

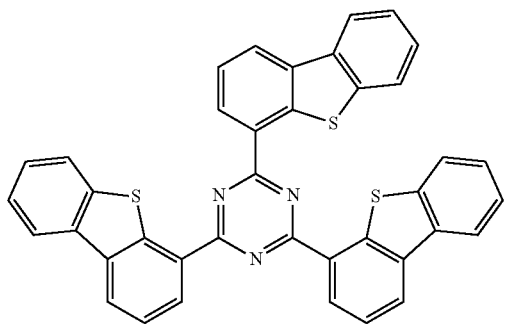

Compound 7

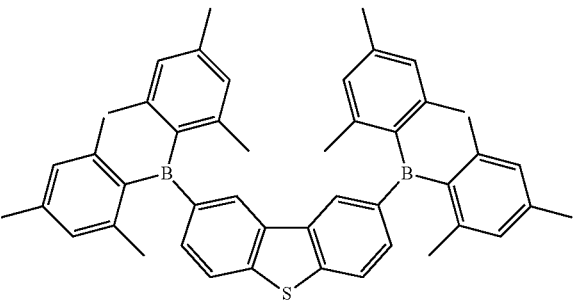

Compound 8

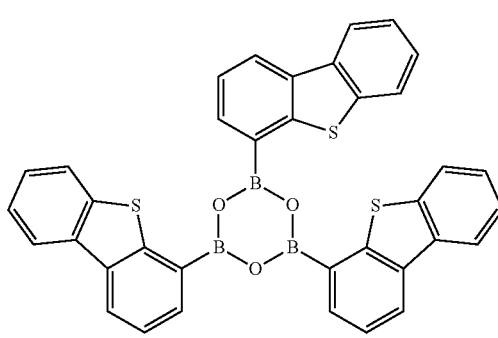

Compound 9
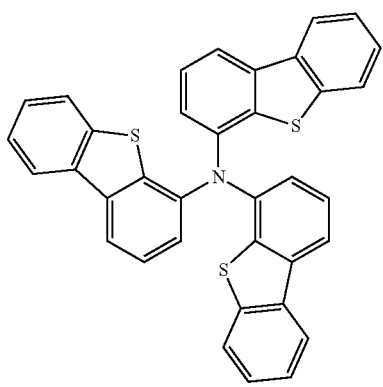
Compound 2G
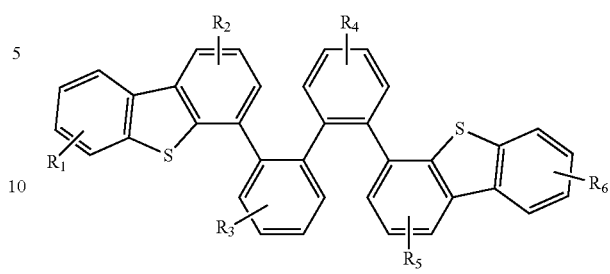
Compound 10
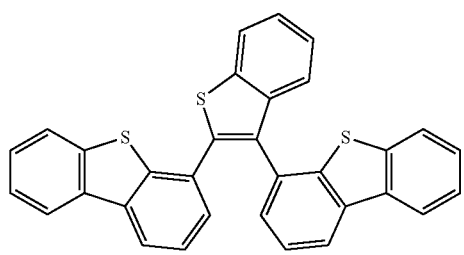
Compound 3G
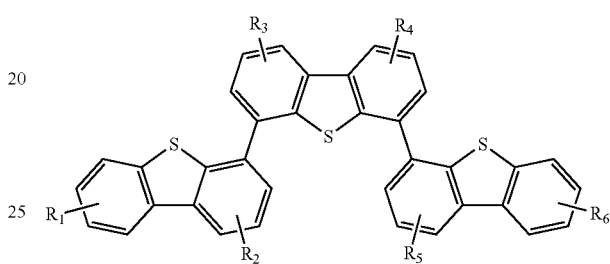
Compound 11
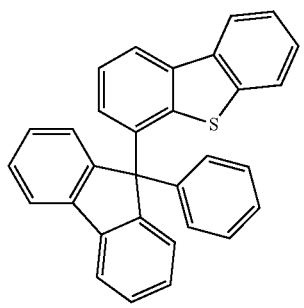
Compound 4G
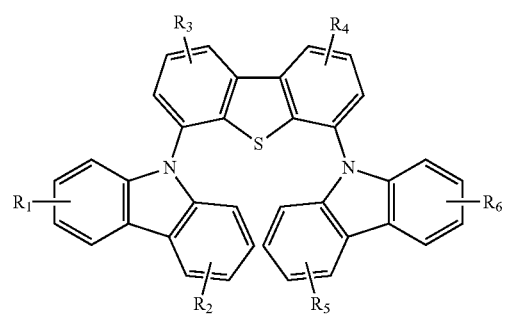
Compound 12
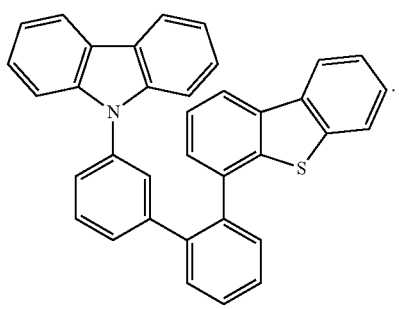
Compound 5G
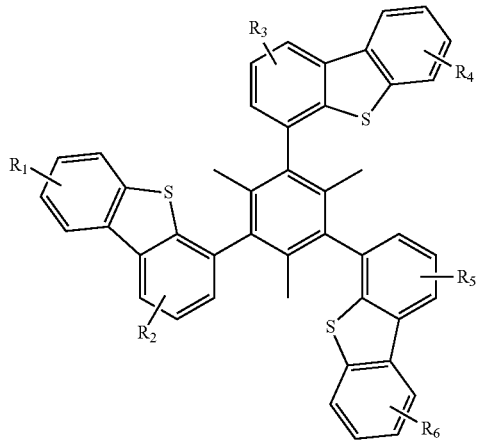
Dibenzothiophene-containing and/or dibenzofuran-containing compounds are provided, which may be advantageously used in OLEDs, having the following structures:

Compound 6G
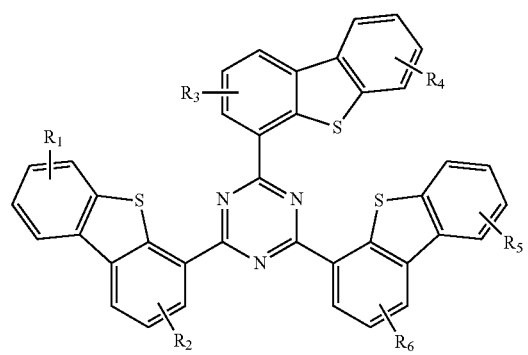
Compound 7G
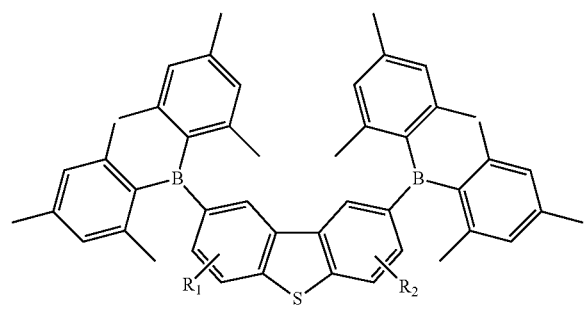
Compound 8G
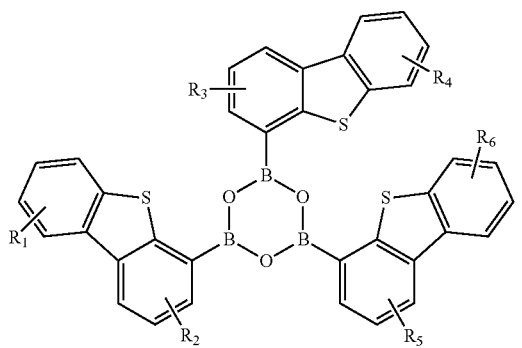
Compound 9G
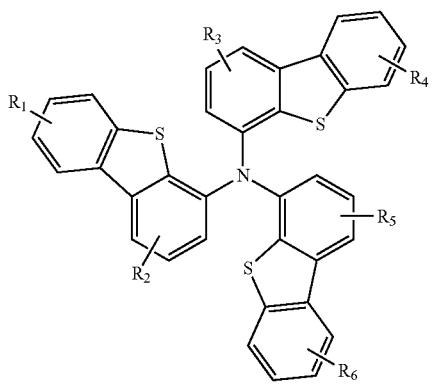
Compound 10G
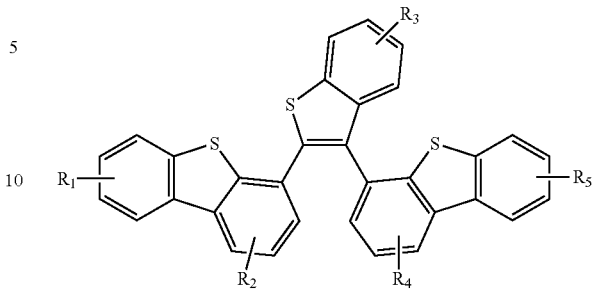
Compound 11G
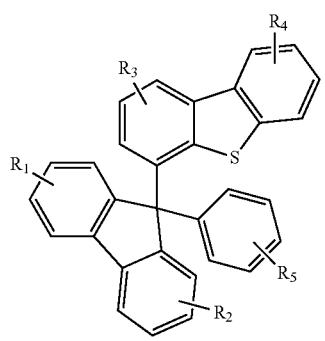
Compound 12G
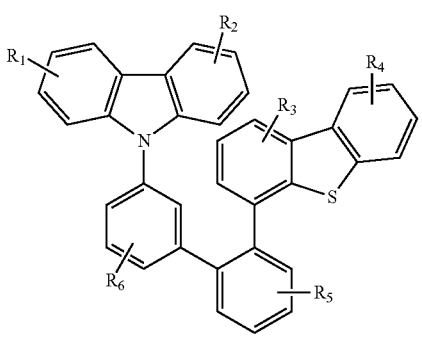
Compound 13G
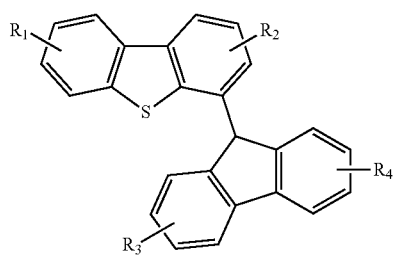
Compound 14G
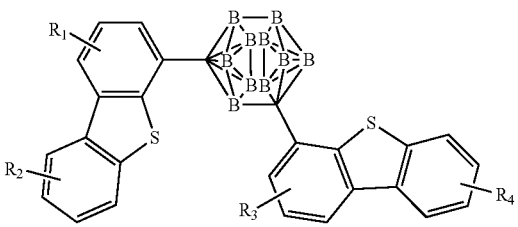

Compound 15G
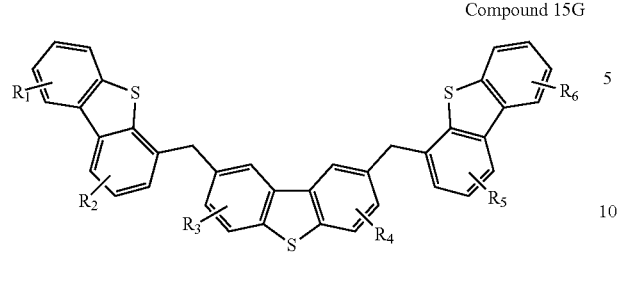
Compound 16G
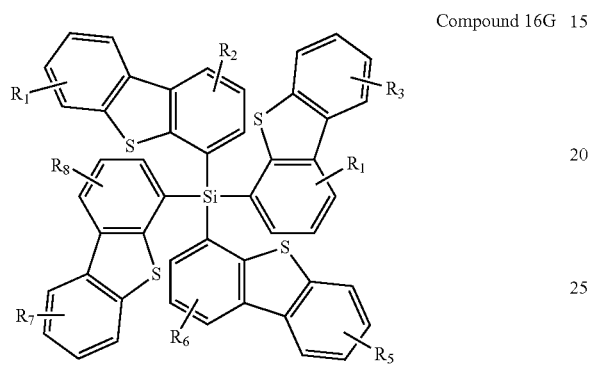
Compound 17G
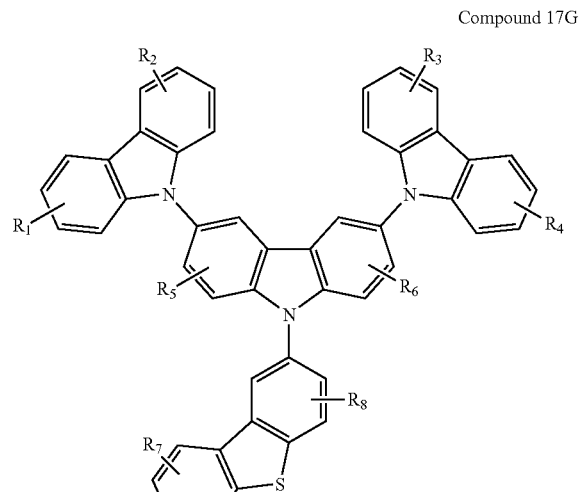
Compound 18G
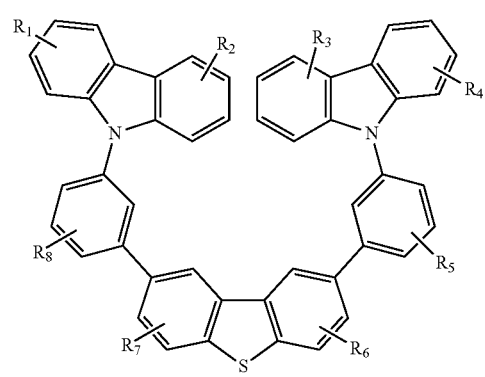
Compound 19G
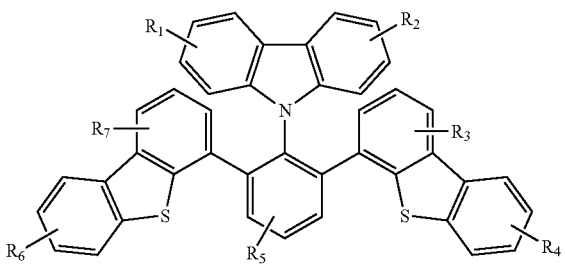
Compound 20G
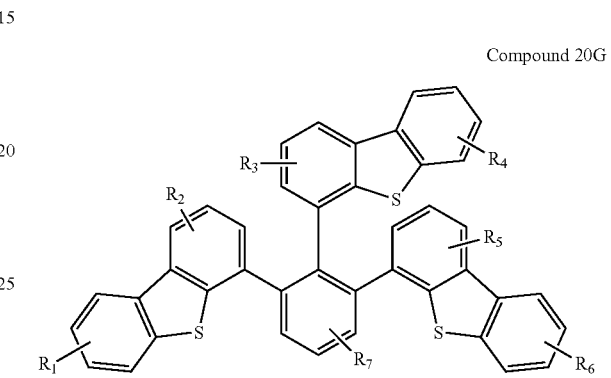
Compound 21G
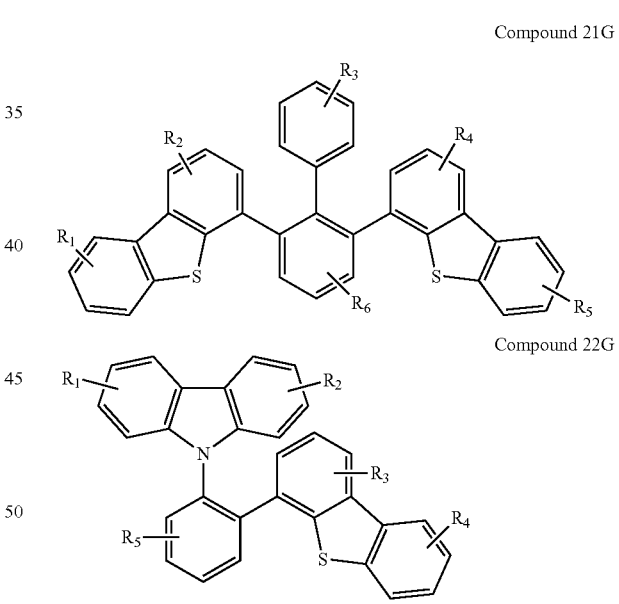
Compound 22G
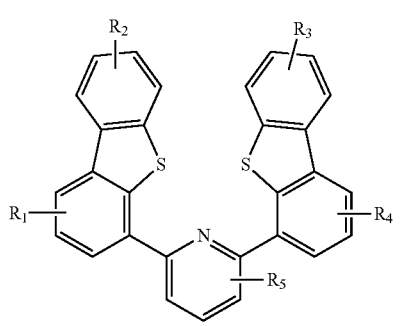
Compound 23G
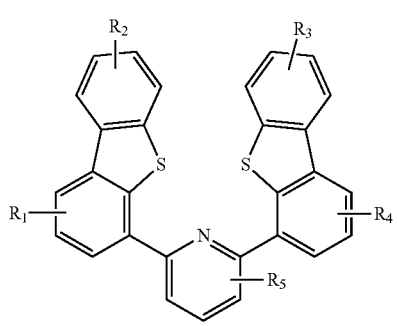

Compound 24G
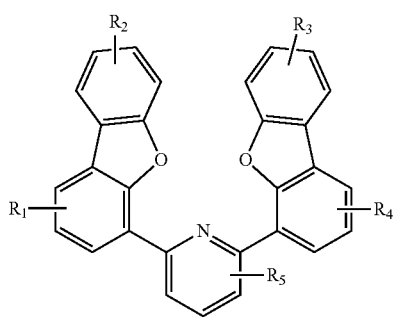
Compound 25G
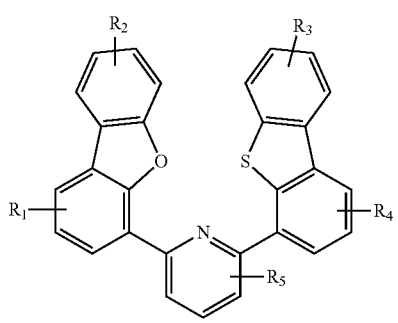
Compound 26G
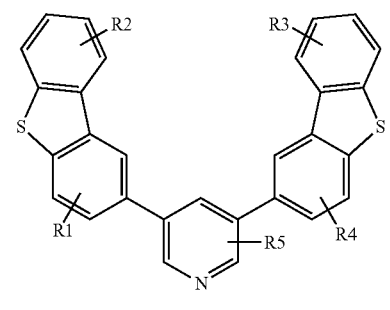
Compound 27G
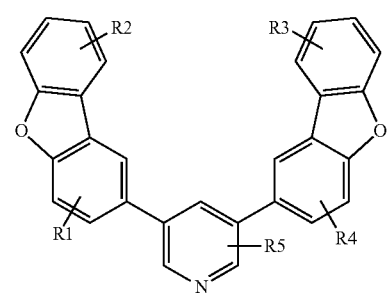
Compound 28G
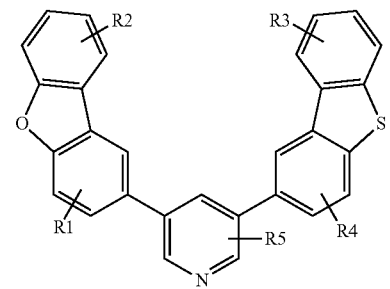
Compound 29G
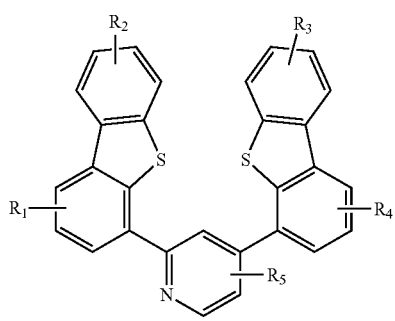
Compound 30G
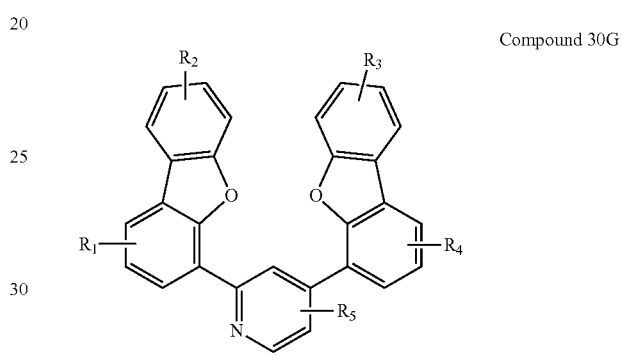
Compound 31G
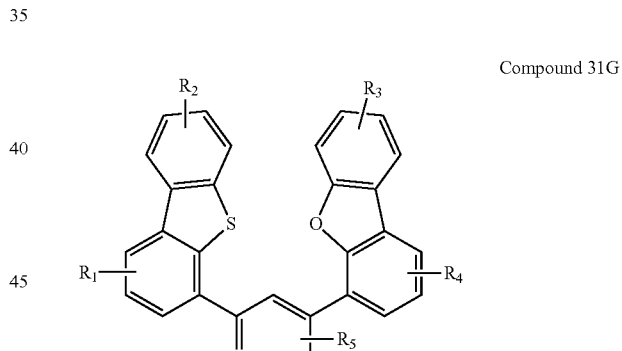
Compound 32G
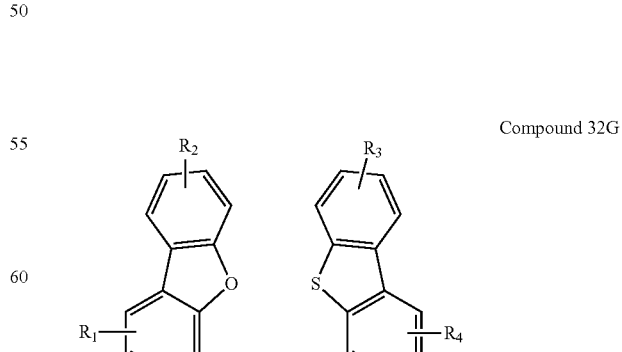

-continued

Compound 33G

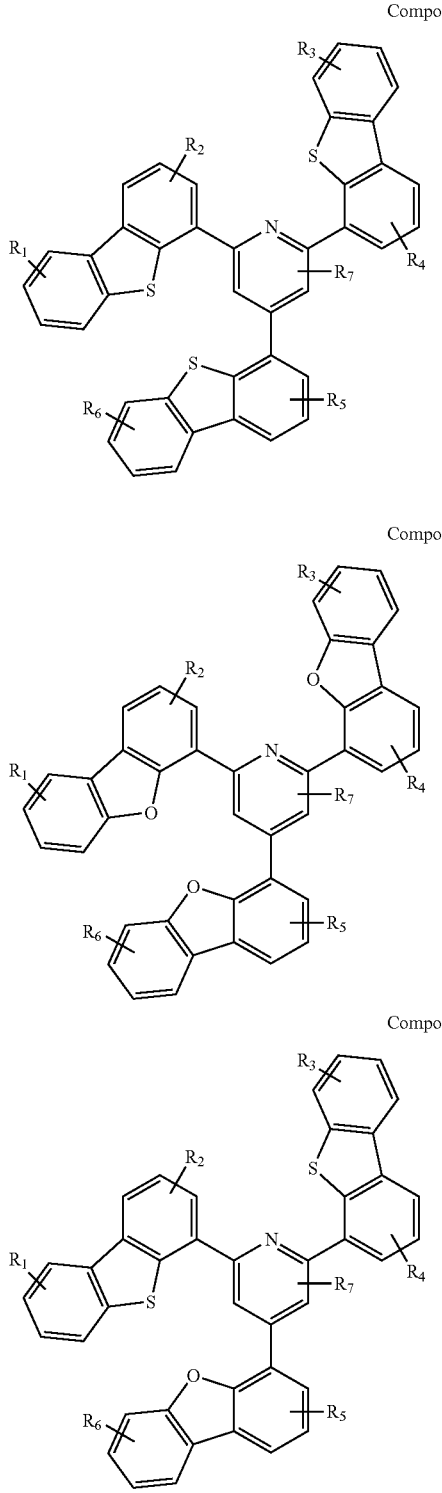

Compound 34G

Compound 35G

Each of $R_1$ through $R_8$ are independently selected from the group consisting of any alkyl, alkoxy, amino, alkenyl, alkynyl, arylkyl, aryl, heteroaryl, and hydrogen, and where each of $R_1$ through $R_8$ may represent multiple substitutions.

Additionally, dibenzothiophene-containing and/or dibenzofuran-containing compounds are provided, which may be advantageously used in OLEDs, are provided:

Compound 2

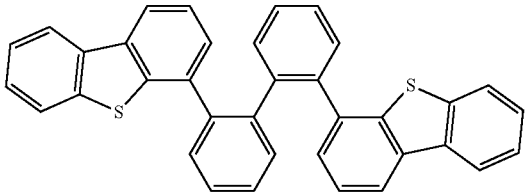

Compound 3

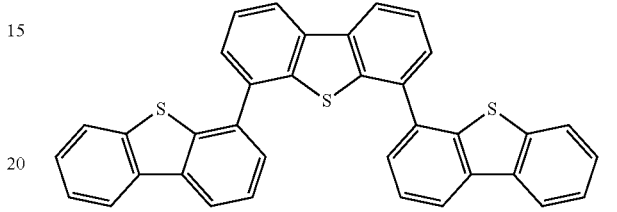

Compound 4

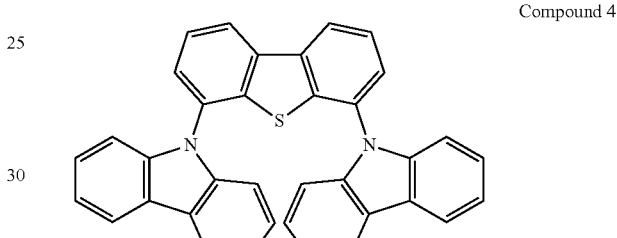

Compound 5

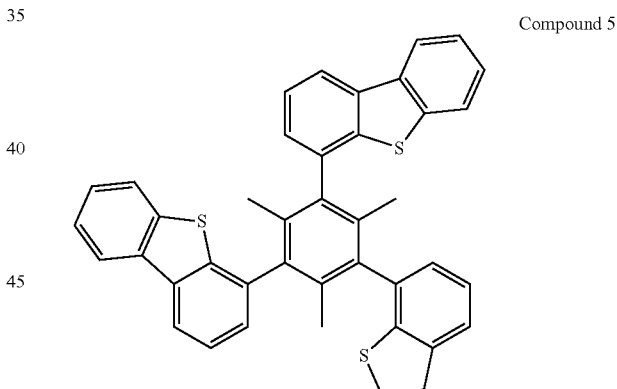

Compound 6

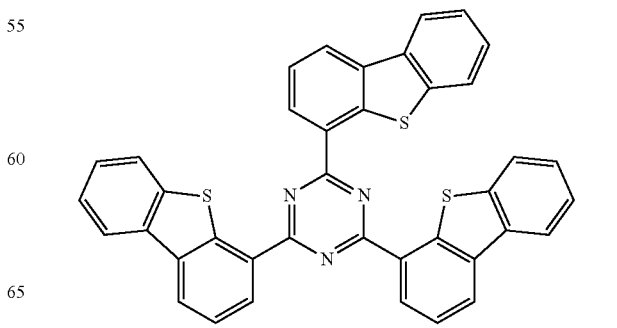

Compound 7
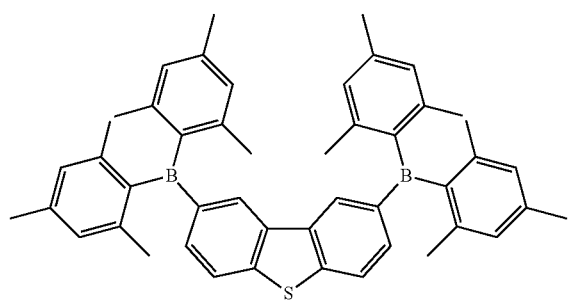
Compound 8
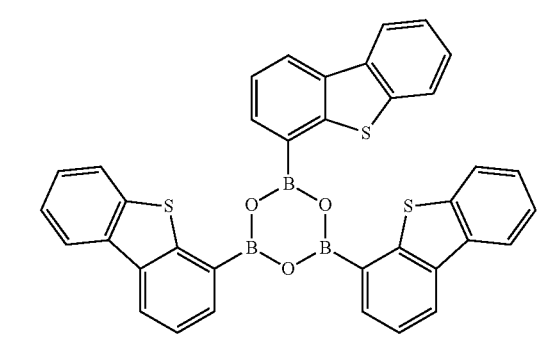
Compound 9
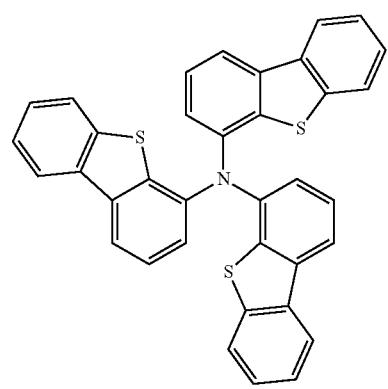
Compound 10
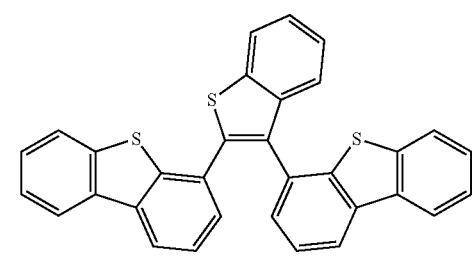
Compound 11
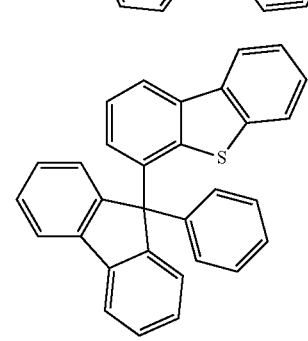
Compound 12
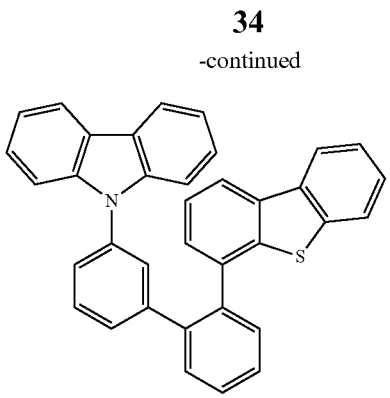
Compound 13
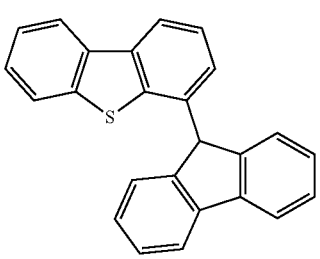
Compound 14
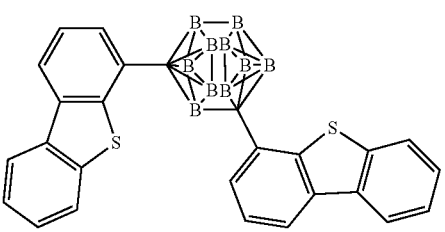
Compound 15
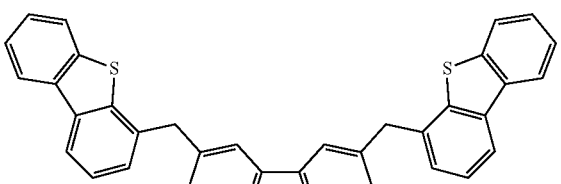
Compound 16
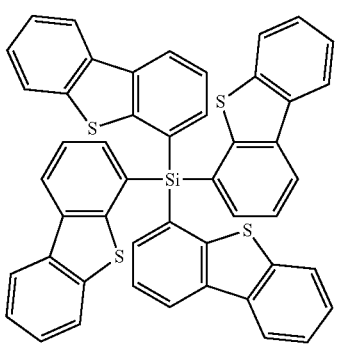

Compound 17
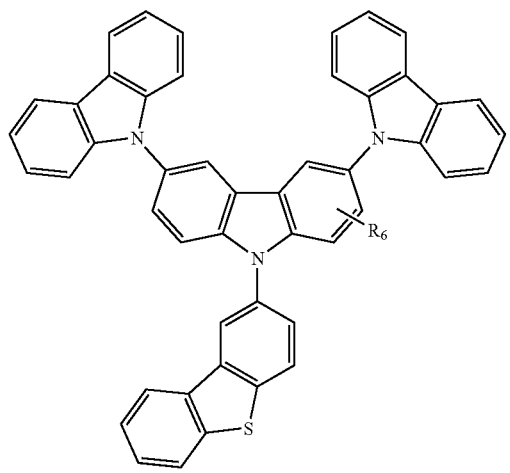
Compound 18
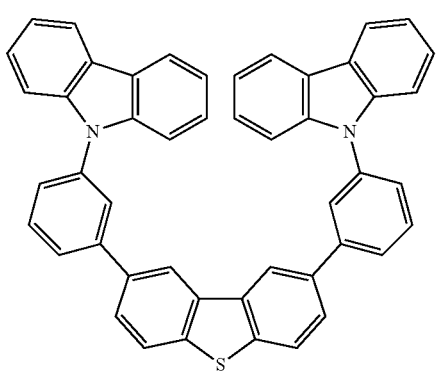
Compound 19
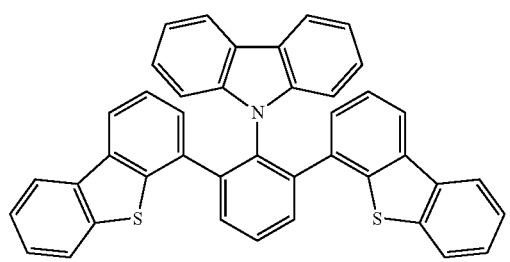
Compound 20
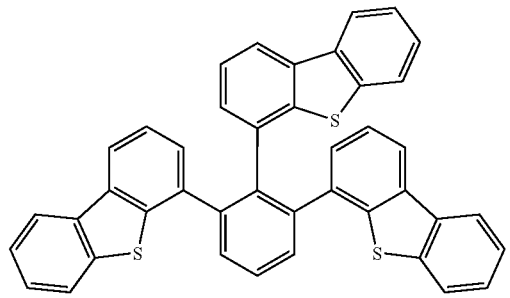
Compound 21
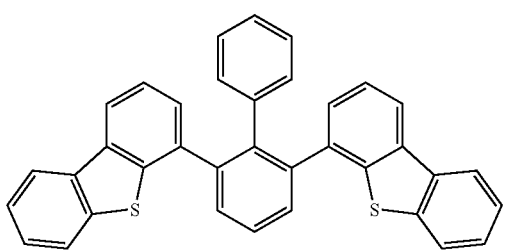
Compound 22
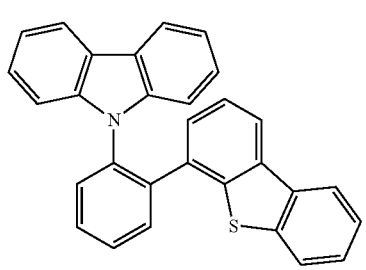
Compound 23
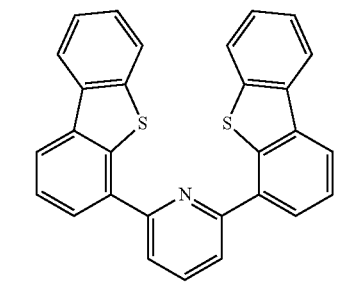
Compound 24
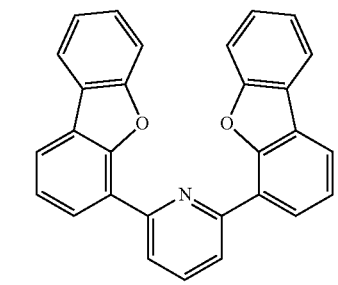
Compound 25
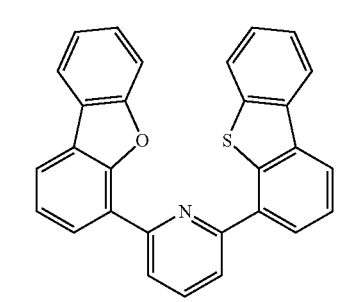

Compound 26
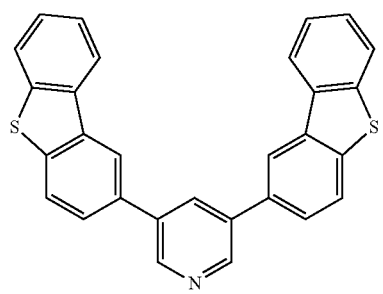
Compound 27
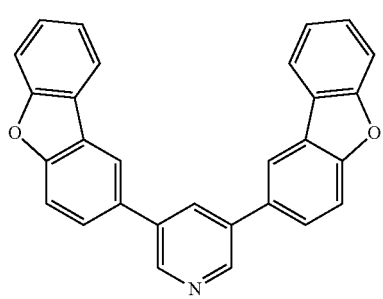
Compound 28
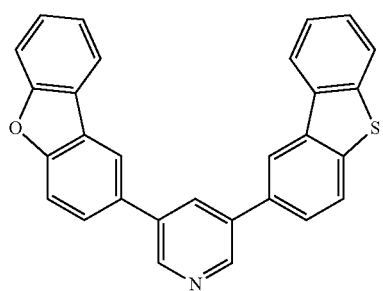
Compound 29
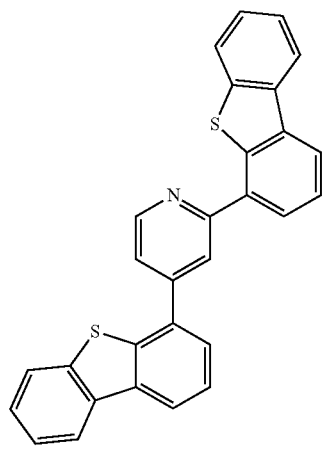
Compound 30
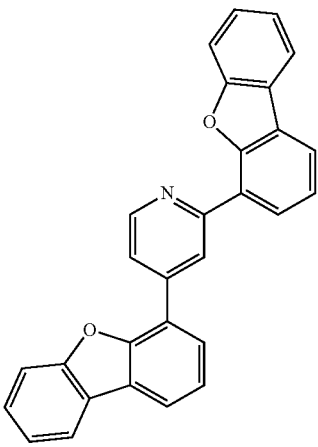
Compound 31
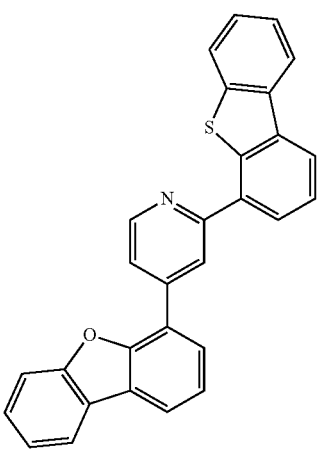
Compound 32
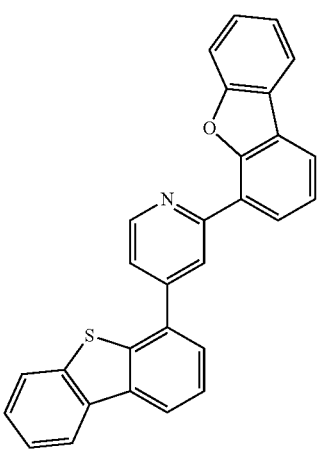

Compound 33
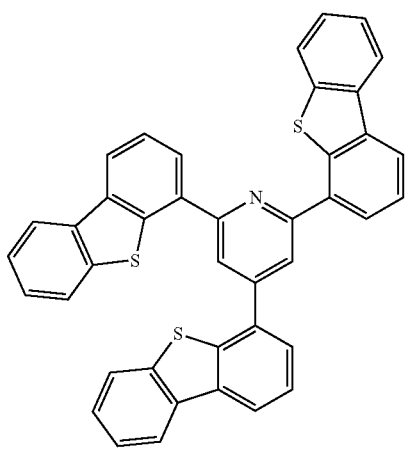
Compound 34
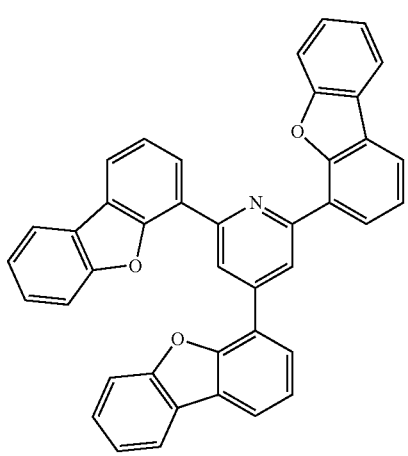
Compound 35
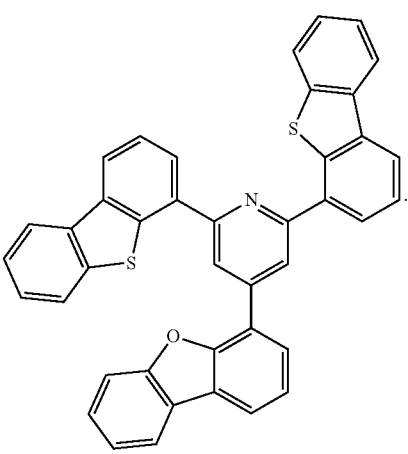
As used herein, the following compounds have the following structures:
H1
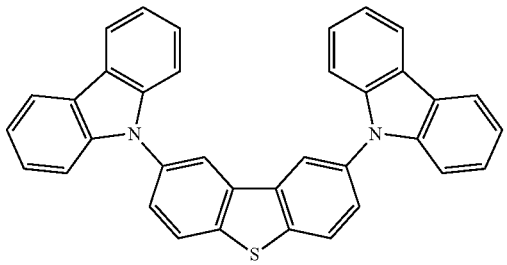
P1
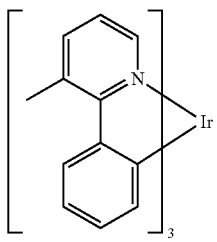
P2
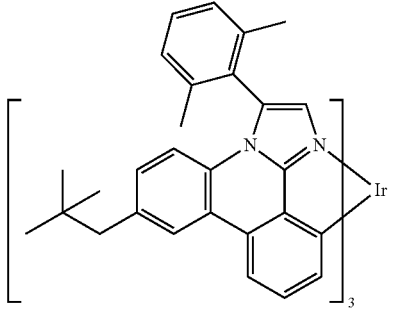
P3
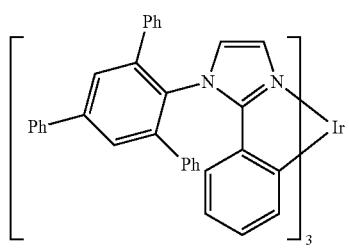
P4
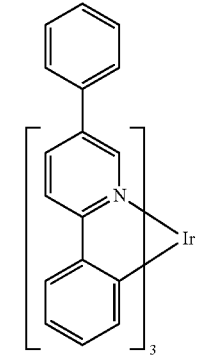

P5

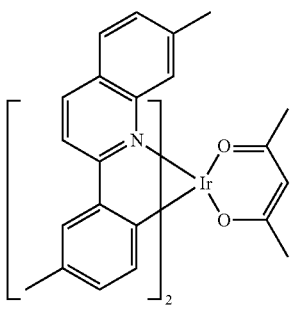

P6

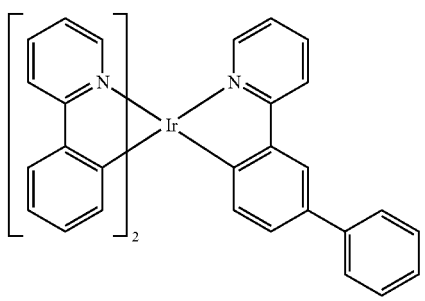

P7

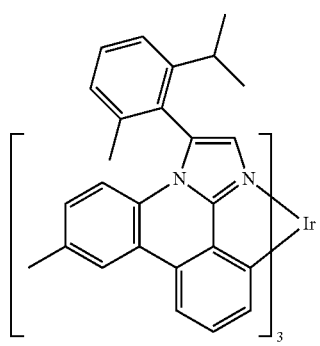

HPT

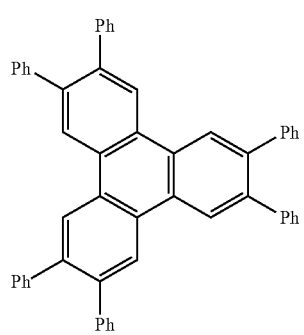

NPD

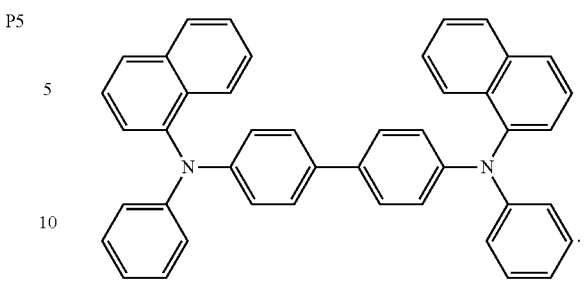

Figure 3:
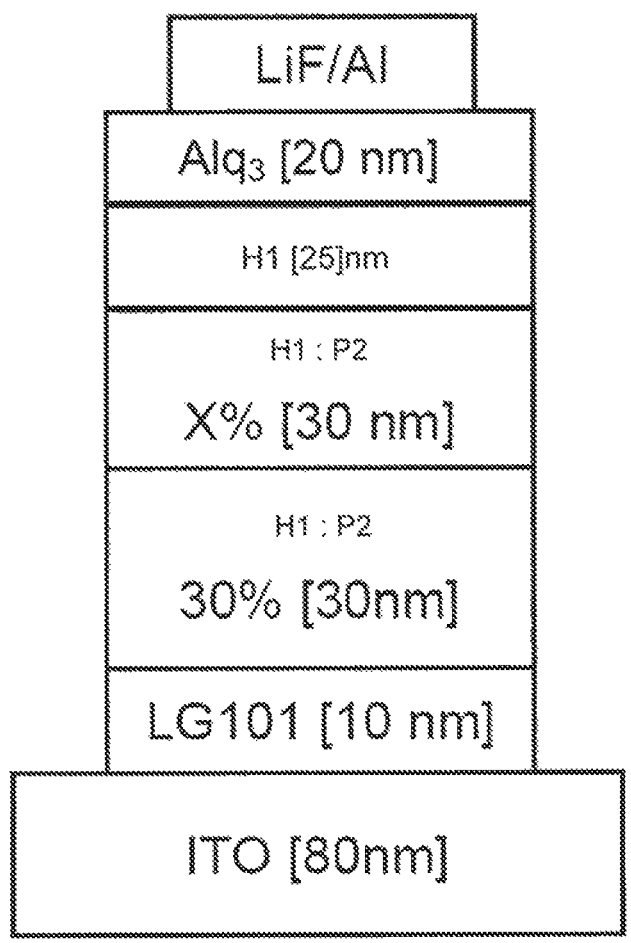
FIG. 3 shows an organic light emitting device including compounds disclosed herein.

Particular host-dopant combinations for the emissive layer of an OLED are also provided which may lead to devices having particularly good properties. Specifically, devices having an emissive layer using H1 as the host and P1, P2, or P7 as an emissive dopant are demonstrated to have particularly good properties. Such devices may be particularly favorable when the emissive layer includes two organic layers, a first organic layer including H1 doped with P1, and a second organic layer including H1 doped with P2, as illustrated in FIG. 3.

Figure 9:
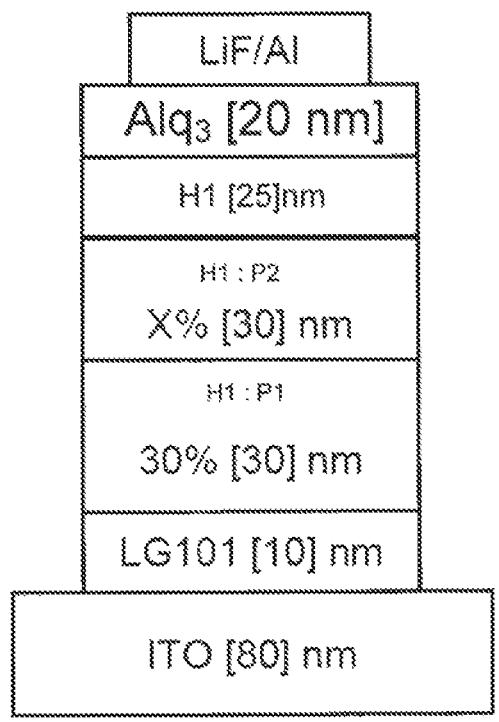
FIG. 9 shows an organic light emitting device including compounds disclosed herein.

Similarly, devices having an emissive layer using Compound 1 as the host and P3, P4 and/or P5 as dopants may lead to devices having particularly good properties. Specifically, devices having an emissive layer using Compound 1 as the host and P3 as an emissive dopant, and/or an emissive layer with multiple dopants using Compound 1 as the host and P4 and P5 as dopants, where P5 is the primary emissive dopant in the layer. Such devices may be particularly favorable when the emissive layer includes two organic layers, a first organic layer including Compound 1 doped with P3, and a second organic layer including Compound 1 doped with P4 and P5, as illustrated in FIG. 9.

Devices having an emissive layer using Compound 23 as the host and P1 as the dopant may also lead to devices having particularly good properties.

Additionally, a consumer product comprising a device having an anode, a cathode, and an organic layer, disposed between the anode and the cathode. The organic layer further comprises a material containing a compound selected from the group consisting of Compound 2G-35G where $R_1$ through $R_8$ are independently selected from the group consisting of any alkyl, alkoxy, amino, alkenyl, alkynyl, arylkyl, aryl, heteroaryl and hydrogen, and where each of $R_1$ through $R_8$ may represent multiple substitutions.

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
|---|---|---|
| Hole injection materials | | |
| Phthalocyanine and porphryin compounds | 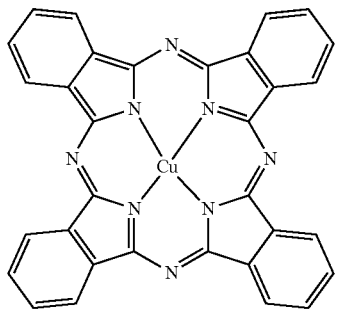 | Appl. Phys. Lett. 69, 2160 (1996) |
| Starburst triarylamines | 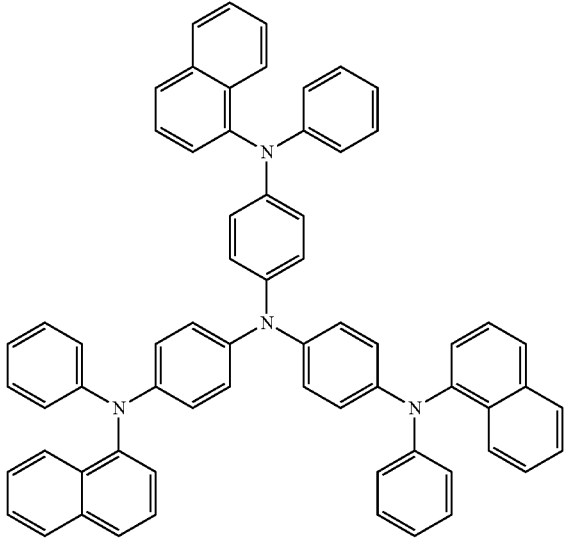 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polythiophene) | 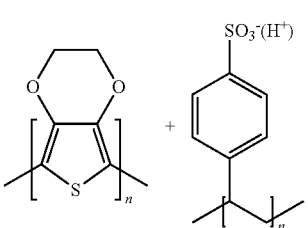 | Synth. Met. 87, 171 (1997) |
| Arylamine complexed with metal oxides such as molybdenum and tungsten oxides | 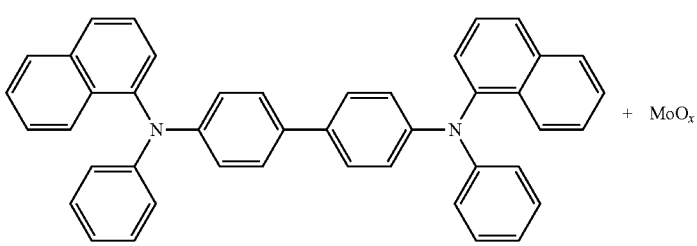 [SMILES: c1ccc(N(c2ccc(-c3ccc(N(c4ccccc4)c4cccc5ccccc45)cc3)cc2)c2cccc3ccccc23)cc1] + $MoO_x$ | SID Symposium Digest, 37, 923 (2006) |
| Hole transporting materials | | |

TABLE 1-continued
| MATERIAL | EXAMPLES OF MATERIAL | PUBLICATIONS |
|---|---|---|
| Triarylamines (e.g., TPD, α-NPD) | 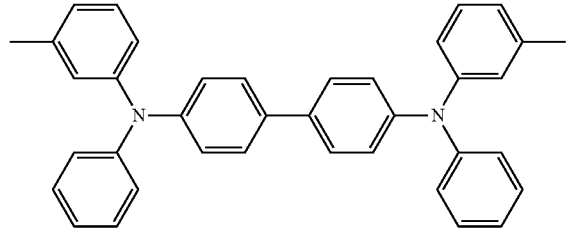 | Appl. Phys. Lett. 51, 913 (1987) |
| | 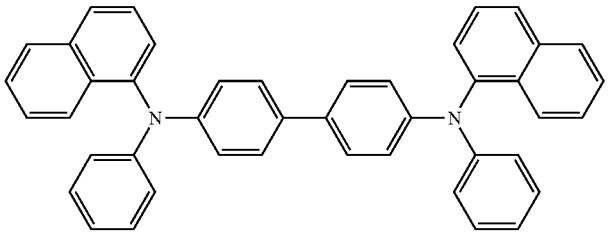 [SMILES: c1ccc(N(c2ccc(-c3ccc(N(c4ccccc4)c4cccc5ccccc45)cc3)cc2)c2cccc3ccccc23)cc1] | U.S. Pat. No. 5,061,569 |
| | 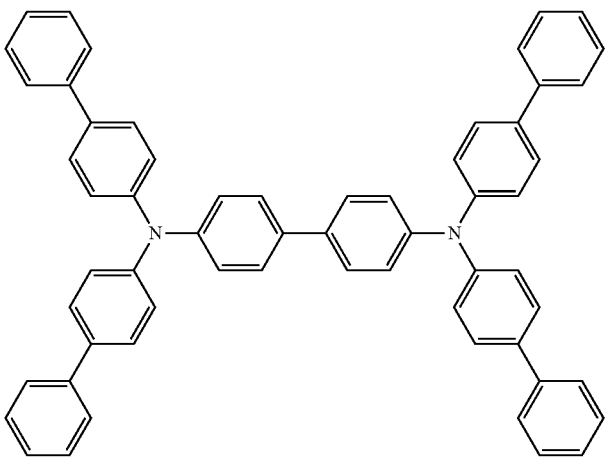 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 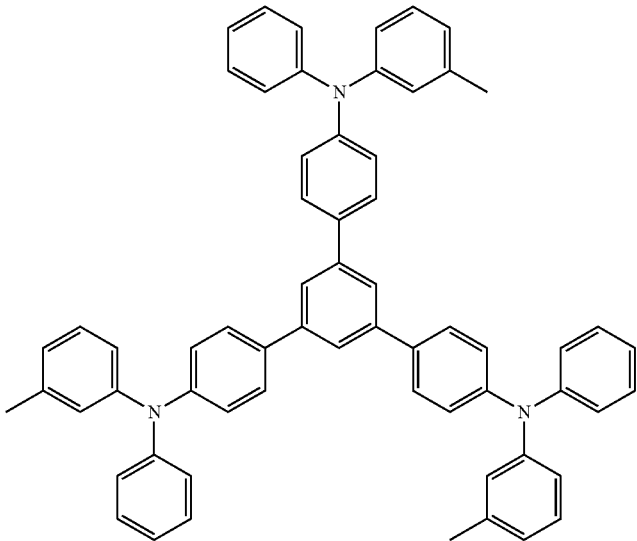 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE 1-continued

| MATERIAL | EXAMPLES OF MATERIAL | PUBLICATIONS |
|---|---|---|
| | | Appl. Phys. Lett. 90, 183503 (2007) |
| | | Appl. Phys. Lett. 90, 183503 (2007) |
| Triaylamine on spirofluorene core | | Synth. Met. 91, 209 (1997) |
| Arylamine carbazole compounds | | Adv. Mater. 6, 677 (1994) |

TABLE 1-continued
| MATERIAL | EXAMPLES OF MATERIAL | PUBLICATIONS |
| --- | --- | --- |
| Indolocarbazoles | 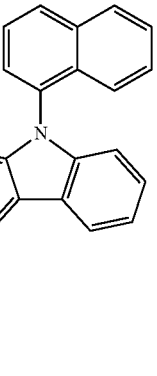 | Synth. Met. 111, 421 (2000) |
| Isoindole compounds | 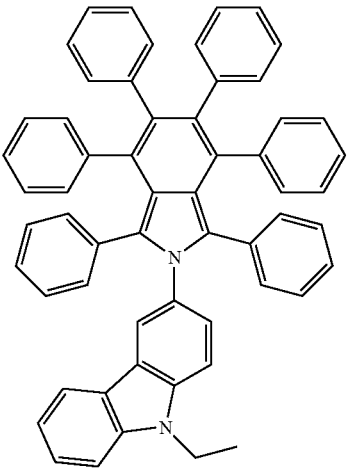 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
Phosphorescent OLED host materials
Red hosts
| | | |
| --- | --- | --- |
| Arylcarbazoles | 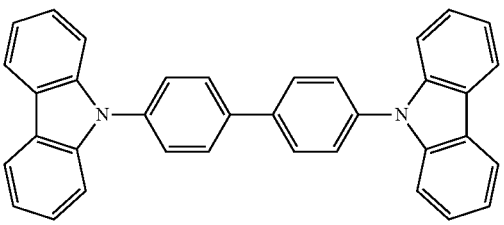 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| Metal 8-hydroxy-quinolates (e.g. $Alq_3$, BAlq) | 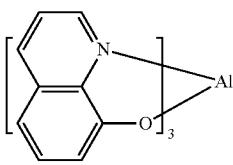 | Nature 395, 151 (1998) |
| | 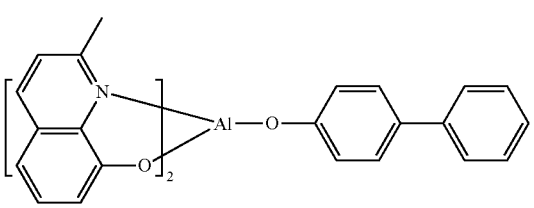 | US20060202194 |

TABLE 1-continued

| MATERIAL | EXAMPLES OF MATERIAL | PUBLICATIONS |
| --- | --- | --- |
| | | WO2005014551 |
| Metal phenoxy-benzothiazole compounds | | Appl. Phys. Lett. 90, 123509 (2007) |
| Conjugated oligomers and polymers (e.g., polyfluorene) | | Org. Electron. 1, 15 (2000) |
| Green hosts | | |
| Arylcarbazoles | | Appl. Phys. Lett. 78, 1622 (2001) |
| | | US2003175553 |
| | | WO2001039234 |

TABLE 1-continued

| MATERIAL | EXAMPLES OF MATERIAL | PUBLICATIONS |
| --- | --- | --- |
| Aryltriphenylene compounds | | US20060280965 |
| | | US20060280965 |
| Polymers (e.g., PVK) | | Appl. Phys. Lett. 77, 2280 (2000) |
| Spirofluorene compounds | | WO2004093207 |
| Metal phenoxybenzooxazole compounds | | WO05089025 |

TABLE 1-continued

| MATERIAL | EXAMPLES OF MATERIAL | PUBLICATIONS |
|---|---|---|
| | | WO06132173 |
| | | JP200511610 |
| Spirofluorene-carbazole compounds | | JP2007254297 |
| | | JP2007254297 |
| Indolocabazoles | | WO07063796 |

| MATERIAL | EXAMPLES OF MATERIAL | PUBLICATIONS |
|---|---|---|
| | | WO07063754 |
| 5-member ring electron deficient heterocycles (e.g., triazole, oxadiazole) | | J. Appl. Phys. 90, 5048 (2001) |
| | | WO04107822 |
| Metal phenoxy-pyridine compounds | | WO05030900 |
| Blue hosts | | |
| Arylcarbazoles | | Appl. Phys. Lett, 82, 2422 (2003) |
| | | US20070190359 |

TABLE 1-continued

| MATERIAL | EXAMPLES OF MATERIAL | PUBLICATIONS |
| --- | --- | --- |
| Dibenzo-thiophene-carbazole compounds | | WO2006114966 |
| Phosphorescent dopants | | |
| Red dopants | | |
| Heavy metal porphyrins (e.g., PtOEP) | | Nature 395, 151 (1998) |
| Iridium (III) organometallic complexes | | Appl. Phys. Lett. 78, 1622 (2001) |
| | | US06835469 |
| | | US06835469 |

TABLE 1-continued

| MATERIAL | EXAMPLES OF MATERIAL | PUBLICATIONS |
|---|---|---|
| | | US20060202194 |
| | | US20060202914 |
| | | US07087321 |
| | | US07087321 |
| | | Adv. Mater. 19, 739 (2007) |

TABLE 1-continued
| MATERIAL | EXAMPLES OF MATERIAL | PUBLICATIONS |
|---|---|---|
| Platinum (II) organometallic complexes | 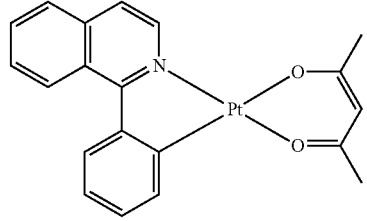 | WO2003040257 |
| Osminum (III) complexes | 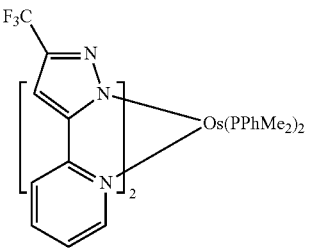 | Chem. Mater. 17, 3532 (2005) |
| Ruthenium (II) complexes | 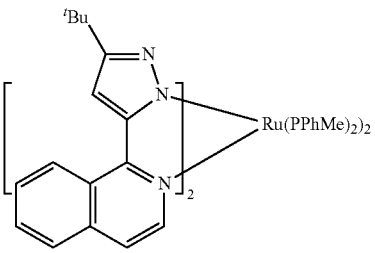 | Adv. Mater. 17, 1059 (2005) |
| Green dopants | | |
| Iridium (III) organometallic complexes | 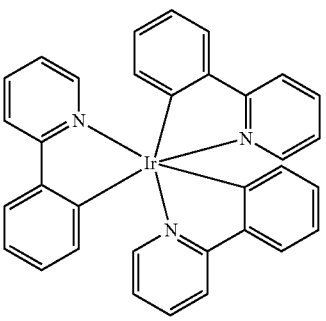  and its derivatives | Inorg. Chem. 40, 1704 (2001) |
| | 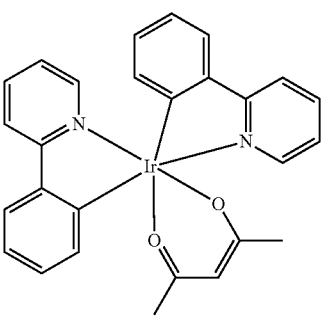 | US2002034656 |

TABLE 1-continued

| MATERIAL | EXAMPLES OF MATERIAL | PUBLICATIONS |
|---|---|---|
| | | US06687266 |
| | | Chem. Mater. 16, 2480 (2004) |
| | | US2007190359 |
| | | US 2006008670<br>JP2007123392 |
| | | Adv. Mater. 16, 2003 (2004) |

TABLE 1-continued

| MATERIAL | EXAMPLES OF MATERIAL | PUBLICATIONS |
|---|---|---|
| | | Angew. Chem. Int. Ed. 2006, 45, 7800 |
| Pt (II) organometallic complexes | | Appl. Phys. Lett. 86, 153505 (2005) |
| | | Appl. Phys. Lett. 86, 153505 (2005) |
| | | Chem. Lett. 34, 592 (2005) |

TABLE 1-continued

| MATERIAL | EXAMPLES OF MATERIAL | PUBLICATIONS |
| --- | --- | --- |
| Gold complexes | | Chem. Commun. 2906 (2005) |
| Rhenium (III) complexes | | Inorg. Chem. 42, 1248 (2003) |
| Blue dopants | | |
| Iridium (III) organometallic complexes | | WO2002002714 |
| | | WO2006009024 |
| | | US2006251923 |

TABLE 1-continued

| MATERIAL | EXAMPLES OF MATERIAL | PUBLICATIONS |
|---|---|---|
| | | WO2006056418, US2005260441 |
| | | US2007190359 |
| | | US2002134984 |
| | | Angew. Chem. Int. Ed. 47, 1 (2008) |
| | | Chem. Mater. 18, 5119 (2006) |
| | | Inorg. Chem. 46, 4308 (2007) |

TABLE 1-continued
| MATERIAL | EXAMPLES OF MATERIAL | PUBLICATIONS |
|---|---|---|
| | 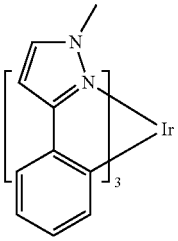 | WO05123873 |
| | 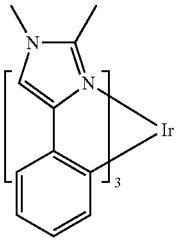 | WO05123873 |
| | 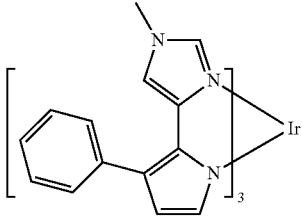 | WO07004380 |
| | 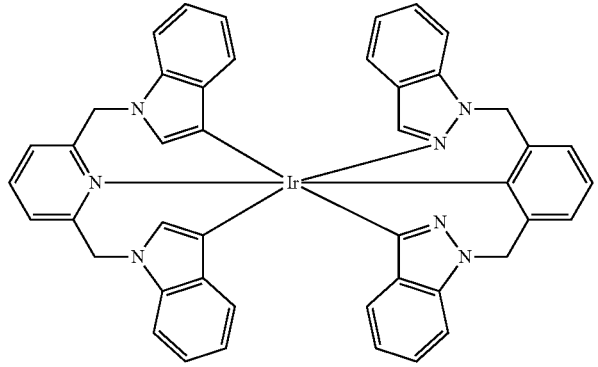 | WO06082742 |
| Osmium (II) complexes | 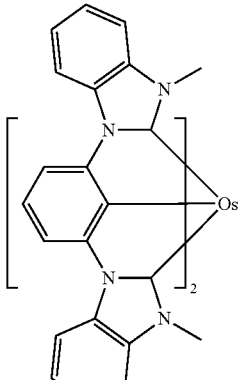 | US2005260449 |

TABLE 1-continued

| MATERIAL | EXAMPLES OF MATERIAL | PUBLICATIONS |
| --- | --- | --- |
|  | [Os(PPh)₃ complex structure] | Organometallics 23, 3745 (2004) |
| Gold complexes | [Ph₂P-CH₂-PPh₂ bridged Au-Cl dimer] | Appl. Phys. Lett. 74, 1361 (1999) |
| Platinum (II) complexes | [Pt complex with dimethylthiophene and pyrazolylborate] | WO06098120, WO06103874 |
| Exciton/hole blocking layer materials | | |
| Bathocuprine compounds (e.g., BCP, BPhen) | [BCP structure] | Appl. Phys. Lett. 75, 4 (1999) |
|  | [BPhen structure] | Appl. Phys. Lett. 79, 449 (2001) |
| Metal 8-hydroxy-quinolates (e.g., BAlq) | [BAlq structure] | Appl. Phys. Lett. 81, 162 (2002) |

TABLE 1-continued
| MATERIAL | EXAMPLES OF MATERIAL | PUBLICATIONS |
| --- | --- | --- |
| 5-member ring electron deficient heterocycles such as triazole, oxadiazole, imidazole, benzoimidazole | 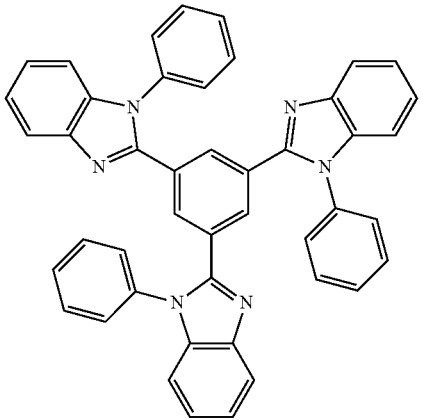 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 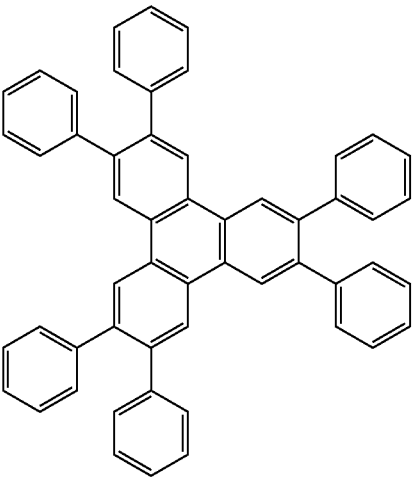 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 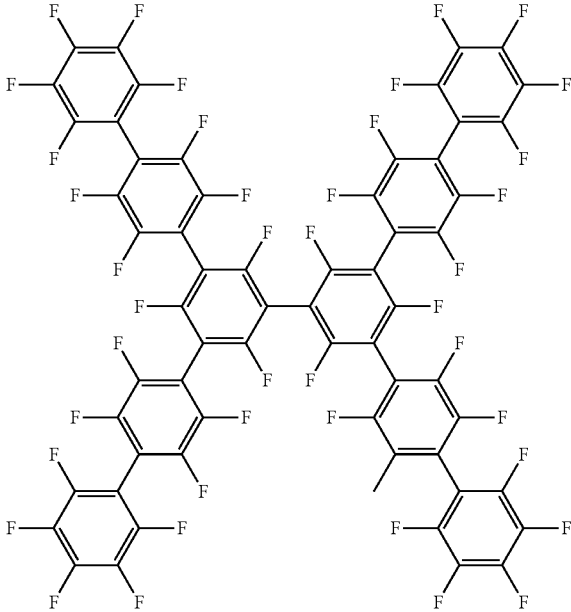 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
Electron transporting materials

TABLE 1-continued

| MATERIAL | EXAMPLES OF MATERIAL | PUBLICATIONS |
|---|---|---|
| Anthracene-benzoimidazole compounds | | WO03060956 |
| Anthracene-benzothiazole compounds | | Appl. Phys. Lett. 89, 063504 (2006) |
| Metal 8-hydroxy-quinolates (e.g., Alq$_3$) | | Appl. Phys. Lett. 51, 913 (1987) |
| Metal hydroxy-benoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |

TABLE 1-continued
| MATERIAL | EXAMPLES OF MATERIAL | PUBLICATIONS |
|---|---|---|
| 5-member ring electron deficient heterocycles (e.g., triazole, oxadiazole, imidazole, benzoimidazole) | 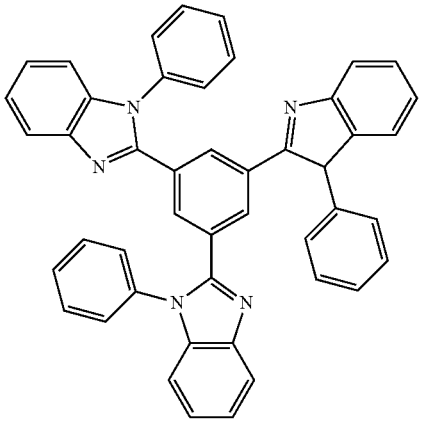 [SMILES: c1ccc(C2C(c3cc(-c4nc5ccccc5n4-c4ccccc4)cc(-c4nc5ccccc5n4-c4ccccc4)c3)=Nc3ccccc32)cc1] | Appl. Phys. Lett. 74, 865 (1999) |
| | 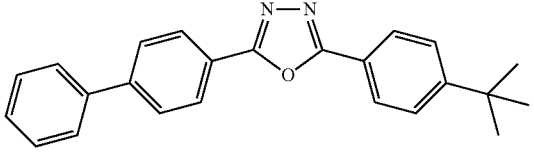 [SMILES: CC(C)(C)c1ccc(-c2nnc(-c3ccc(-c4ccccc4)cc3)o2)cc1] | Appl. Phys. Lett. 55, 1489 (1989) |
| | 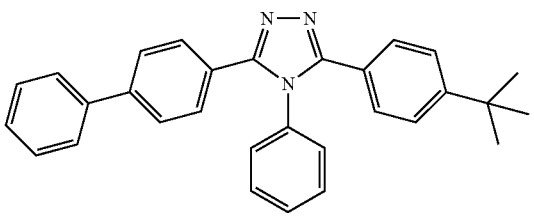 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 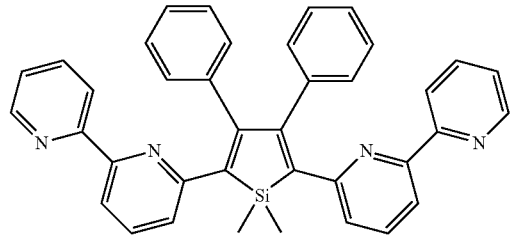 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 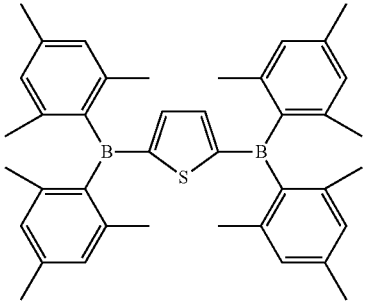 | J. Am. Chem. Soc. 120, 9714 (1998) |
| Fluorinated aromatic compounds | 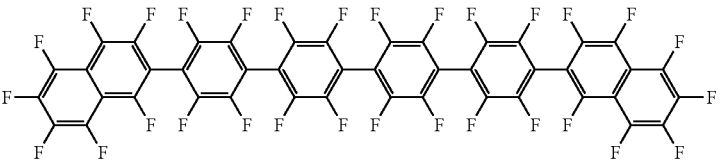 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |

EXPERIMENTAL

Compound Examples

Some of the dibenzothiophene-containing compounds were synthesized, as follows:

Compound 1

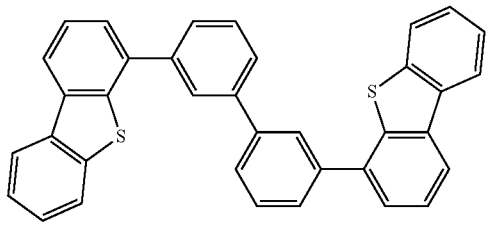

Step 1. 3,3'-dihydroxybiphenyl (9.3 g, 50 mmol) was dissolved in 100 mL of $CH_2Cl_2$, followed by the addition of pyridine (15.8 g, 200 mmol). To this solution at −15° C., $Tf_2O$ (42.3 g, 150 mmol) was added dropwise. The mixture was continued to stir at room temperature for 5 h. The organic phase was separated and washed with brine once. The crude product was further purified by a silica column. 3,3'-ditriflate-biphenyl was obtained as pale white solid (21.3 g).

Step 2. To a 500 mL round flask was added 3,3'-ditriflate-biphenyl (2.7 g, 6 mmol), 4-dibenzothiopheneboronic acid (4.1 g, 18 mmol), $Pd_2(dba)_3$ (0.2 g, 0.2 mmol), 2-dicyclohexylphosphino-2',6'-dimethoxybiphenyl (0.3 g, 0.8 mmol), potassium phosphate tribasic (5.1 g, 24 mmol), and 150 mL of toluene. The reaction was heated to reflux and stirred under a nitrogen atmosphere for 24 hours. After cooling, the mixture was purified by a silica gel column. Yield was 2.6 g.

Compound 2

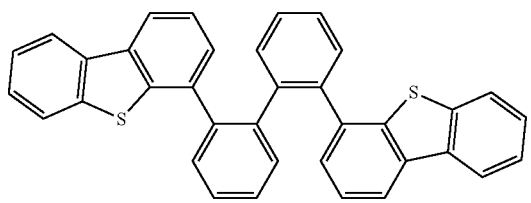

To a 500 mL round flask was added 2,2'-ditriflatebiphenyl (2.7 g, 6 mmol), 4-dibenzothiopheneboronic acid (4.1 g, 18 mmol), $Pd_2(dba)_3$ (0.2 g, 0.2 mmol), 2-dicyclohexylphosphino-2',6'-dimethoxybiphenyl (0.3 g, 0.8 mmol), potassium phosphate tribasic (5.1 g, 24 mmol), and 150 mL of toluene. The reaction was heated to reflux and stirred under a nitrogen atmosphere for 24 hours. After cooling, the mixture was purified by a silica gel column. Yield was 2.5 g.

Compound 3

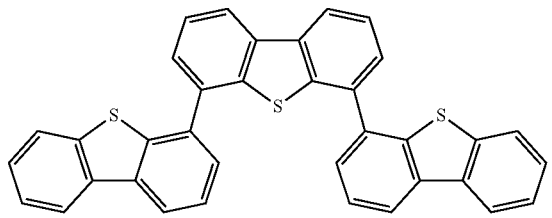

To a 500 mL round flask was added 4,6-diiododibenzothiophene (4.2 g, 9.6 mmol), 4-dibenzothiopheneboronic acid (5.3 g, 23.1 mmol), $Pd_2(dba)_3$ (0.2 g, 0.2 mmol), 2-dicyclohexylphosphino-2',6'-dimethoxybiphenyl (0.3 g, 0.8 mmol), potassium phosphate tribasic (7.4 g, 35 mmol), and 150 mL of toluene. The reaction was heated to reflux and stirred under a nitrogen atmosphere for 24 hours. After cooling, the mixture was purified by a silica gel column. Yield was 2.4 g.

Compound 4

To a 500 mL round flask was added 4,6-diiododibenzothiophene (3.9 g, 8.9 mmol), carbazole (3.3 g, 19.6 mmol), $Pd_2(dba)_3$ (0.2 g, 0.2 mmol), 2-dicyclohexylphosphino-2',6'-dimethoxybiphenyl (0.3 g, 0.8 mmol), sodium t-butoxide (5.8 g, 60 mmol), and 200 mL of xylene. The reaction was heated to reflux and stirred under a nitrogen atmosphere for 24 hours. After cooling, the mixture was purified by a silica gel column. Yield was 2.2 g.

Compound 5

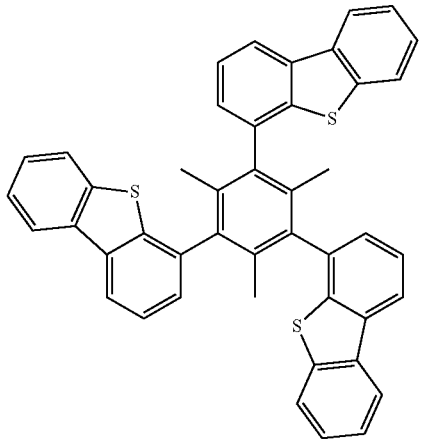

Step 1. 2,6-Dibromo-1,3,5-trimethylbenzene (8.34 g, 30 mmol) was dissolved in 50 ml of $CHCl_3$ and suspended with 1.0 g of iron powder in 200 ml round-bottom flask. Bromine (2.00 ml, 31 mmol) was added dropwise at room temperature and reaction mixture was heated to reflux for 3 hours, cooled down to room temperature and stirred overnight. Solution was decanted, washed with NaOH 10% aq., filtered and evaporated. The solid residue was crystallized from chloroform, providing 7.00 g of yellow solid (2,4,6-tribromo-1,3,5-trimethylbenzene).

Step 2. The 1 L round-bottom flask equipped with magnetic stirrer and reflux condenser was charged with 2,4,6-tribromo-1,3,5-trimethylbenzene (3.4 g, 9.5 mmol), 4-dibenzothiopheneboronic acid (8.7 g, 38 mmol), Pd$_2$(OAc)$_2$ (0.16 g, 0.7 mmol), 2-dicyclohexylphosphino-2',6'-dimethoxybiphenyl (0.46 g, 1.1 mmol), potassium phosphate tribasic (53 g, 250 mmol), 1.2 ml of water and 700 mL of toluene. The reaction was heated to reflux and stirred under a nitrogen atmosphere for 24 hours. After cooling, the mixture was purified by a silica gel column. Yield was 5.2 g.

Compound 6

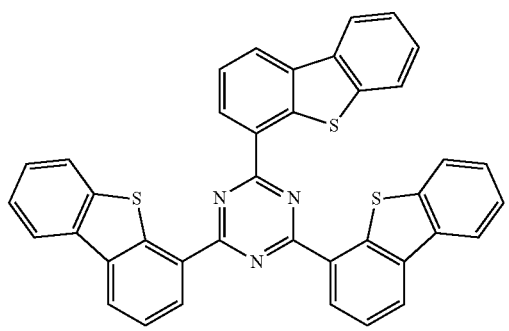

To a 500 mL round flask was added cyanuric chloride (1.5 g, 8.0 mmol), 4-dibenzothiopheneboronic acid (6.8 g, 30 mmol), Pd$_2$(dba)$_3$ (0.2 g, 0.2 mmol), 2-dicyclohexylphosphino-2',6'-dimethoxybiphenyl (0.3 g, 0.8 mmol), potassium phosphate tribasic (8.5 g, 40 mmol), and 250 mL of toluene. The reaction was heated to reflux and stirred under a nitrogen atmosphere for 24 hours. After cooling, the mixture was filtered. The product was further purified by recrystallization from EtOAc. Yield was 3.0 g.

Compound 7

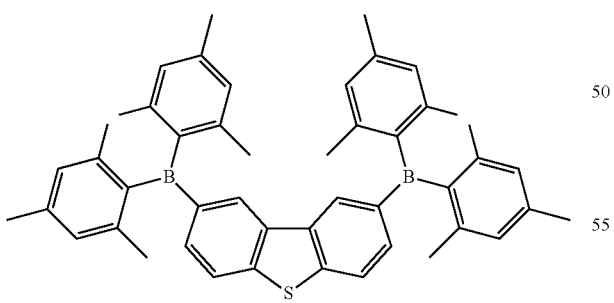

2,8-Dibromobenzothiophene (2.5 g, 7.3 mmol) in 150 mL of THF was treated with n-BuLi (1.6 M in hexane, 10 mL, 16 mmol) at −78° C. for 1 h. Dimesitylboron fluoride (5.0 g, 16.8 mmol) in 40 mL of ether was added dropwise. After the mixture was stirred for another 1 h, the mixture was slowly warmed up to room temperature and continued to stir overnight. The product was purified by a silica gel column. Yield was 2.8 g.

Compound 8

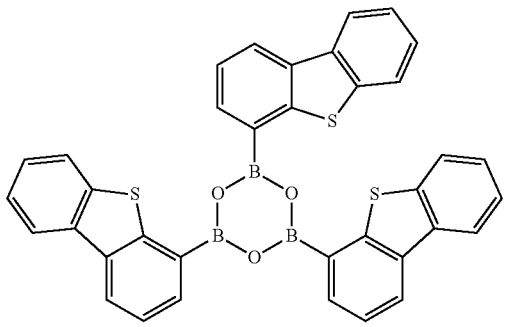

4-Dibenzothiopheneboronic acid (5.0 g) was suspended in 300 mL of xylene and performed the Dean-Stark extraction for 5 h. After cooling down, the solid was collected, washed with EtOAc and hexane, and sublimed at 320° C. twice. Yield was 3.6 g.

Compound 9

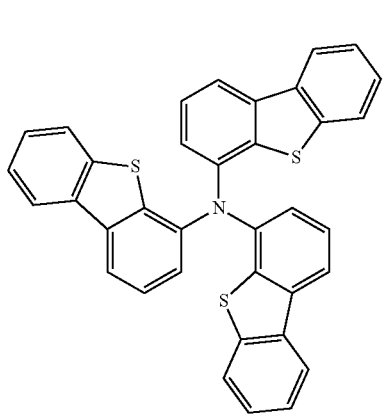

To a 500 mL round flask lithium amide (0.2 g, 10 mmol), 4-iododibenzothiophene (9.9 g, 32 mmol), Pd$_2$(dba)$_3$ (0.2 g, 0.2 mmol), 2-dicyclohexylphosphino-2',4',6'-triisopropylbiphenyl (0.4 g, 0.8 mmol), sodium t-butoxide (2.9 g, 30 mmol), and 200 mL of toluene were added. The reaction was heated to reflux and stirred under a nitrogen atmosphere for 24 hours. After cooling, the mixture was purified by a silica gel column. Yield was 4.0 g.

Compound 10

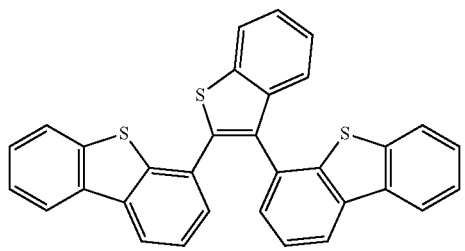

The 500 mL round flask was charged with 2,3-dibromobenzo[b]thiophene (5.0 g, 17.1 mmol), 4-dibenzothiopheneboronic acid (10.0 g, 43.8 mmol), Pd$_2$(PPh$_3$)$_4$ (0.8 g, 0.7 mmol), potassium carbonate (14.2 g, 103 mmol) in 30 ml water followed by 200 ml of toluene. The reaction was heated to reflux and stirred under a nitrogen atmosphere for 24 hours. After cooling, separation of aqueous phase and evaporation the mixture was purified by a silica gel column (hexane/ethyl acetate 4/1 mixture), providing target compound as solidified colorless oil (4.6 g).

Compound 11

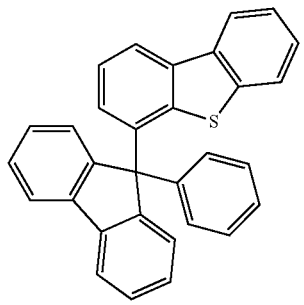

Step 1. Dibenzothiophene (9.21 g, 50 mmol) was dissolved in 100 ml of dry THF and solution was cooled to −50° C. n-BuLi (1.6 molar solution in hexanes, 40 ml, 64 mmol) was added dropwise. The reaction mixture was warmed to room temperature, stirred for 4 hours and cooled to −30° C. Dibenzofluorenone (9.0 g, 50 mmol) in 70 ml THF was added dropwise, reaction mixture was allowed to warm to room temperature and stirred overnight. The reaction mixture was diluted with ethyl acetate (75 ml), washed with brine 3 times, dried over MgSO$_4$, filtered and evaporated. The solid residue was purified by column chromatography on silica (hexane/ethyl acetate 7/3) providing 12.0 g of 9-(dibenzo[b,d]thiophen-4-yl)-9H-fluoren-9-ol as white solid.

Step 2. 9-(Dibenzo[b,d]thiophen-4-yl)-9H-fluoren-9-ol (product from the Step 1, 3.64 g, 10 mmol) were dissolved in 100 ml of dry toluene. Twenty drops of 10% solution of P$_2$O$_5$ in CH$_3$SO$_3$H were added at room temperature, and reaction mixture was stirred for 5 hours. The solution was decanted from solid residue, filtered through silica plug and evaporated. The solid residue was subjected to column chromatography (silica, hexane/ethyl acetate 4/1) providing 4.0 g of white solid.

Compound 12

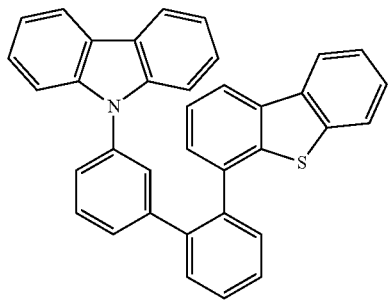

Step 1. The 200 ml round-bottom flask equipped with reflux condenser and magnetic stirrer was charged with carbazole (14.75 g, 88 mmol), 3-iodobromobenzene (25.0 g, 88 mmol), Pd$_2$(dba)$_3$ (0.8 g, 0.85 mmol) and dppf (1,1'-bis (diphenylphosphino)ferrocene, 0.98 g, 1.8 mmol), sodium t-buthoxide (25 g, 265 mmol) and 100 ml of dry xylene. Reaction mixture was refluxed under N$_2$ atmosphere for 48 hours, cooled down to room temperature and evaporated. The solid residue was subjected to column chromatography on silica (eluent—hexane/ethyl acetate 9/1) providing 11.7 g of 9-(3-bromophenyl)-9H-carbazole as white solid.

Step 2. 9-(3-Bromophenyl)-9H-carbazole (11.7 g, 36 mmol), Bis(pinacolato)diboron (13.85 g, 54 mmol), potassium acetate (7.00 g, 71 mmol), 1,1'-bis(diphenylphosphino) ferrocene]dichloropalladium (II) (0.6 g) were dissolved in 100 ml of dry dioxane and refluxed under N$_2$ atmosphere overnight. Then reaction mixture was cooled down to room temperature, diluted with ethyl acetate, washed with brine, dried over magnesium sulfate, and evaporated. The solid residue was subjected to column chromatography on silica (eluent hexane/ethyl acetate 5/1), providing 8.00 of 9-(3-(4,4,5, 5-tetramethyl-1,3,2-dioxaborolan-2-yl)phenyl)-9H-carbazole as yellow solid. Analytically pure material may be prepared by crystallization from hexane, otherwise product was used without additional purification.

Step 3. 2-Bromoanisole (5.61 g, 30 mmol) and 4-dibenzothiopheneboronic acid (6.84 g, 30 mmol), Pd$_2$(PPh$_3$)$_4$ (1.00 g, 0.8 mmol) were dissolved in 100 ml of toluene. Saturated solution of sodium carbonate (12.5 g in water) was added, and reaction mixture was heated to reflux under N$_2$ atmosphere overnight. Then reaction mixture was cooled down to room temperature, separated organic phase and evaporated toluene. The solid residue was subjected to column chromatography on silica (eluent—hexane/ethyl acetate 4/1) providing 4-(2-methoxyphenyl)dibenzo[b,d]thiophene as 6.6 g of colorless solidified oil.

Step 4. 4-(2-Methoxyphenyl)dibenzo[b,d]thiophene (6.6 g, 23 mmol) and pyridinium hydrochloride (27 g, 230 mmol) were mixed together, placed in the 100 ml round bottom flask and heated to reflux for 45 min. Reaction mixture was cooled to 60° C., diluted with 100 ml water and extracted with ethyl acetate. The organic phase was separated, dried over magnesium sulfate, filtered and evaporated. The residue was subjected to column chromatography on silica (eluent hexane/ethyl acetate 5/1), providing 4.00 g of 2-(dibenzo[b, d]thiophen-4-yl)phenol as clear solidified oil.

Step 5. 2-(Dibenzo[b,d]thiophen-4-yl)phenol (3.9 g, 14 mmol) was dissolved in 80 ml of dry dichloromethane, containing 5 ml of dry pyridine, and solution was cooled in the ice bath. The triflic anhydride (5 ml, 28 mmol) was added dropwise, the reaction mixture was stirred overnight at room temperature, washed with water and evaporated. The residue was purified by column chromatography on silica (eluent hexane/ethyl acetate 9/1), providing 4.2 g of clear colorless solidified oil.

Step 6. The 200 ml round bottom flask with reflux condenser and magnetic stirrer was charged with triflate from Step 5 (4.1 g, 10 mmol) and boronic ester from Step 2 (3.7 g, 10 mmol) followed by tribasic potassium phosphate (6.36 g, 30 mmol), palladium acetate (0.67 g, 0.3 mmol)), 2-dicyclohexylphosphino-2',6'-dimethoxybiphenyl (0.8 g, 0.6 mmol), 200 ml of toluene and 6 ml of water. The reaction was heated to reflux and stirred under a nitrogen atmosphere for 24 hours. After cooling, the mixture was purified by a silica gel column with eluent hexane/ethyl acetate 4/1, providing 2.8 g of target compound as white solid.

H1

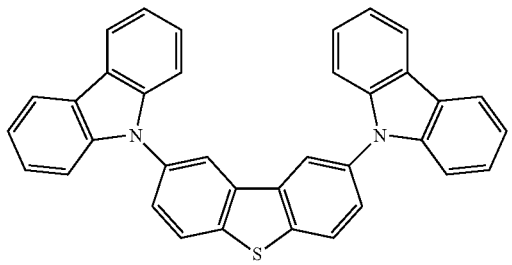

To a 500 mL round flask carbazole (3.7 g, 22 mmol), 2,8-dibromobenzothiophene (3.4 g, 10 mmol), Pd(OAc)₂ (0.1 g, 0.5 mmol), tri-t-butylphosphine (1 M in toluene, 1.5 mL, 1.5 mmol), sodium t-butoxide (6.3 g, 66 mmol), and 200 mL of xylene were added. The reaction was heated to reflux and stirred under a nitrogen atmosphere for 24 hours. After cooling, the mixture was purified by a silica gel column. Yield was 4.7 g.

Compound 13

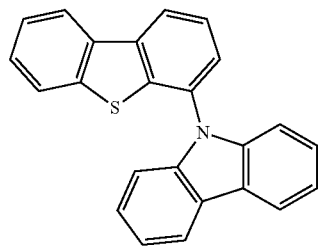

To a 500 mL round flask 4-iododibenzothiophene (6.2 g, 20 mmol), carbazole (4.0 g, 24 mmol), Pd₂(dba)₃ (0.9 g, 1.0 mmol), 2-dicyclohexylphosphino-2',6'-dimethoxybiphenyl (1.6 g, 4.0 mmol), sodium t-butoxide (5.8 g, 60 mmol), and 200 mL of xylene were added. The reaction was heated to reflux and stirred under a nitrogen atmosphere for 24 hours. After cooling, the mixture was purified by a silica gel column. Yield was 2.4 g.

Compound 14

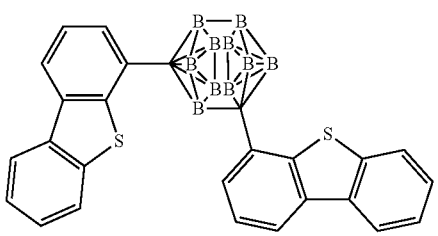

m-Carborane (5.0 g, 35 mmol) in 200 mL of dry DME was treated with n-BuLi (1.6 M in hexane, 48 mL, 76 mmol) at 0° C. for 30 min under nitrogen. After the mixture was warm up to room temperature, CuCl (9.5 g, 96 mmol) was added. The mixture continued to stir for 1 h, and 30 mL of dry pyridine, 4-iododibenzothiophene (22.6 g, 73 mmol) were added. The resulting mixture was refluxed for 60 h. After cooling, the mixture was purified by a silica gel column. Yield was 1.8 g.

Compound 15

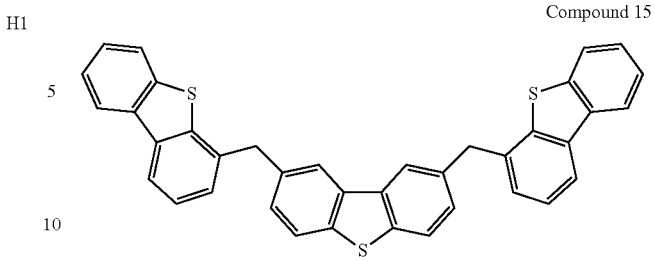

Step 1. Dibenzothiophene (27 g, 147 mmol) in 400 mL of THF was treated slowly with n-BuLi (1.6 M in hexane, 100 mL, 160 mmol) at −50° C. The resulting mixture was slowly warmed up to room temperature and continued to stir for 5 h. The solution was cooled back to −78° C., DMF (61 mL) in 100 mL of THF was added slowly. The mixture continued to stir for another 2 h at this temperature and then warmed up to room temperature. The product was extracted with EtOAc and further purified by a silica gel column. Yield of 4-dibenzothiophenealdehyde was 21 g.

Step 2. To a 300 mL of THF solution of 2,8-dibromodibenzothiophene (3.4 g, 10 mmol) at −78° C. was added slowly by n-BuLi (1.6 M in hexane, 13.8 mL, 22 mmol). After stirred for 1 h at this temperature, the mixture was treated slowly with a 100 mL of THF solution of 4-dibenzothiophenealdehyde (4.2 g, 20 mmol). The solution was then allowed to warm up to room temperature. The product was extracted with EtOAc and further purified by a silica gel column. Yield of dicarbinol intermediate was 4.2 g.

Step 3. To a 50 mL of CH₂Cl₂ solution of above dicarbinol intermediate (4.5 g, 7.4 mmol) and CF₃COOH (60 mL) was added portionwise of solid powder of sodium borohydride (2.8 g, 74 mmol. The mixture was stirred under nitrogen overnight. The solvents was removed by rotovap, and the solid was washed with water then with NaHCO₃ solution. The crude product was further purified by a silica gel column. Yield of final product was 2.4 g.

Compound 16

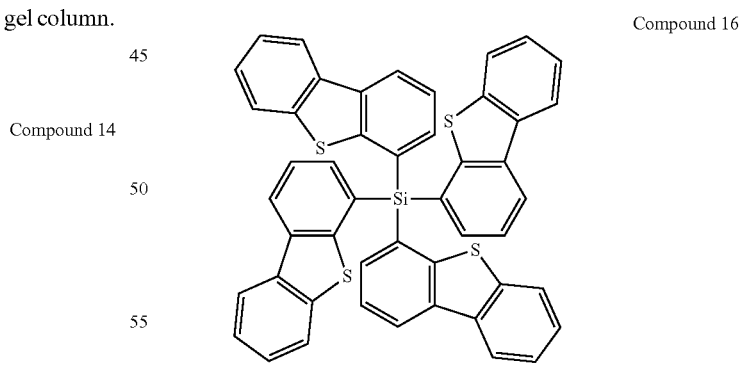

Dibenzothiophene (14 g, 76 mmol) in 200 mL of THF was treated slowly with n-BuLi (1.6 M in hexane, 50 mL, 80 mmol) at −50° C. The resulting mixture was slowly warmed up to room temperature and continued to stir for 5 h. The solution was cooled back to −78° C., SiCl₄ (2.0 g, 12 mmol) was added slowly. The mixture continued to stir for another 2 h at this temperature and 12 h at room temperature. The product was extracted with EtOAc and further purified by a silica gel column. Yield was 3.5 g.

Compound 17

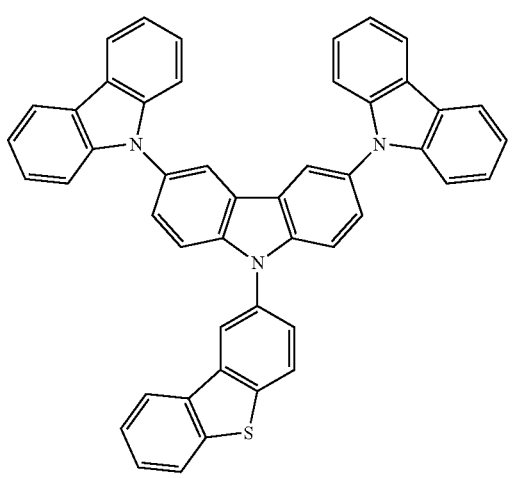

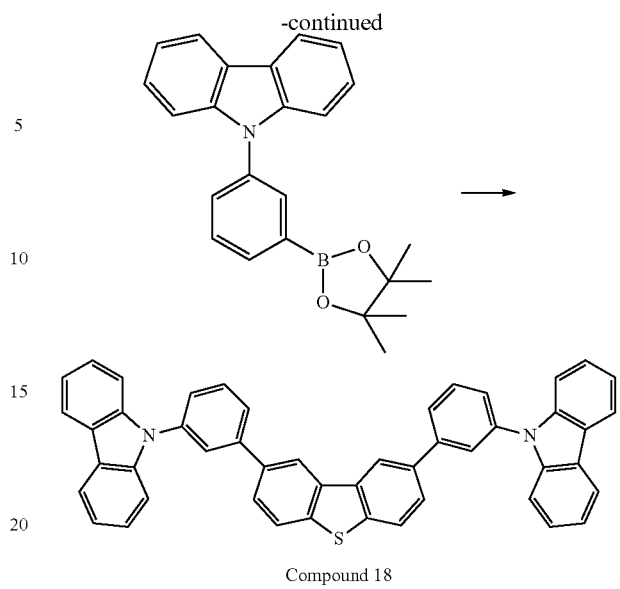

Compound 18

To a 500 mL round flask 3,6-di(9-carbazolyl)carbazole (3.0 g, 6 mmol, prepared similarly as described above for 3-(9-carbazolyl)carbazole), 2-bromobenzothiophene (2.1 g, 7.8 mmol), CuI (0.4 g, 2.0 mmol), trans-1,2-Diaminocyclohexane (0.4 g, 3.6 mmol), potassium phosphate tribasic (3.2 g, 15 mmol), and 250 mL of toluene were added. The reaction was heated to reflux and stirred under a nitrogen atmosphere for 24 hours. After cooling, the mixture was purified by a silica gel column. Yield was 3.1 g.

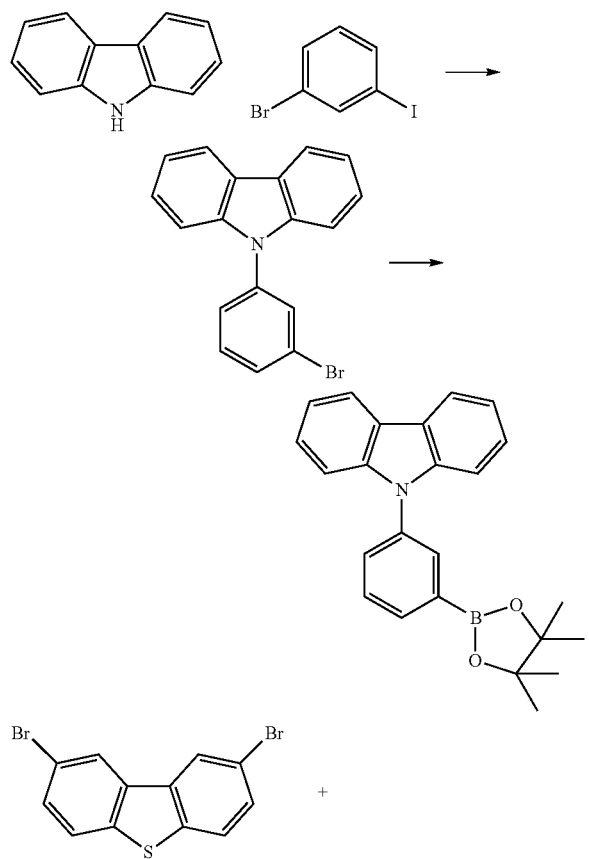

The 300 mL round bottom flask, equipped with magnetic stirrer and refluxed condenser, was charged with carbazole (7.1 g, 42.5 mmol), 3-iodobromobenzene (25.00 g, 88 mmol), $Pd_2(dba)_3$ (800 mg, 1 mol %), dppf (1',1'-bis(diphenylphosphino)ferrocene (975 mg, 2 mol %), sodium t-buthoxide (6.3 g) and m-xylene (100 ml). The reaction mixture was heated to reflux and stirred under nitrogen atmosphere for 48 hours. Then reaction was cooled down to room temperature, filtered through silica plug and evaporated. The residue was subjected to column chromatography on silica gel, eluent gradient mixture hexane-hexane/ethyl acetate mixture 9:1, providing 7.00 g of 9-(3-bromo-phenyl)-9H-carbazole as white solid, structure was confirmed by NMR and GCMS spectroscopy.

7.00 g of 9-(3-bromo-phenyl)-9H-carbazole (21.7 mmol), bis-pinacolatodiborane (8.3 g, 32.7 mmol), potassium acetate (4.30 g) and (1,1'-bis(diphenylphosphino)-ferrocene)dichloropalladium (II) (500 mg) were dissolved in 100 ml of dioxane and refluxed under nitrogen for 24 hours. After evaporation the residue was subjected to column chromatography on silica gel (eluent hexane/ethyl acetate 9/1 mixture), providing pure 9-[3-(4,4,5,5-tetramethyl-[1,3,2]dioxaborolan-2-yl)-phenyl]-9H-carbazole as white solid (11.8 g).

The 300 mL round bottom flask, equipped with magnetic stirrer and refluxed condenser, was charged with 2,8-dibromo-dibenzothiophene (3.42 g, 10 mmol), 9-[3-(4,4,5,5-tetramethyl-[1,3,2]dioxaborolan-2-yl)-phenyl]-9H-carbazole (11.7 g, 30 mmol), palladium (II) acetate (64 mg), 2-dicylohexylphosphino-2',6'-dimethoxybiphenyl (234 mg), potassium phosphate tribasic anhydrous (53.0 g), 700 ml of toluene and 2 ml of water. The reaction mixture was heated to reflux and stirred under nitrogen atmosphere for 24 hours. Then reaction was cooled down to room temperature, filtered through silica plug and evaporated. The residue was washed with hexane, ethanol, water, ethanol and hexane, then was crystallized from toluene. Sublimation (255° C. at $10^{-5}$ mm Hg) provided pure material (white solid, 2.0 g, structure confirmed by NMR.

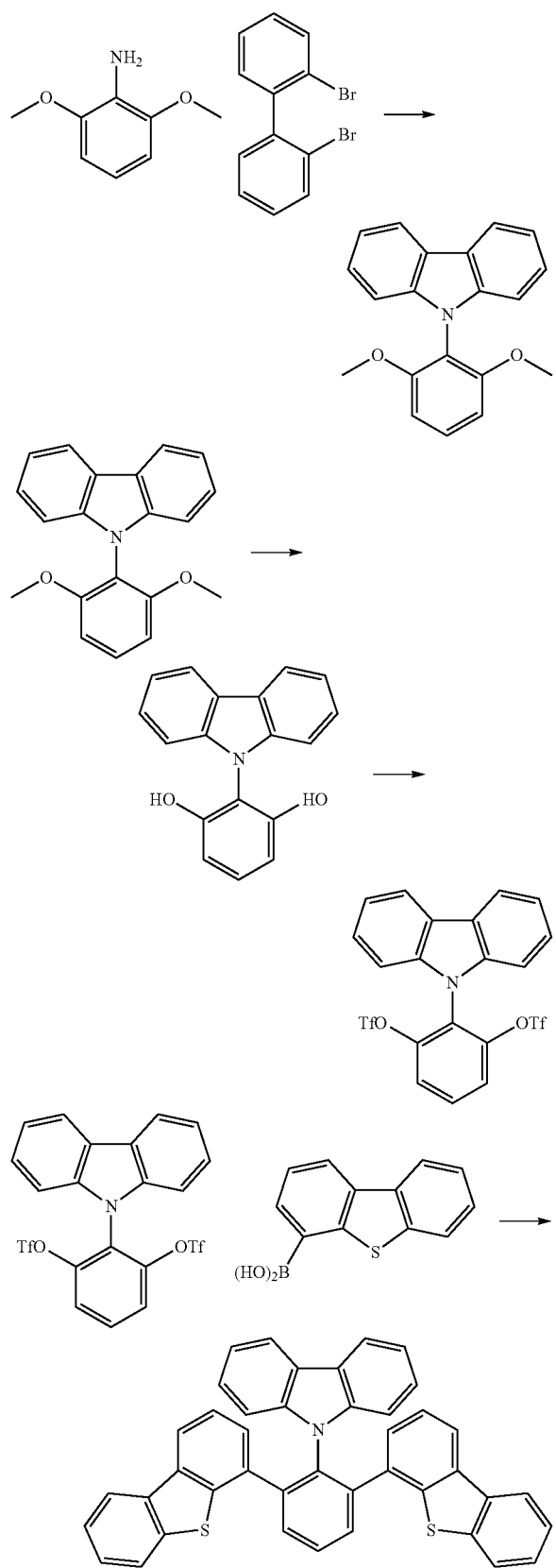

Compound 19

2,6-Dimethoxyaniline (5.5 g, 0.036 mol), 2,2'-dibromobiphenyl (13.45 g, 0.043 mol), sodium tert-butoxide (8.58 g, 0.089 mol) and $Pd_2(dba)_3$ (1.15 g, 13 mmol) were charged into a 500 mL 3-neck flask with 300 mL of anhydrous toluene. This flask was evacuated and back filled with $N_2$ (this procedure was repeated a total of 3 times). Lastly, (9.6 mL, 96 mmol) $P(t-Bu)_3$ 1.0 M in toluene was syringed into the reaction vessel through a septum. The reaction mixture was heated at reflux for 18 h. Heating was then discontinued. The reaction mixture was diluted with 200 mL of water. The toluene layer was separated. The aqueous was extracted 1×200 mL toluene. The toluene extracts were combined, were dried over magnesium sulfate then were filtered and concentrated under vacuum. Silica gel chromatography of the crude product. Solvent system used was 20-35% methylene chloride/hexanes.

9-(2,6-Dimethoxyphenyl)-9H-carbazole (10.00 g) and pyridinium hydrochloride (50.0 g) were placed in the 250 ml round-bottom flask, equipped with magnetic stirrer and immersed in the pre-heated oil bath (230° C., 45 min). The reaction mixture was cooled down to room temperature, diluted with 400 ml water and extracted with ethyl acetate (3×150 ml). Organic fractions were combined, dried over sodium sulfate anhydrous, filtered and evaporated, providing 5.5 g of pure 2-carbazol-9-yl-benzene-1,3-diol. 2-Carbazol-9-yl-benzene-1,3-diol (5.5 g, 20 mmol) and pyridine (6.0 ml) were dissolved in 50 ml DCM (anhydrous) and cooled in the ice bath. Solution of triflic anhydride (6.0 ml) in 20 ml DCM was added dropwise upon intensive stirring, reaction mixture was warmed up to room temperature and stirred overnight. The reaction mixture was washed with water, dried over sodium sulfate, filtered and evaporated, providing crude triflate. Pure material (white solid, 6.0 g) was obtained by column chromatography on silica gel (eluent hexane/ethyl acetate 1/1 mixture).

Bis-triflate (3.13 g, 5.8 mmol), 4-dibenzothiopheneboronic acid (3.30 g, 14.5 mmol), $Pd_2(dba)_3$ (212 mg, 2 mol %), 2-dicylohexylphosphino-2',6'-dimethoxybiphenyl (190 mg, 4 mol %), potassium phosphate tribasic monohydrate (8.00 g), 100 ml of toluene and 1 ml of water were refluxed in the round-bottom flask under nitrogen atmosphere for 24 hours, filtered hot through silica plug and evaporated. The residue was washed with hexane, ethanol, water, ethanol and hexane, then crystallized from toluene, providing pure material (4.1 g).

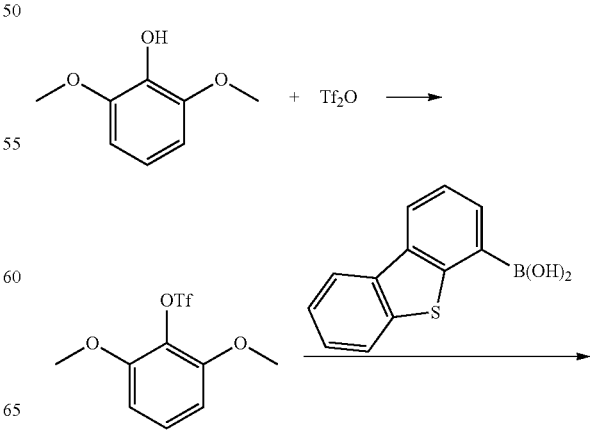

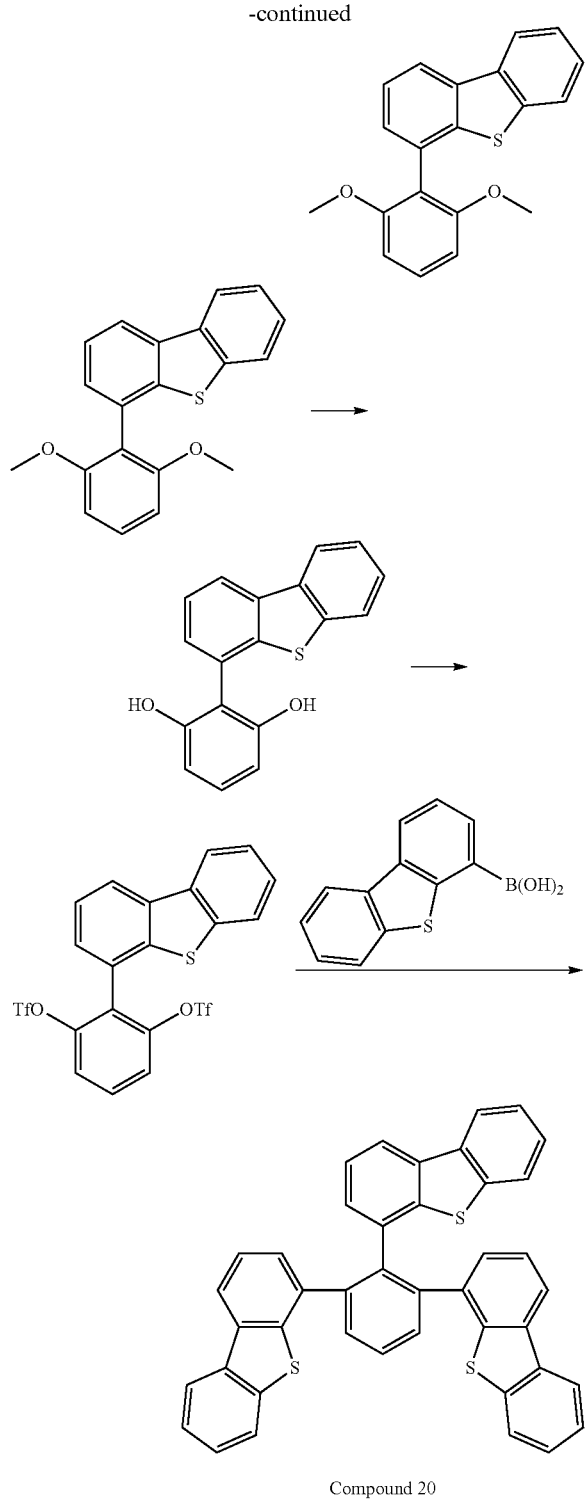

Compound 20

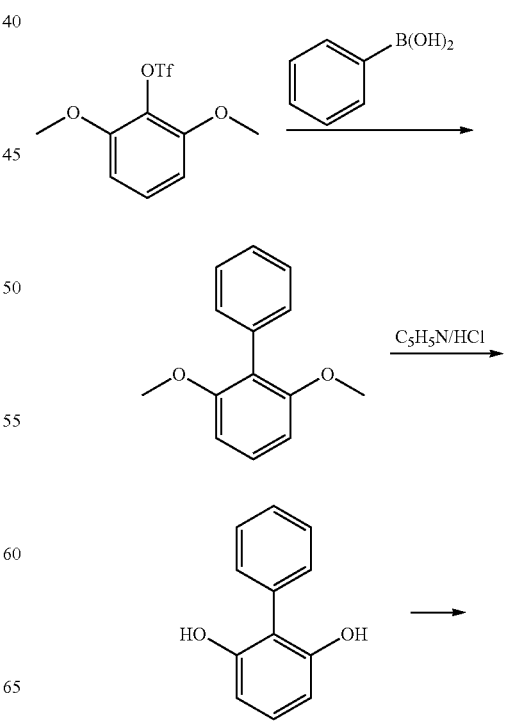

phate tribasic monohydrate (20.7 g), palladium (II) acetate (672 mg), 2-dicylohexylphosphino-2',6'-dimethoxybiphenyl (700 mg) and 150 ml of toluene and 3 ml of water were heated to reflux and stifled under nitrogen atmosphere for 24 hours. Hot reaction mixture was filtered through silica plug and evaporated, the residue was subjected to column chromatography on silica (eluent hexane/ethyl acetate 4/1 mixture), providing 4-(2,6-dimethoxyphenyl)-dibenzothiophene (9.00 g, prism crystals from ethyl acetate).

4-(2,6-Dimethoxyphenyl)-dibenzothiophene (9.00 g) and pyridinium hydrochloride (20 g) were placed in the 100 mL round-bottom flask, equipped with a magnetic stirrer. The flask was immersed in the pre-heated oil bath (220° C., 1 hour), cooled down to room temperature and dissolved in 200 ml of water. The solution was extracted with ethyl acetate (4×50 mL), organic fractions were combined, dried over sodium sulfate, filtered and evaporated, providing 2-(dibenzo[b,d]thiophen-4-yl)benzene-1,3-diol (7.2 g, white solid).

2-(Dibenzo[b,d]thiophen-4-yl)benzene-1,3-diol (7.2 g) was dissolved in 150 mL of dry DCM, containing 15 mL of pyridine. Solution was cooled in the ice bath, then triflic anhydride (18 mL in 25 mL of DCM) was added dropwise. Reaction was allowed to warm up to room temperature and washed with 10% sodium bicarbonate solution in water. DCM was evaporated, and the residue was subjected to column chromatography, providing 14.5 g of bis-triflate.

Triflate (5.56 g, 10 mmol), 4-dibenzothipheneboronic acid (5.35 g, 25 mmol), palladium (II) acetate (44 mg), 2-dicylohexylphosphino-2',6'-dimethoxybiphenyl (161 mg) and potassium phosphate tribasic trihydrate (7.00 g) were suspended in 100 ml of toluene and refluxed under nitrogen atmosphere for 24 hours. Hot reaction mixture was filtered and evaporated, the residue was crystallized from toluene twice. Sublimation (245° C., $10^{-5}$ mm Hg) provided 5.0 g of target compound.

2,6-Dimethoxyphenol (15.4 g, 0.1 mol) and 15 ml of pyridine were dissolved in 150 ml DCM and solution was cooled in the ice bath. Triflic anhydride was added dropwise upon vigorous stirring, reaction mixture was allowed to warm up to room temperature, washed with water and evaporated. Kugelrohr distillation (200° C., 2 mm Hg) provided 25 g of solidified clear oil.

2,6-Dimethoxytriflate (8.58 g, 30 mmol), 4-dibenzothipheneboronic acid (6.84 g, 30 mmol), potassium phos-

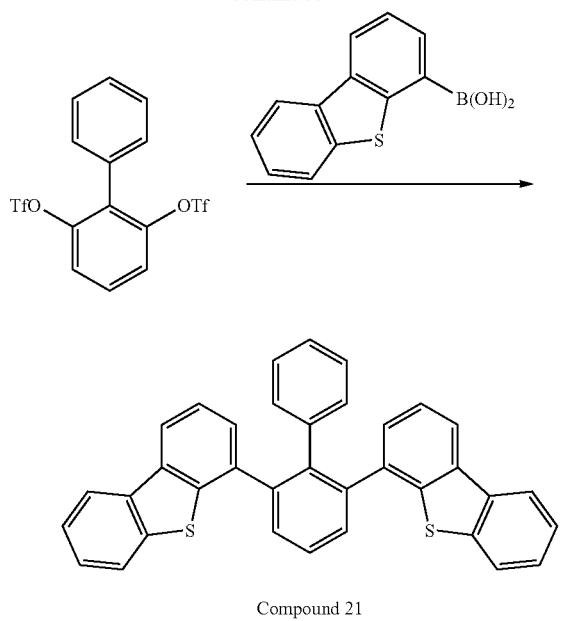

Compound 21

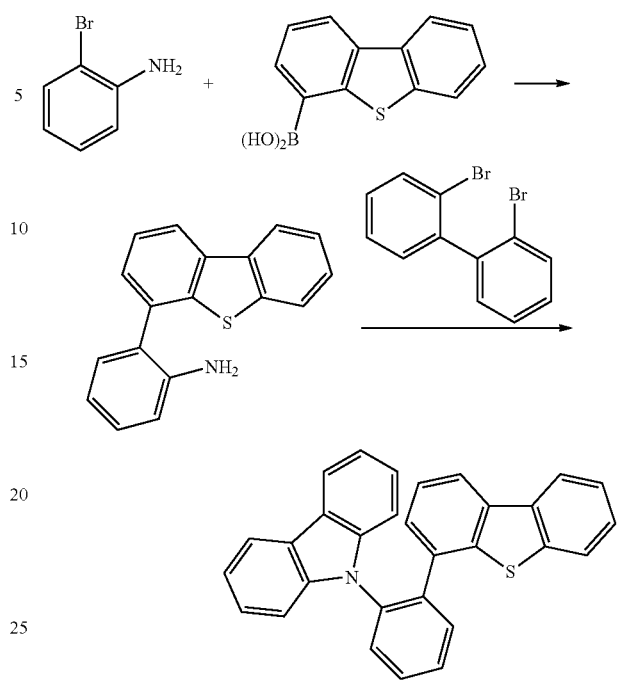

Compound 22

The 300 ml round-bottom flask equipped with reflux condenser and magnetic stirrer was charged with 2,6-dimethoxytriflate (10.00 g, 35 mmol), phenyl boronic acid (4.25 g, 35 mmol), potassium phosphate tribasic monohydrate (24.1 g), palladium (II) acetate (156 mg, 2 mol %), 2-dicylohexylphosphino-2',6'-dimethoxybiphenyl (573 mg, 4 mol %), toluene (100 ml) and water (2 ml). The reaction mixture was refluxed overnight, filtered through silica plug and evaporated. The residue was subjected to column chromatography on silica gel (eluent hexane/ethyl acetate 4/1 mixture), providing dimethoxybiphenyl as white solid (5.00 g).

2,6-Dimethoxybiphenyl (5.00 g) and 15 g of pyridinium hydrochloride were placed in the round-bottom flask and immersed in the oil bath (210° C., 1.5 hours). Then the reaction was cooled down to room temperature, diluted with 200 ml of water and extracted with ethyl acetate (4×50 ml). Organic fractions were combined, dried over sodium sulfate and evaporated. The residue was subjected to column chromatography on silica gel (eluent hexane/ethyl acetate 1/1 mixture), providing 3.3 of biphenyl-2,6-diol as yellow solid.

Biphenyl-2,6-diol (7.2 g, 39 mmol) was dissolved in DCM (100 ml) and pyridine (10 ml). The solution was cooled in the ice bath, and triflic anhydride (27.3 g) was added dropwise upon vigorous stirring. The reaction mixture was allowed to warm up to room temperature, was washed with water, dried and evaporated. The residue was subjected to column chromatography on silica gel (eluent hexane/ethyl acetate 4/1 mixture), providing 8.00 g of pure triflate.

The triflate (7.4 g, 16.4 mmol), 4-dibenzothiophene boronic acid (11.2 g, 49 mmol), potassium phosphate tribasic monohydrate (22.7 g), palladium (II) acetate (70 mg), 2-dicylohexylphosphino-2',6'-dimethoxybiphenyl (270 mg) and 100 ml of toluene were refluxed overnight under nitrogen atmosphere. The hot solution was filtered through silica plug and evaporated. The residue was crystallized hexane/ethyl acetate, providing target product as white solid (5.01 g). The material was additionally purified by sublimation (220° C., $10^{-5}$ mm Hg).

The 300 ml round-bottom flask equipped with reflux condenser and magnetic stirrer was charged with 2-bromoaniline (8.00 g, 46.5 mmol), 4-dibenzothiopheneboronic acid (10.5 g, 46.5 mmol), potassium carbonate (20 g, saturated solution in water), tetrakis(triphenylphoshine)palladium (0) (500 mg) and 100 ml of toluene. The reaction mixture was refluxed overnight under nitrogen atmosphere, filtered through silica plug and evaporated. Product was purified by column chromatography on silica gel, eluent hexane/ethyl acetate 4/1 mixture, providing 2-(dibenzo[b,d]thiophen-4-yl)aniline (10.1 g) as yellow oil.

2-(Dibenzo[b,d]thiophen-4-yl)aniline (10.1 g, 36.4 mmol), 2,2'-dibromobiphenyl (12.0 g, 38.5 mmol), sodium tert-butoxide (7.00 g, 72.9 mmol), and Pd₂(dba)₃ (330 mg) were charged into a 500 mL 3-neck flask with 300 mL of anhydrous toluene. This flask was evacuated and back filled with $N_2$ (this procedure was repeated a total of 3 times). Lastly, (5 mL, 96 mmol) P(t-Bu)₃ 1.0 M in toluene was syringed into the reaction vessel through a septum. The reaction mixture was heated at reflux for 18 h. Heating was then discontinued. The reaction mixture was diluted with 200 mL of water. The toluene layer was separated. The aqueous was extracted 1×200 mL toluene. The toluene extracts were combined, were dried over magnesium sulfate then were filtered and concentrated under vacuum. Crude material was washed with hexane and crystallized from toluene-DCM. The material was additionally purified by sublimation (190° C., $10^{-5}$ mm Hg), providing 6.23 g of pure crystalline material.

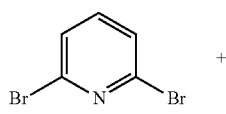

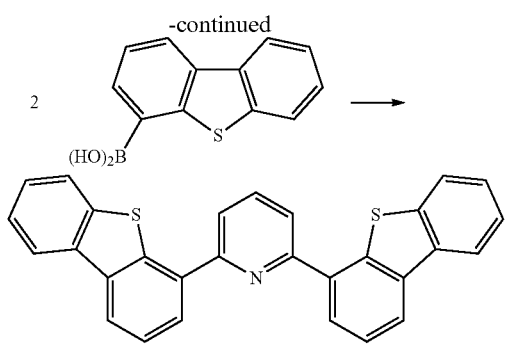

Compound 23

The 300 mL round-bottom flask equipped with magnetic stirrer and reflux condenser was charged with 2,6-dibromopyridine (2.20 g, 9.2 mmol), 4-dibenzothiopheneboronic acid (4.62 g, 20 mmol), $Pd_2(dba)_3$ (180 mg), S-phos (220 mg), potassium triphosphate (6.00 g) and 100 mL of anhydrous toluene. The flask was filled with nitrogen, and solution was stirred under reflux overnight. Then hot reaction mixture was filtered through silica plug, silica was washed with hot toluene. Organic fractions were combined and evaporated. The residue was subjected to column chromatography on silica gel (eluent hexane/ethyl acetate 4/1 mixture), providing target compound as white solid (3.01 g). Material was additionally purified by sublimation (225° C. at $10^{-5}$ mm Hg) and used for device fabrication.

Device Examples

All example devices were fabricated by high vacuum ($<10^{-7}$ Torr) thermal evaporation. The anode electrode is ~800 Å, 1200 Å or 2000 Å of indium tin oxide (ITO), or 800 Å Sapphire/IZO. The cathode consists of 10 Å of LiF followed by 1000 Å of Al. All devices are encapsulated with a glass lid sealed with an epoxy resin in a nitrogen glove box (<1 ppm of $H_2O$ and $O_2$) immediately after fabrication, and a moisture getter was incorporated inside the package.

The organic stack of Device Examples 1-8 consisted of sequentially, from the ITO surface (1200 Å), 100 Å of P1 as the hole injection layer (HIL), 300 Å of 4,4'-bis[N-(1-naphthyl)-N-phenylamino]biphenyl (α-NPD) as the hole transporting layer (HTL), 300 Å of the invention compound doped with 10 or 15 wt % of an Ir phosphorescent compound as the emissive layer (EML), 50 Å or 100 Å of HPT or the invention compound as the ETL2 and 400 or 450 Å of tris-8-hydroxyquinoline aluminum ($Alq_3$) as the ETL1.

Comparative Example 1 was fabricated similarly to the Device Examples except that CBP was used as the host.

The materials for the Emissive Layer, and the materials and thicknesses for ETL 2 and ETL1, of Device Examples 1-8 are provided in Table 2. The devices were tested, and the results measured are provided in Table 3. Compound is abbreviated using the term Cmpd.

TABLE 2

| Device Example | Host | Dopant wt % | ETL2 (Å) | ETL1 (Å) | ITO thickness (Å) |
|---|---|---|---|---|---|
| Comparative 1 | CBP | P1 10% | HPT (50) | $Alq_3$ (450) | 1200 |
| 1 | Cmpd 1 | P1 10% | Cmpd 1 (100) | $Alq_3$ (400) | 1200 |
| 2 | Cmpd 1 | P6 10% | Cmpd 1 (100) | $Alq_3$ (400) | 1200 |
| 3 | Cmpd 1 | P1 10% | HPT (50) | $Alq_3$ (450) | 1200 |
| 4 | Cmpd 1 | P6 10% | HPT (50) | $Alq_3$ (450) | 1200 |
| 5 | Cmpd 2 | P1 9% | HPT (50) | $Alq_3$ (400) | 800 |
| 6 | Cmpd 3 | P1 9% | HPT (50) | $Alq_3$ (400) | 800 |
| 7 | Cmpd 4 | P1 9% | HPT (50) | $Alq_3$ (400) | 1200 |
| 8 | Cmpd 5 | P1 9% | HPT (50) | $Alq_3$ (400) | 1200 |

TABLE 3

| Device Example | CIE X | CIE Y | Emission max (nm) | FWHM (nm) | At L = 1000 cd/m² V (V) | At L = 1000 cd/m² LE (cd/A) | At L = 1000 cd/m² EQE (%) | At L = 1000 cd/m² PE (lm/W) | At J = 40 mA/cm² $L_0$ (cd/m²) | At J = 40 mA/cm² $LT_{80\%}$ (hr) |
|---|---|---|---|---|---|---|---|---|---|---|
| Comparative 1 | 0.346 | 0.613 | 522 | 75 | 6.2 | 57.0 | 16 | 28.9 | 13,304 | 105 |
| 1 | 0.337 | 0.619 | 523 | 73 | 7.4 | 48.2 | 13 | 20.5 | 13,611 | 325 |
| 2 | 0.328 | 0.620 | 520 | 73 | 7.4 | 36.8 | 10 | 15.6 | 12,284 | 340 |
| 3 | 0.338 | 0.618 | 524 | 73 | 6.3 | 60.3 | 17 | 30.1 | 13,683 | 300 |
| 4 | 0.328 | 0.621 | 520 | 73 | 6.4 | 52 | 14.4 | 25.5 | 14,014 | 187 |
| 5 | 0.336 | 0.623 | 524 | 72 | 5.9 | 53.8 | 15 | 28.7 | 16389 | 18 |
| 6 | 0.349 | 0.614 | 528 | 73 | 6.1 | 45.5 | 12 | 23.2 | 15672 | 28 |
| 7 | 0.355 | 0.609 | 528 | 74 | 6.8 | 39.6 | 11 | 18.3 | 13403 | 98 |
| 8 | 0.353 | 0.613 | 528 | 72 | 6.3 | 49.5 | 14 | 24.7 | 15442 | 5.5 |

From Device Examples 1-8, it can be seen that the Invention Compounds as hosts in green phosphorescent OLEDs give high device efficiency (LE>35 cd/A at 1000 cd/m²), indicating dibenzothiophene as a chromophore has triplet energy high enough for efficient green electrophosphorescence. Most notably is the high stability of the device incorporating Compounds 1 as the host. Device Example 3 and Comparative Example 1 are only different in the host. Device Example 3 uses Compound 1 as the host whereas Comparative Example 1 uses the commonly used host CBP. The lifetime, $T_{80\%}$ (defined as the time required for the initial luminance, $L_O$, to decay to 80% of its value, at a constant current density of 40 mA/cm² at room temperature) are 300 hours and 105 hours respectively, with Device Example 3 having a slightly higher $L_0$. This translates to almost a 3 fold improvement in the device stability. The invention compounds may function well as the enhancement layer (ETL2). Device Example 1 and Device Example 3 both have Compound 1 as the host, but Compound 1 and 2,3,6,7,10,11-hexaphenyltriphenylene (HPT) as the enhancement layer respectively. They have $T_{0.8}$ of 325 and 300 hours respectively with similar $L_0$ (~13600 cd/m$^2$), indicating the good performance of the invention compound as the enhancement layer.

The data suggest that arylbenzothiophenes, particularly biphenyl substituted dibenzothiophenes, are excellent hosts and enhancement layer for phosphorescent OLEDs, providing as least the same efficiency and multiple times of improvement in stability compared to the commonly used CBP as the host.

A number of devices were fabricated having two different doped emissive layers, where the devices do not include a hole transport layer using a material such as NPD. Table 4 shows the structures for these devices. Table 5 shows measured experimental results for these devices. In general, the devices had an ITO anode, a hole injection layer of LG101™ (purchased from LG Chemical, Korea), and an emissive layer having a first organic layer and a second organic layer with an interface in between. Some of the devices had an enhancement layer (ETL2). All of the devices had an electron transport layer (ETL1) of LG201, available from the same source as LG101. Devices 9-16 have first and second organic layers with the same non-emissive materials, and different phosphorescent materials, where the first organic layer additionally includes a lower energy emissive material. All of devices 9-16 include emissive layers having a first and second organic layer with an interface in between. In all of these devices, the concentration of phosphorescent material is higher in the first (closer to anode) organic layer. The materials and thicknesses for Device Examples 9-16 are provided in Table 4. The devices were tested, and the results measured are provided in Table 5. Compound is abbreviated using the term Cmpd. All percentages are wt % unless otherwise noted.

TABLE 4

| Device | Anode | HIL | EML1 | EML2 | ETL2 | ETL1 |
|---|---|---|---|---|---|---|
| 9 | ITO [1200 Å] | LG101 [100 Å] | Cmpd 1: P4 (30%):P5 (0.5%) [300 Å] | Cmpd 1: P3 (18%) [250 Å] | none | LG201 [300 Å] |
| 10 | ITO [1200 Å] | LG101 [100 Å] | Cmpd 1: P4 (30%):P5 (0.5%) [300 Å] | Cmpd 1: P3 (12%) [250 Å] | none | LG201 [300 Å] |
| 11 | ITO [1200 Å] | LG101 [100 Å] | Cmpd 1: P4 (30%):P5 (0.5%) [300 Å] | Cmpd 1: P3 (24%) [250 Å] | none | LG201 [300 Å] |
| 12 | ITO [1200 Å] | LG101 [100 Å] | Cmpd 1: P4 (30%):P5 (0.5%) [300 Å] | Cmpd 1: P3 (24%) [250 Å] | Cmpd 1 [50 Å] | LG201 [300 Å] |
| 13 | ITO [1200 Å] | LG101 [100 Å] | Cmpd 1: P4 (30%):P5 (0.5%) [300 Å] | Cmpd 1: P3 (18%) [250 Å] | Cmpd 1 [50 Å] | LG201 [300 Å] |
| 14 | ITO [1200 Å] | LG101 [100 Å] | Cmpd 1: P4 (30%):P5 (0.5%) [300 Å] | Cmpd 1: P3 (12%) [250 Å] | Cmpd 1 [50 Å] | LG201 [300 Å] |
| 15 | ITO [1200 Å] | LG101 [200 Å] | Cmpd 1: P4 (30%):P5 (0.5%) [200 Å] | Cmpd 1: P3 (18%) [250 Å] | Cmpd 1 [50 Å] | LG201 [300 Å] |
| 16 | ITO [1200 Å] | LG101 [100 Å] | Cmpd 1: P4 (30%):P5 (0.5%) [200 Å] | Cmpd 1: P3 (18%) [250 Å] | Cmpd 1 [50 Å] | LG201 [300 Å] |

TABLE 5

| | At 1,000 cd/m$^2$ | | | | At 10 mA/cm$^2$ | | At $L_0$ = 1,000 cd/m$^2$ | |
|---|---|---|---|---|---|---|---|---|
| | V | LE | EQE | PE | | | | |
| Device | (V) | (cd/A) | (%) | (lm/W) | CIE x | CIE y | LT$_{70\%}$ (hr) | LT$_{60\%}$ (hr) |
| 9 | 6.1 | 23.7 | 10.9 | 12.3 | 0.467 | 0.457 | Not measured | Not measured |
| 10 | 6.2 | 31.7 | 15.1 | 16.1 | 0.500 | 0.445 | 35,500 | 100,000 |
| 11 | 6.2 | 14.9 | 6.9 | 7.5 | 0.467 | 0.457 | Not measured | Not measured |
| 12 | 6.1 | 29.5 | 13.5 | 15.2 | 0.456 | 0.460 | 78,000 | 140,000 |
| 13 | 6.3 | 32.4 | 15.3 | 16.1 | 0.437 | 0.451 | 90,000 | 230,000 |
| 14 | 7.0 | 33.2 | 16.3 | 15.0 | 0.505 | 0.439 | 88,000 | 180,000 |
| 15 | 6.4 | 29.0 | 13.9 | 14.3 | 0.472 | 0.449 | Not measured | Not measured |
| 16 | 6.2 | 29.4 | 14.2 | 14.9 | 0.467 | 0.448 | Not measured | Not measured |

From Device Examples 9, 10 and 11, it can be seen that the efficiency of the device decreased with increasing concentration of P3, and the device CIE red-shifted with decreasing P3 concentration. Device Examples 9-11 differ only in the concentration of the emissive compound P3 (i.e., devices contain varying concentrations of P3) as all of Device Examples 9-11 contained Inventive Compound 1 as the host, and were without a blocking layer between the EML and the LG201.

From Device Examples 12, 13, and 14, it can be seen that the efficiency of the device decreased with increasing concentration of P3, the device CIE red-shifted with decreasing P3 concentration, and device operating voltage increased with decreasing concentration of P3. Devices 12-14 differ only in the concentration of the emissive compounds P3, as all of devices 12-14 contained the inventive Compound 1 as the host and the blocking layer situated between the EML and ETL. Notably, Compound 1 is an efficient electron transport and blocking layer material, because the efficiency of each of Devices 12, 13, and 14 was shown to exceed that of Devices 9, 10, and 11. Also, the electron stability of Compound 1 was found to be significant, because Devices 12-14 demonstrated an $LT_{60\%}$ stability that exceeded 100,000 hrs from 1,000 $cd/m^2$ initial luminance.

From Device Examples 15 and 16, it can be seen that the devices show variation in device characteristics (e.g., CIE, efficiency) when the injection layer LG101 thickness is varied (e.g., 200 Å versus 100 Å).

The organic stack of Device Examples 17-20 consisted of sequentially, from the ITO surface, 100 Å of P1 as the hole injection layer (HIL), 300 Å of NPD as the hole transport layer (HTL), 300 Å of the invention compound doped with 10 wt % or 15 wt % of P1, an Ir phosphorescent compound, as the emissive layer (EML), 50 Å or 100 Å of HPT or the invention compound as enhancement layer (ETL2), an electron transport layer (ETL1) of $Alq_3$ having a thickness identified in Table 5, and a LiF/Al cathode. In particular, the BL and ETL have a sum total of 500 Å. Thus, the general device structure for the devices of Table 5 was: ITO(1200 Å)/P1 (100 Å)/NPD (300 Å)/Host: P1 x % (300 Å)/ETL2 (50 Å or 100 Å)/Alq3 (400 Å or 450 Å)/LiF(10 Å)/Al(1000 Å).

However, there was a difference in the device performance due to variation in the ETL1 layer. In devices having HPT as the ETL1 layer, the device efficiency was slightly higher due to stronger BL properties of HPT. However, the lifetime of the devices with Compound 23 as the ETL1 was longer. The data suggests that Compound 23 can be used as an efficient host for green phosphorescent emitter and as a ETL1 in the device. The stability of devices having Compound 23 as the ETL1 layer in the devices is higher than the stability of devices having a similar overall structure except with HPT as the ETL1 layer.

The organic stack of Device Examples 21-24 consisted of sequentially, from the anode surface, 100 Å of P1 or LG101 as the hole injection layer (HIL), 300 Å of NPD as the hole transport layer (HTL) or no HTL, 300 Å of the invention compound doped with 9 wt %, 15 wt % or 20 wt % of P2 or P7 Ir phosphorescent compounds as the emissive layer (EML), 50 Å, 150 Å or 250 Å of H1 as the enhancement layer (ETL2), and 200 Å, 300 Å or 400 Å of $Alq_3$ as the electron transport layer (ETL1). The materials and thicknesses of Device Examples 21-24 are provided in Table 7. The devices were tested, and the corresponding results measured are provided in Table 8.

TABLE 7

| Device | Anode | HIL | HTL | EML | ETL2 | ETL1 |
|---|---|---|---|---|---|---|
| 21 | ITO [800 Å] | LG101 [100 Å] | none | H1:P2 15% [600 Å] | H1 [250 Å] | $Alq_3$ [200 Å] |
| 22 | ITO [2000 Å] | LG101 [100 Å] | NPD [300 Å] | H1:P2 9% [300 Å] | H1 [50 Å] | $Alq_3$ [400 Å] |
| 23 | ITO [800 Å] | P1 [100 Å] | NPD [300 Å] | H1:P7 9% [300 Å] | H1 [50 Å] | $Alq_3$ [400 Å] |
| 24 | Sapphire/ IZO[800 Å] | LG101 [100 Å] | none | H1:P7 20% [300 Å] | H1 [150 Å] | $Alq_3$ [300 Å] |

TABLE 6

| Device example | Host Cmpd. | Dopant x % | ETL2 (Å) | ETL1 (Å) | CIE X | CIE Y | V (V) | L.E. (cd/A) | EQE (%) | PE (lm/W) | At 40 mA/cm² $L_0$ (cd/m²) | $LT_{80\%}$ (hr) |
|---|---|---|---|---|---|---|---|---|---|---|---|---|
| 17 | 23 | P1 10% | 23 (100 Å) | $Alq_3$ (400 Å) | 0.355 | 0.605 | 7.1 | 42.2 | 11.7 | 18.66 | 13,580 | 160 |
| 18 | 23 | P1 15% | 23 (100 Å) | $Alq_3$ (450 Å) | 0.353 | 0.609 | 6.8 | 42.1 | 11.6 | 19.44 | 14,521 | 155 |
| 19 | 23 | P1 1% | HPT (50 Å) | $Alq_3$ (450 Å) | 0.355 | 0.607 | 6.8 | 46.9 | 13 | 21.66 | 14,728 | 94 |
| 20 | 23 | P1 15% | HPT (50 Å) | $Alq_3$ (400 Å) | 0.352 | 0.611 | 6.6 | 44.9 | 12.3 | 21.36 | 15,070 | 63 |

The data in Table 6 describes the performance of Devices Examples 17-20. The voltage, luminous efficiency, external quantum efficiency and power efficiency data were measured at 1000 $cd/m^2$ (display level brightness). The lifetime was measured at accelerated conditions: 40 ma/cm² DC. The initial device luminance ($L_0$) at life-test conditions (40 mA/cm²) is also shown in Table 5. Compound 23 was used as a host for the green phosphorescent emitter P1. Two different dopant concentrations (10% or 15%) and two different ETL1 layers ($Alq_3$ of 400 Å or 450 Å) were varied in the devices and tested experimentally. The data show no significant difference in the device performance due to dopant concentration variation.

TABLE 8

| | At 1000 cd/m² | | | | At 10 mA/cm² | At $L_0$ = 1000 cd/m² |
|---|---|---|---|---|---|---|
| Device | V (V) | LE (cd/A) | EQE (%) | PE (lm/W) | CIE x   CIE y | $LT_{80\%}$ (hr) |
| 21 | 12.9 | 10.0 | 5.3 | 2.4 | 0.160   0.285 | 352 |
| 22 | 7.6 | 10.9 | 6.6 | 4.5 | 0.155   0.234 | 77 |
| 23 | 9.0 | 12.1 | 6.0 | 4.2 | 0.162   0.317 | 151 |
| 24 | 7.1 | 8.9 | 5.5 | 4.0 | 0.145   0.232 | 205 |

From Devices 21, 22, 23, and 24 it can be seen that the devices demonstrate differences between device structures having an emissive layer containing H1 and an emissive compound P2 or P7. Device Example 21 did not have an HTL, and used a thick EML to enhance device operational stability. The measured CIE coordinates of Device Example 21 were not blue saturated, so the structures of Device Examples 22, 23, and 24 used a 30 nm EML. Device Example 22 also incorporated a 200 nm ITO layer to saturate the device blue CIE. Device Example 23 was a standard blue PHOLED that was not optimized for operational stability. Device Example 24 was a blue PHOLED using the same emissive compound P7 as used in Device Example 23. However, Device Example 24 had several features that enabled longevity such as no NPD, sapphire heat sink substrate, a thick blocking layer, and high emitter concentration. Hence, the $LT_{80\%}$ of Device Example 24 exceeded the $LT_{80\%}$ of Device Example 23, and Device Example 24 had improved blue CIE compared to Device Example 23.

FIG. 3 shows an organic light emitting device having only a layer with a high hole conductivity between an emissive layer and the anode, an enhancement layer of the same material used as a non-emissive host in the emissive layer, and an emissive layer having first and second organic layers with different concentrations of phosphorescent material and non-emissive materials, where the concentration of phosphorescent material in the second organic layer is variable. The device of FIG. 3 includes a 10 nm thick hole injection layer of LG101, a 30 nm thick first organic emissive layer of H1 doped with 30 wt % P2, a 30 nm thick second organic emissive layer of H1 doped with X wt % P2, a 25 nm thick enhancement layer of H1, a 20 nm thick electron transport layer of $Alq_3$, and a LiF/Al cathode. X varies from 10 wt % to 18 wt % in the devices fabricated, with devices at X=10, 14 and 18 wt % as indicated in the legends for FIG. 4.

Figure 4:
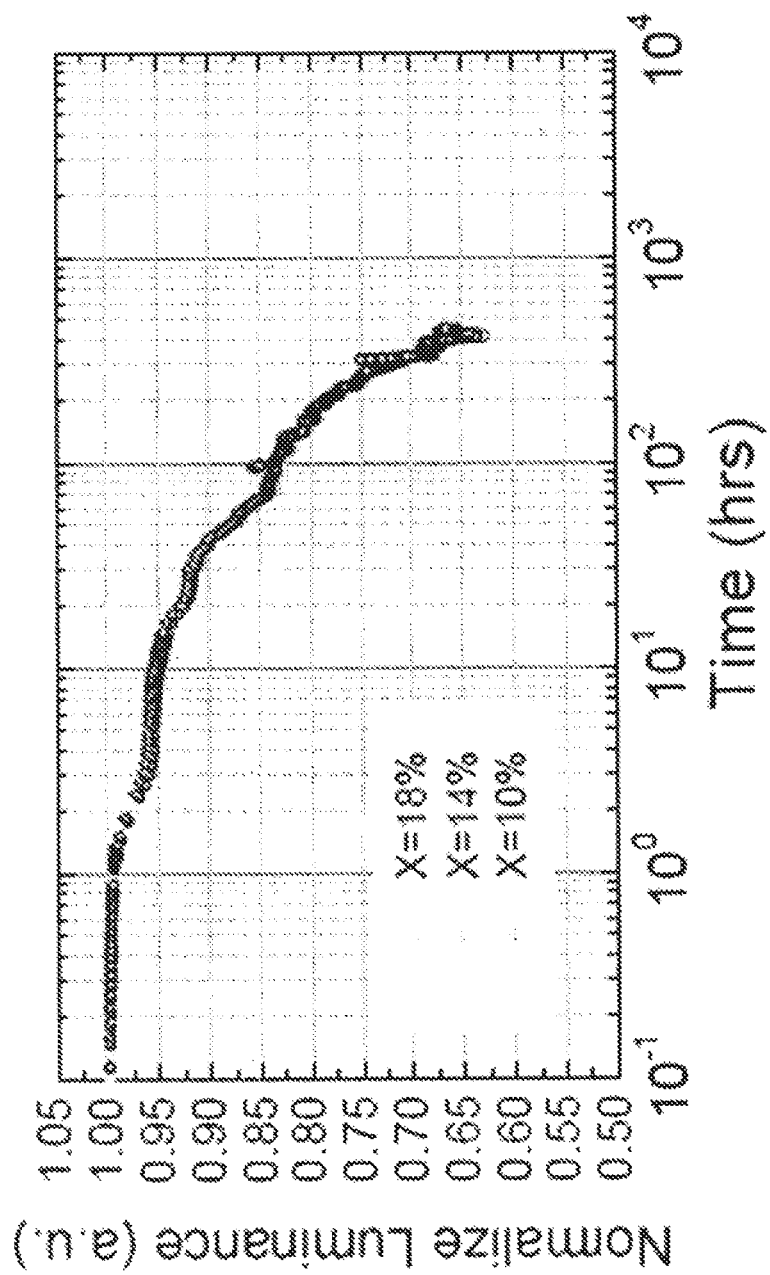
FIG. 4 shows a plot of normalized luminescence versus time for the device of FIG. 3.

FIG. 4 shows a plot of normalized luminescence versus time for the device of FIG. 3.

Figure 5:
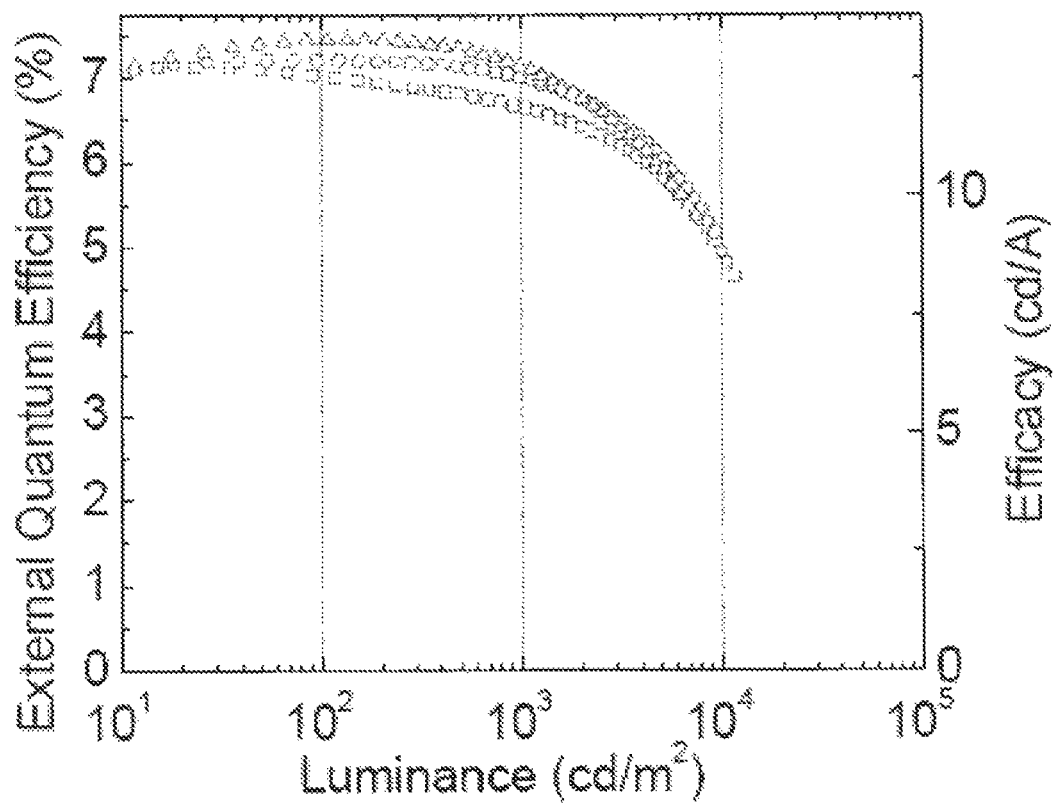
FIG. 5 shows a plot of external quantum efficiency versus luminance for the device of FIG. 3.

FIG. 5 shows a plot of external quantum efficiency versus luminance for the device of FIG. 3.

Figure 6:
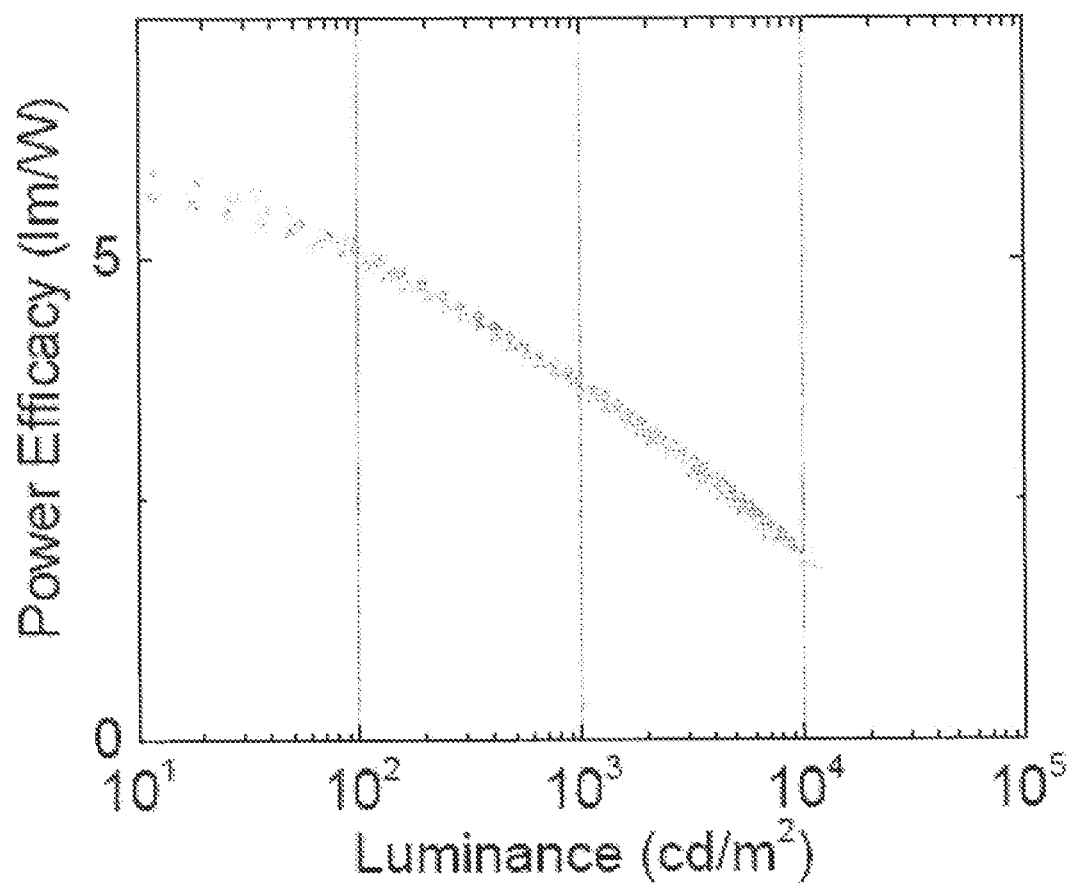
FIG. 6 shows a plot of power efficacy versus luminance for the device of FIG. 3.

FIG. 6 shows a plot of power efficacy versus luminance for the device of FIG. 3.

Figure 7:
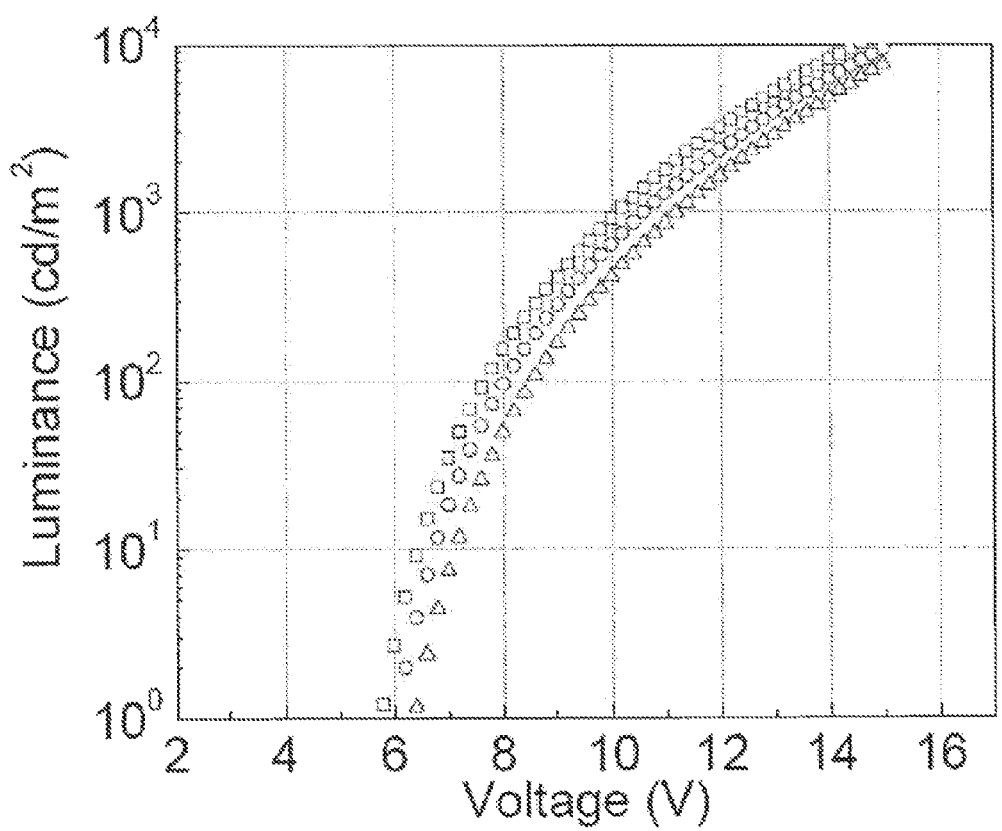
FIG. 7 shows a plot of luminance versus voltage for the device of FIG. 3.

FIG. 7 shows a plot of luminance versus voltage for the device of FIG. 3.

Figure 8:
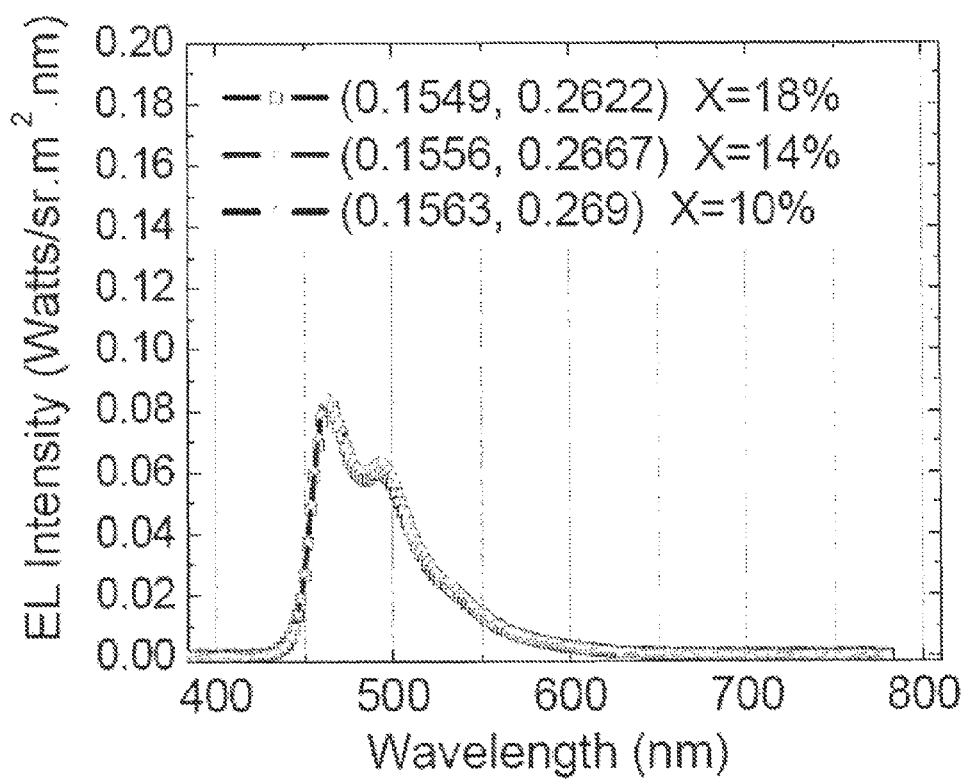
FIG. 8 shows a plot of EL intensity versus wavelength for the device of FIG. 3.

FIG. 8 shows a plot of EL intensity versus wavelength for the device of FIG. 3.

FIG. 9 shows an organic light emitting device having only a layer with a high hole conductivity between an emissive layer and the anode, an enhancement layer of the same material used as a non-emissive host in the emissive layer, and an emissive layer having first and second organic layers with different phosphorescent materials in the first and second organic layers, where the concentration of phosphorescent material in the second organic emissive layer is variable. The device of FIG. 9 includes a 10 nm thick hole injection layer of LG101, a 30 nm thick first organic emissive layer of H1 doped with 30 wt % P1, a 30 nm thick second organic emissive layer of H1 doped with X wt % P2, a 25 nm thick enhancement layer of H1, a 20 nm thick electron transport layer of $Alq_3$, and a LiF/Al cathode. X varies from 10 wt % to 18 wt % in the devices fabricated, with devices at X=10, 14 and 18 wt % as indicated in the legends for FIG. 4. The device of FIG. 9 is very similar to that of FIG. 3, with the difference being that the device of FIG. 9 uses different emissive phosphorescent material in the first and second organic emissive layers, while the device of FIG. 3 uses the same phosphorescent material in both layers. The concentrations of the phosphorescent materials are the same in the device of FIG. 3 compared to the device of FIG. 9.

Figure 10:
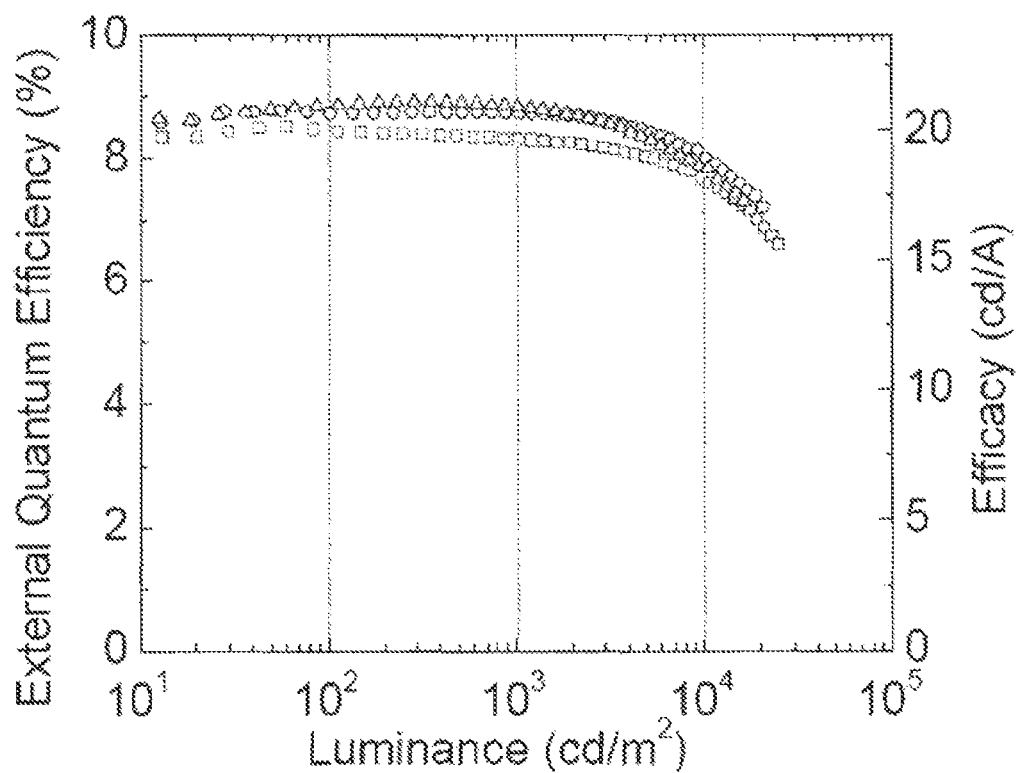
FIG. 10 shows a plot of external quantum efficiency versus luminance for the device of FIG. 9.

FIG. 10 shows a plot of external quantum efficiency versus luminance for the device of FIG. 9.

Figure 11:
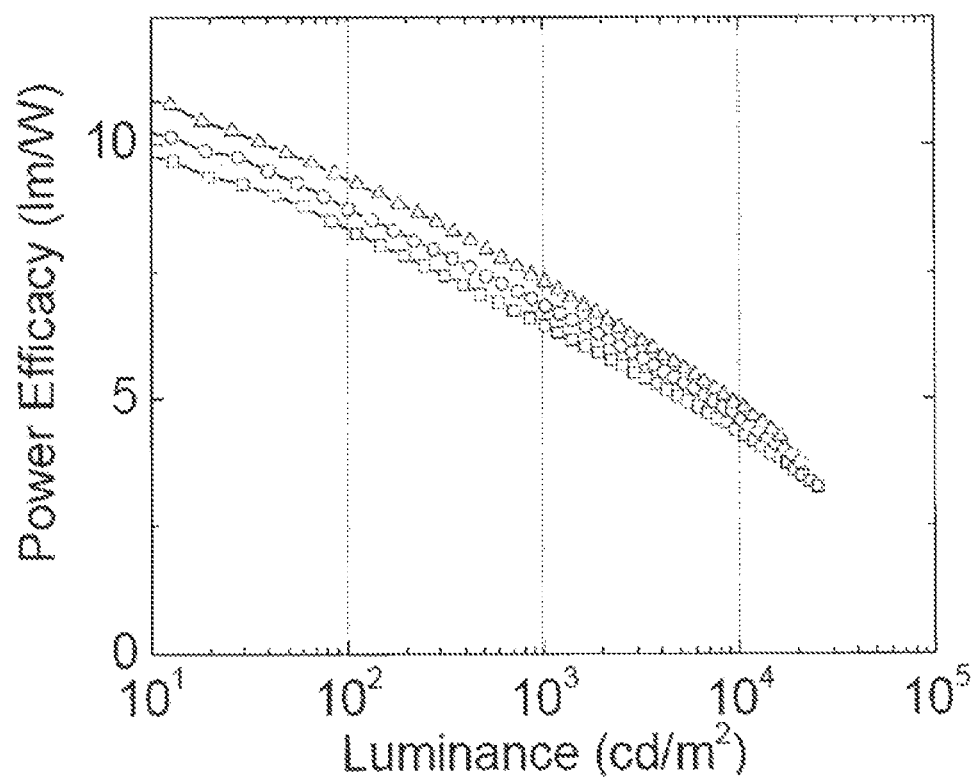
FIG. 11 shows a plot of power efficacy versus luminance for the device of FIG. 9.

FIG. 11 shows a plot of power efficacy versus luminance for the device of FIG. 9.

Figure 12:
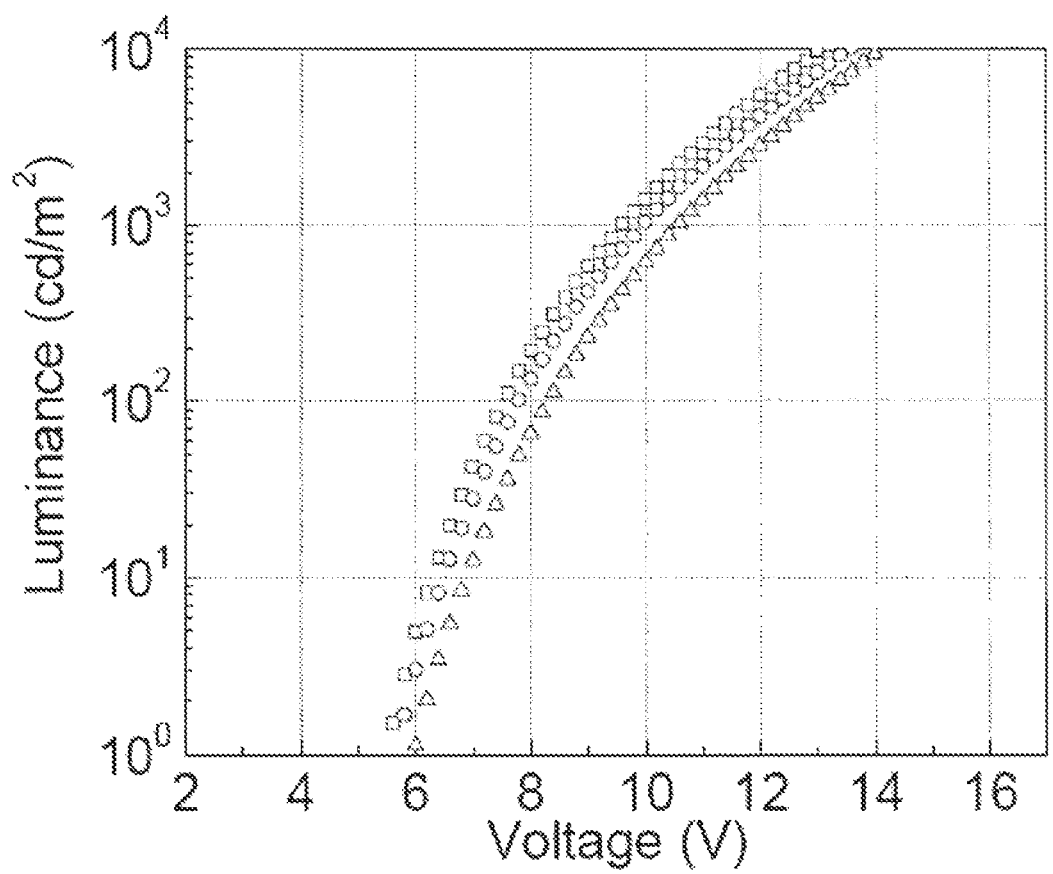
FIG. 12 shows a plot of luminance versus voltage for the device of FIG. 9.

FIG. 12 shows a plot of luminance versus voltage for the device of FIG. 9.

Figure 13:
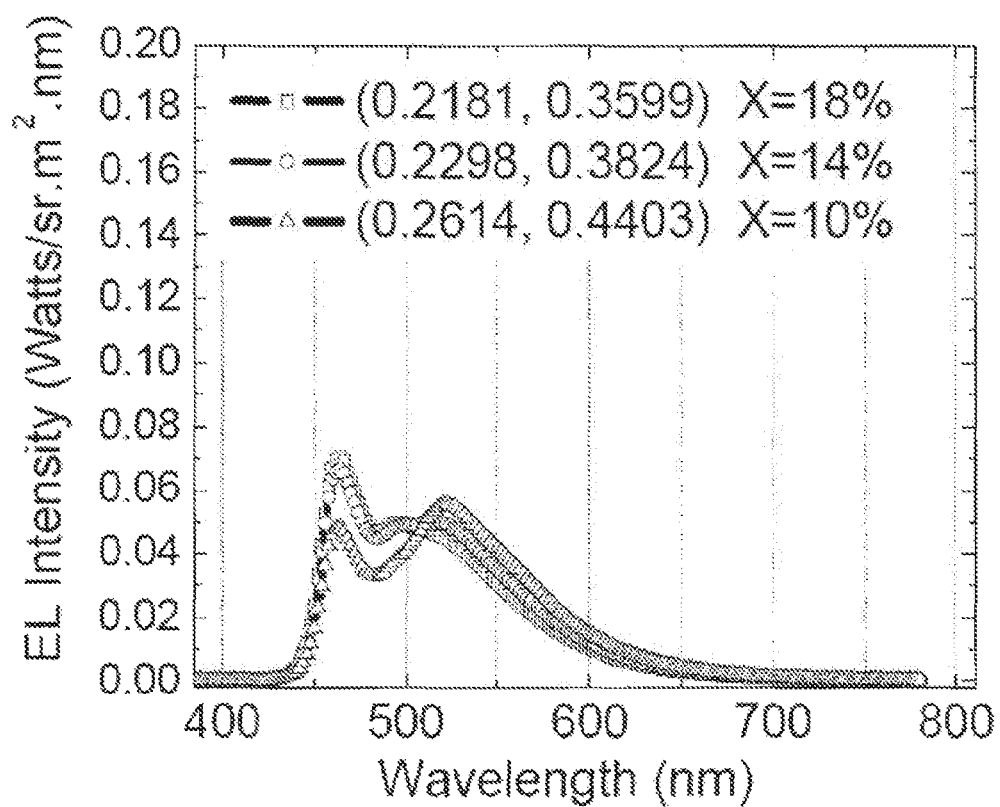
FIG. 13 shows a plot of EL intensity versus wavelength for the device of FIG. 9.
Figure 14:
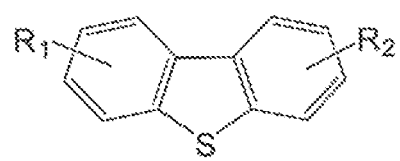
FIG. 14 shows a dibenzothiophene-containing compound.

FIG. 13 shows a plot of EL intensity versus wavelength for the device of FIG. 9.

The device of FIG. 9 may be compared to the device of FIG. 3. In terms of device architecture, the devices are similar except in the emissive layer, where the device of FIG. 9 has an emissive layer doped with phosphorescent emitter P1 and another emissive layer doped phosphorescent emitter P2, whereas the device of FIG. 3 has only phosphorescent emitter P2. Both devices have a step in dopant concentration, and similar concentrations even in the layers where the actual dopant is different. Several points can be understood from comparing these two device architectures. First, the device of FIG. 9 exhibits a broad emission spectra that is a combination of emission from both P1 and P2. As a result, it can be inferred that the device of FIG. 3 is emitting from both the layer doped with 30% P2 and the layer doped with a lesser concentration of P2. Comparing FIG. 5 to FIG. 10, it can be seen that the device of FIG. 9 has better charge balance than the device of FIG. 3, as evidenced by a relatively flat external quantum efficiency over three orders of magnitude for the device of FIG. 9 as compared to two orders of magnitude for the device of FIG. 3.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

The invention claimed is:

1. An organic light emitting device, comprising:
   an anode;
   a cathode;
   an emissive layer; and
   an enhancement layer, wherein

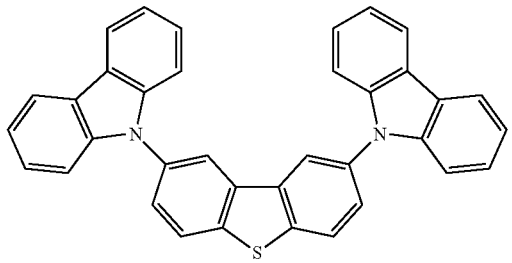

H1 is in the enhancement layer;
   wherein the emissive layer comprises an emissive dopant selected from the group consisting of:

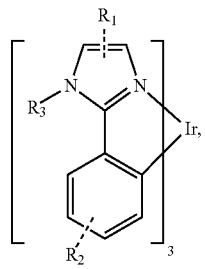

wherein $R_1$, $R_2$, and $R_3$ are independently selected from the group consisting of any alkyl, alkoxy, amino, alkenyl, alkynyl, arylkyl, aryl, heteroaryl, and hydrogen,
wherein (a) $R_1$ and $R_3$ form a fused ring that is, optionally, further substituted, (b) $R_2$ and $R_3$ form a fused ring that is, optionally, further substituted, or (c) both.

2. The device of claim 1, wherein $R_2$ and $R_3$ form a fused ring that is, optionally, further substituted.

3. The device of claim 2, wherein the emissive dopant comprises:

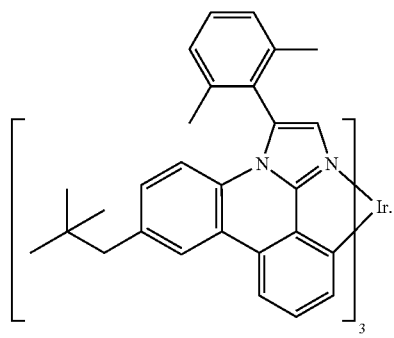

P2

4. The device of claim 2, wherein the emissive dopant comprises:

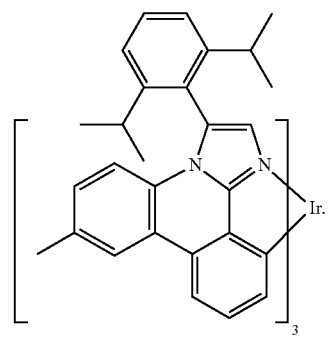

P7

5. The device of claim 1, wherein the emissive layer comprises H1 as a host.

6. The device of claim 1, wherein the enhancement layer is a hole blocking layer.

* * * * *